United States Patent
Kumar-Singh et al.

(10) Patent No.: US 10,351,617 B2
(45) Date of Patent: Jul. 16, 2019

(54) COMPOSITIONS, KITS AND METHODS FOR TREATMENT OF COMPLEMENT-RELATED DISORDERS

(71) Applicant: Trustees of Tufts College, Medford, MA (US)

(72) Inventors: Rajendra Kumar-Singh, Boston, MA (US); Soibhan M. Cashman, Boston, MA (US); Kasmir Ramo, Cambridge, MA (US)

(73) Assignee: Trustees of Tufts College, Medford, MA (US)

(*) Notice: Subject to any disclaimer, the term of this patent is extended or adjusted under 35 U.S.C. 154(b) by 328 days.

(21) Appl. No.: 13/766,142

(22) Filed: Feb. 13, 2013

(65) Prior Publication Data

US 2013/0143953 A1 Jun. 6, 2013

Related U.S. Application Data

(63) Continuation of application No. PCT/US2011/047761, filed on Aug. 15, 2011.

(60) Provisional application No. 61/373,596, filed on Aug. 13, 2010.

(51) Int. Cl.
| | |
|---|---|
| *C12N 15/00* | (2006.01) |
| *C07H 21/04* | (2006.01) |
| *C07K 14/705* | (2006.01) |
| *A61K 48/00* | (2006.01) |
| *C12N 15/85* | (2006.01) |
| *C12N 15/86* | (2006.01) |

(52) U.S. Cl.
CPC ...... *C07K 14/70596* (2013.01); *A61K 48/005* (2013.01); *C07H 21/04* (2013.01); *C12N 15/85* (2013.01); *C12N 15/86* (2013.01); *C12N 2710/10343* (2013.01); *C12N 2710/10371* (2013.01); *C12N 2750/14143* (2013.01); *C12N 2750/14171* (2013.01); *C12N 2800/00* (2013.01)

(58) Field of Classification Search
CPC .... C12N 15/85; C12N 15/86; C12N 2800/00; C07H 21/04
USPC ............... 435/320.1; 536/23.5, 24.1
See application file for complete search history.

(56) References Cited

U.S. PATENT DOCUMENTS

| | | | |
|---|---|---|---|
| 4,405,712 A | 9/1983 | Vande Woude et al. | |
| 4,650,764 A | 3/1987 | Temin et al. | |
| 4,797,368 A | 1/1989 | Carter et al. | |
| 4,861,719 A | 8/1989 | Miller | |
| 4,980,289 A | 12/1990 | Temin et al. | |
| 5,112,767 A | 5/1992 | Roy-Burman et al. | |
| 5,122,767 A | 6/1992 | Cameron et al. | |
| 5,124,263 A | 6/1992 | Temin et al. | |
| 5,139,941 A | 8/1992 | Muzyczka et al. | |
| 5,624,837 A | 4/1997 | Fodor et al. | |
| 5,882,893 A * | 3/1999 | Goodearl | C07K 14/70571 435/252.3 |
| 5,998,205 A | 12/1999 | Hallenbeck et al. | |
| 5,998,208 A | 12/1999 | Fraeful et al. | |
| 6,677,311 B1 | 1/2004 | Evans et al. | |
| 6,733,997 B1 | 5/2004 | Ding et al. | |
| 7,109,029 B2 | 9/2006 | Clark et al. | |
| 7,166,568 B1 | 1/2007 | Sims | |
| 7,166,658 B2 | 1/2007 | Harrison et al. | |
| 7,235,391 B2 | 6/2007 | Wu et al. | |
| 7,309,487 B2 | 12/2007 | Inana et al. | |
| 2003/0086940 A1 | 5/2003 | Costa et al. | |
| 2005/0265995 A1 | 12/2005 | Tomlinson et al. | |
| 2005/0287601 A1 | 12/2005 | Hageman et al. | |
| 2006/0263819 A1 | 11/2006 | Hageman et al. | |
| 2007/0093443 A1 | 4/2007 | Madison et al. | |
| 2007/0196367 A1 | 8/2007 | Dinu | |
| 2007/0203190 A1 | 8/2007 | Patil et al. | |
| 2008/0010179 A1 | 8/2008 | Kumar-Singh et al. | |
| 2008/0267980 A1 | 10/2008 | Tomlinson et al. | |
| 2010/0120665 A1 | 5/2010 | Kaleko et al. | |
| 2010/0209447 A1 | 8/2010 | Kumar-Singh et al. | |

FOREIGN PATENT DOCUMENTS

| | | |
|---|---|---|
| EP | 0338841 B1 | 3/1995 |
| WO | 85/05629 A1 | 12/1985 |
| WO | 87/04462 A1 | 7/1987 |
| WO | 89/01036 A1 | 2/1989 |
| WO | 89/07150 A1 | 8/1989 |
| WO | 90/02797 A1 | 3/1990 |
| WO | 90/02806 A1 | 3/1990 |
| WO | 90/13641 A1 | 11/1990 |
| WO | 92/05266 A1 | 4/1992 |
| WO | 92/07943 A1 | 5/1992 |
| WO | 92/14829 A1 | 9/1992 |
| WO | 93/14188 A1 | 7/1993 |

(Continued)

OTHER PUBLICATIONS

Fletcher et al, Structure, 1994, 2:185-199.*

(Continued)

*Primary Examiner* — Shin Lin Chen

(74) *Attorney, Agent, or Firm* — Foley Hoag LLP

(57) ABSTRACT

Methods, compositions and kits for regulating complement activity or treating a complement activity disorder in a subject using soluble, membrane-independent CD59 protein, methods of assaying human macular degeneration (MD), and methods and kits for assaying potential therapeutic agents for treatment of human MD are provided herein.

11 Claims, 48 Drawing Sheets

Specification includes a Sequence Listing.

(56) References Cited

FOREIGN PATENT DOCUMENTS

| WO | 97/17987 A1 | 5/1997 |
|---|---|---|
| WO | 2009102488 A2 | 8/2009 |

OTHER PUBLICATIONS

Sugita et al, Immunology, 1994, 82:34-41.*
Sugita et al, J Biochem, 1989, 106:555-557.*
Kieffer et al., 1994, Biochemistry, vol. 33, p. 4471-4482.*
Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/?p=962, Implications of protein fold switching, p. 1-4.*
Zufferey et al. (1997) "Multiply attenuated lentiviral vector achieves efficient gene delivery in vivo", Nature Biotechnology 15: 871-5.
Tatusova et al. (1999) "BLAST 2 Sequences, a new tool for comparing protein and nucleotide sequences", FEMS Microbiol Lett. 174(2): 247-250.
Bora et al. (2007) "CD59, a complement regulatory protein, controls choroidal neovascularization in a mouse model of wet-type age-related macular degeneration", J. Immunol. 178: 1783-1790.
Cohen et al. (1993) "Generation of varicella-zoster virus (VZV) and viral mutants from cosmid DNAs: VZV thymidylate synthetase is not essential for replication in vitro", Proc. Natl. Acad. Sci. USA, 90:7376-7380.
Cosset et al. (1990) "A new avian leukosis virus-based packaging cell line that uses two separate transcomplementing helper genomes", Journal of Virology 64(3): 1070-1078.
Cunningham et al. (1993) "A cosmid-based system for constructing mutants of Herpes Simplex Virus Type I", Virology 197: 116-124.
Davies et al. (1989) "Cd59, an ly6-like protein expressed in human lymphoid cells, regulates the action of the complement membrane attack complex on homologous cells" J. Exp. Med. 170: 637-654.
Dull et al. (1998) "A third-generation lentivirus vector with a conditional packaging system", Journal of Virology 72 (11): 8463-8471.
Edwards et al. (2005) "Complement Factor H Polymorphism and Age-Related Macular Degeneration", Science 308:421-424.
Eglitis et al. (1988) "Retroviral vectors for introduction of genes into mammalian cells", Biotechniques 6:608-14.
Evans (1989) "High efficiency vectors for cosmid microcloning and genomic analysis", Gene 79:9-20.
Flotte et al. (1992) "Gene expression from adeno-associated virus vectors in airway epithelial cells", Am J Respir. Cell Mol Biol. 7(3): 349-56.
Graham et al. (1977) "Characteristics of a human cell line transformed by DNA from human adenovirus type 5", J. Gen. Virol., 36:59-72.
Graham et al. (1991) "Manipulation of Adenovirus Vectors" in Methods in Molecular Biology: Gene Transfer and Expression Protocols 7, (Murray, Ed.), Humana Press, Clifton, NJ, 109-128.
Hageman et al. (2005) "A common haplotype in the complement regulatory gene factor H (HF1/CFH) predisposes individuals to age-related macular degeneration", Proc Natl Acad Sci USA 102(20): 7227-7232.
Haines et al. (2005) "Complement Factor H Variant Increases the Risk of Age-Related Macular Degeneration", Science 308: 419-421.
Hamilton et al. (1990) "Regulatory control of the terminal complement proteins at the surface of human endothelial cells: neutralization of a C5b-9 inhibitor by antibody to CD59", Blood 76: 2572-2577.
Harada et al. (1993) "Monoclonal antibody G6K12 specific for membrane-associated differentiation marker of human stratified squamous epithelia and squamous cell carcinoma", J Oral Pathol Med. 22(4).
Harlow et al. (1988) "Antibodies: A Laboratory Manual", Cold Spring Harbor Laboratory, pp. 93-117.
Hideshima et al. (1990) "Expression of HRF20, a regulatory molecule of complement activation, on peripheral blood mononuclear cells" 69(3): 396-401.
Holguin et al. (1989) "Relationship between the Membrane Inhibitor of Reactive Lysis and the Erythrocyte Phenotypes of Paroxysmal Nocturnal Hemoglobinuria", J. Clin. Invest. 84: 1387-94.
Inai et al. (1993) "Immunohistochemical detection of an enamel protein-related epitope in rat bone at an early stage of osteogenesis", Histochemistry 99(5): 355-62.
Kafri et al. (1997) "Sustained expression of genes delivered directly into liver and muscle by lentiviral vectors", Nature Genetics 17: 314-17.
Kaplitt et al. (1994) "Long-term gene expression and phenotypic correction using adeno-Associated virus vectors in the mammalian brain", Nature Genetics 8: 148-154.
Kaufman et al. (1982) "Amplification and expression of sequences cotransfected with a modular dihydrofolate reductase complementary dna gene", Mol. Biol. 159:601-621.
Klein et al. (2005) "Complement Factor H Polymorphism in Age-Related Macular Degeneration", Science 308(5720): 385-389.
Klein et al. (2007) "Fifteen-year cumulative incidence of age-related macular degeneration", Ophthalmology 114 (2): 253-62.
Korman et al. (1987) "Expression of human class II major histocompatibility complex antigens using retrovirus vectors", Proc. Natl. Acad. Sci. USA, 84: 2150-2154.
Laface et al. (1988) "Gene Transfer into Hematopoietic Progenitor Cells Mediated by an Adeno-Associated Virus Vector", Virology 162(2): 483-486.
Laughlin et al. (1986) "Latent Infection of KB cells with adeno-associated virus Type 2", Journal of Virology 60 (2): 515-24.
Lebkowski et al. (1988) "Adeno-associated virus: a vector system for efficient introduction and integration of DNA into a variety of mammalian cell types", Molecular and Cellular Biology 8(10): 3988-3996.
Levrero et al. (1991) "Defective and nondefective adenovirus vectors for expressing foreign genes in vitro and in vivo", Gene 101: 195-202.
Van Zijl et al. (1988) "Regeneration of herpesviruses from molecularly cloned subgenomic fragments", Journal of Virology 62 (6): 2191-95.
Markowitz et al. (1988) "A safe packaging line for gene transfer: separating viral genes on two different plasmids", Journal of Virology 62 (4): 1120-24.
McLaughlin et al. (1988) "Adeno-associated virus general transduction vectors: analysis of proviral structures", J. Virol. 62(6):1963-1973.
Miller et al. (1986) "Redesign of retrovirus packaging cell lines to avoid recombination leading to helper virus production", Molecular and Cellular Biology 6(8): 2895-902.
Miller et al. (1989) "Improved retroviral vectors for gene transfer and expression", BioTechniques 7(9): 980-990.
Morgenstern et al. (1990) "Advanced mammalian gene transfer: high titre retroviral vectors with multiple drug selection markers and a complementary helper-free packaging cell line", Nucleic Acids Res. 18:3587-3596.
Morgenstern et al. (1998) "DIALIGN: Finding local similarities by multiple sequence alignment", Bioinformatics, 14 (3): 290-4.
Mulder et al. (1993), "Characterization of two human monoclonal antibodies reactive with HLA-B 12 and HLA-B60, respectively, raised by in vitro secondary immunization of peripheral blood lymphocytes", Human Immunology 36: 186-92.
Muzyczka et al. (1992) "Use of adeno-associated virus as a general transduction vector for mammalian cells", Curr Top. Microbiol Immunol 158: 97-129.
Naldini et al. (1996) "In vivo gene delivery and stable transduction of nondividing cells by a lentiviral vector", Science 272: 263-7.
Nose et al. (1990) "Tissue distribution of HRF20, a novel factor preventing the membrane attack of homologous complement, and its predominant expression on endothelial cells in vivo", Immunology 70(2): 145-149.
Notredame et al. (1996) "SAGA: sequence alignment by genetic algorithm", Nucleic Acids Research 24(8): 1515-24.

(56) References Cited

OTHER PUBLICATIONS

O'Connor et al. (1989) "Construction of large DNA segments in *Escherichia coli*", Science 244: 1307-12.
Ohi et al. (1990) "Construction and replication of an adeno-associated virus expression vector that contains human B-globin cDNA", Gene, 89(2): 279-282.
McKusick (1989) "107271: CD59 Antigen; CD59", Online Mendelian Inheritance in Man (omim.org).
Orlean et al. (2007) "GPI anchoring of protein in yeast and mammalian cells, or: how we learned to stop worrying and love glycophospholipids", JLR 48: 993-1011.
Petranka et al. (1992) "Structure of the CD59-encoding gene: Further evidence of a relationship to murine lymphocyte antigen Ly-6 protein", Proc. Nat. Acad. Sci. 89: 7876-7879.
Rohrer et al. (2009) "A targeted inhibitor of the alternative complement pathway reduces angiogenesis in a mouse model of age-related macular degeneration", Invest Ophthalmol Vis Sci 50: 3056-3064.
Bora et al., "Recombinant membrane-targeted form of CD59 inhibits the growth of choroidal neovascular complex in mice" J Biol Chem, 2010, 285:33826-33833.
Ito et al. "J-19 Effect of recombinant soluble MACIF on complement-mediated lysis of Human umbilical vein endothelial cells" Proc. Jpn. Soc. Immul., 1993, vol. 23, p. 541 J-19 (1 pg.).
English translation of ITO et al. "J-19 Effect of recombinant soluble MACIF on complement-mediated lysis of Human umbilical vein endothelial cells" Proc. Jpn. Soc. Immul., 1993, vol. 23, p. 541 J-19 (1pg.).
Rollins et al. (1990) "The complement-inhibitory activity of cd59 resides in its capacity to block incorporation of c9 into membrane c5b-9", J. Immunol. 144: 3478-3483.
Sakoda et al. (1999) "A high-titer lentiviral production system mediates efficient transduction of differentiated cells including beating cardiac myocytes", J. Mol. Cell Cardiol., 31: 2037-47.
Zhou et al. (1993) "Adeno-associated virus 2-mediated gene transfer in murine hematopoietic progenitor cells", Exp Hematol 21(7): 928-33.
Samulski et al. (1989) "Helper-free stocks of recombinant adeno-associated viruses: normal integration does not require viral gene expression", J Virol 63: 3822-3828.
Samulski et al. (1991) "Targeted integration of adeno-associated virus (AAV) into human chromosome 19", The EMBO Journal 10(12): 3941-50.
Sawada et al. (1989) "Comlementary DNA sequence and deduced peptide sequence for CD59/MEM-43 antigen, the human homologue of murine lymphocyte antigen Ly-6C", Nucleic Acids Res 17(16): 6728.
Shelling et al. (1994) "Targeted integration of transfected and infected adeno-associated virus vectors containing the neomycin resistance gene", Gene Ther. 1(3): 165-9.
Sims et al. (1989) "Regulatory Control of Complement on Blood Platelets", J. Biol. Chem. 264(32): 19228-19235.
Stauber et al. (1993) "Rapid generation of monoclonal antibody-secreting hybridomas against African horse sickness virus by in vitro immunization and the fusion/cloning technique", J. Immunol. Methods, 161(2): 157-68.
Tan et al. (1999) "Temperature dependence of estrogen binding: importance of a subzone in the ligand binding domain of a novel piscine estrogen receptor", Biochimica et Biophysica Acta 1452: 103-120.
Tan et al. (2002) "Engineering a novel secretion signal for cross-host recombinant protein expression", Protein Engineering 15(4): 337-345.
Thompson et al. (1994) "CLUSTAL W: improving the sensitivity of progressive multiple sequence alignment through sequence weighting, position-specific gap penalties and weight matrix choice", Nucleic Acids Res. 22(22): 4673-80.
Tomkinson et al. (1993) "Epstein-Barr virus recombinants from overlapping cosmid fragments", Journal of Virology 67(12): 7298-306.
Tomlinson et al. (2009) "A Targeted Inhibitor of the Alternative Complement Pathway Reduces Angiogenesis in a Mouse Model of Age-Related Macular Degeneration", IOVS 50(7): 3056-3064.
Tratschin et al. (1984) "A human parvovirus, adeno-associated virus, as a eucaryotic vector: transient expression and encapsidation of the procaryotic gene for chloramphenicol acetyltransferase", Mol. Cell Biol. 4(10): 2072-81.
Tratschin et al. (1985) "Adeno-Associated Virus Vector for High-Frequency Integration, Expression, and Rescue of Genes in Mammalian Cells", Mol. Cell. Biol. 5(11): 3251-3260.
Urlaub et al. (1980) "Isolation of chinese hamster cell mutants deficient in dihydrofolate reductase activity", Proc. Natl. Acad. Sci. USA 77(7): 4216-20.
Van Leeuwen et al. (2003) "Epidemiology of age-related maculopathy: a review", Eur. J. Epidemiol., 18:845-854.
Vedeler et al. (1994) "The expression of CD59 in normal human nervous tissue", Immunology 82(4): 542-547.
Venkateswaran et al. (1992) "Production of anti-fibroblast growth factor receptor monoclonal antibodies by in vitro immunization", Hybridoma 11(6): 729-39.
Walsh et al. (1994) "Phenotypic correction of Fanconi Anemia in human hematopoietic cells with a recombinant adeno-associated virus vector", J. Clin. Invest. 94: 1440-48.
Walsh et al. (1991) "Transfection of human CD59 complementary DNA into rat cells confers resistance to human complement", Eur J. Immol 21(3): 847-850.
Wei et al. (1994) "Expression of the human glucocerebrosidase and arylsulfatase A genes in murine and patient primary fibroblasts transduced by an adeno-associated virus vector" Gene Ther. 1(4): 261-8.
Yoder et al. (1994) "Murine Yolk Sac Endoderm- and Mesoderm-Derived Cell Lines Support In Vitro Growth and Differentiation of Hematopoietic Cells", Blood 83(9): 2436-2443.
Yu et al. (1997) "Mapping the Active Site of CD59", Journal of Experimental Medicine 185(4): 745-753.
International Search Report and Written Opinion of the International Searching Authority received in PCT/US11/047761, dated Mar. 22, 2012 (11 pages).
Anderson et al., "A Role for Local Inflammation in the Formation of Drusen in the Formation of Drusen in the Aging Eye," J Ophthamol, 134(3):411-431 (2002).
Graham et al., "Chapter 11 Manipulation of Adenovirus Vectors in Methods," Methods in Molecular Biology, 7:109-128 (1991).
Harris et al., "Characterization of the mouse analogues of CD59 using novel monoclonal antibodies: tissue distribution and fuctional comparison," Immunol, 109:117-126 (2003).
Johnson et al., "A Potential Role for Immune Complex Pathogenesis in Drusen Formation," Exp Eye Res, 70:441-449 (2000).
Ramo et al., "Evaluation of Adenovirus-Delivered Human CD59 as a Potential Therapy for AMD in a Model of Human Membrane Attack Complex Formation on Murine RPE," Investig Ophthalmol, 49(9):4126-4136 (2008).
Sugita et al., "Molecular Cloning and Characterization of MACIF, an Inhibitor of Membrane Channel Formation of Complement," J Biochem, 106(4):555-557 (1989).
Sugita et al., "Recombinant soluble CD59 inhibits reactive haemolysis with complement," Immunology, 82:34-41 (1994).

* cited by examiner

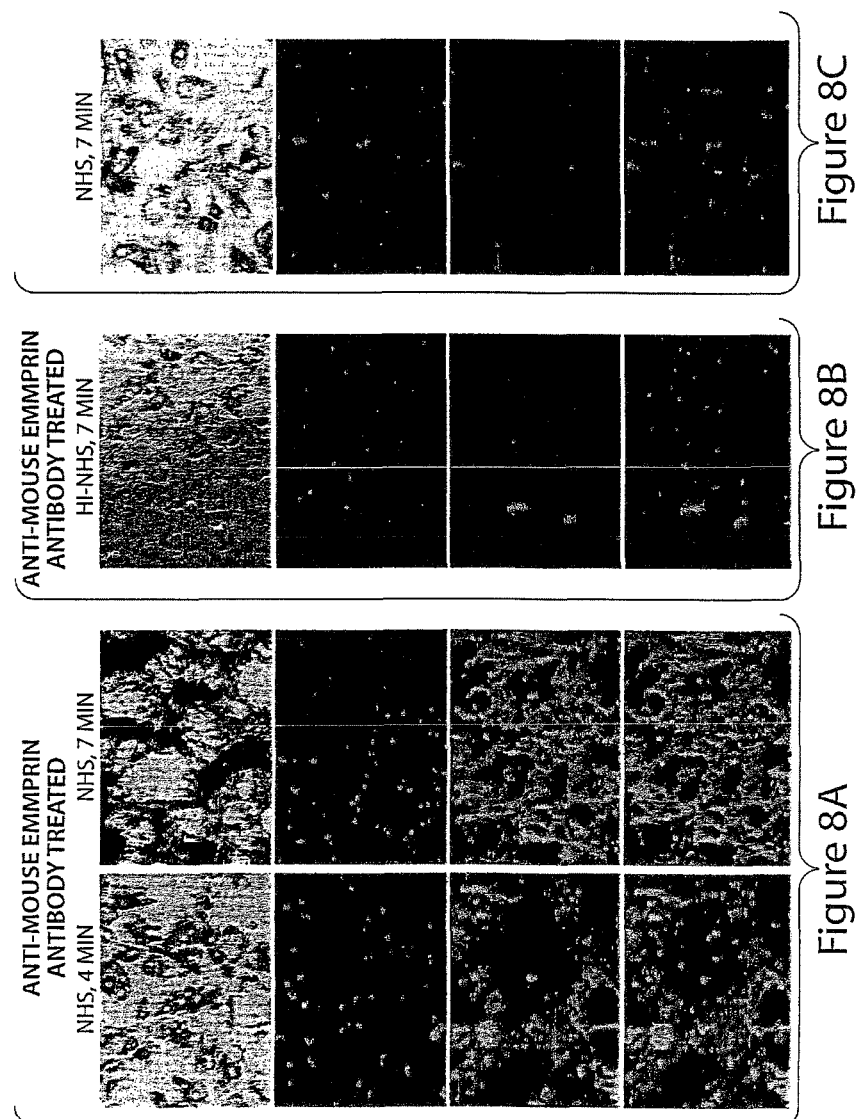

Subretinal Adenovirus
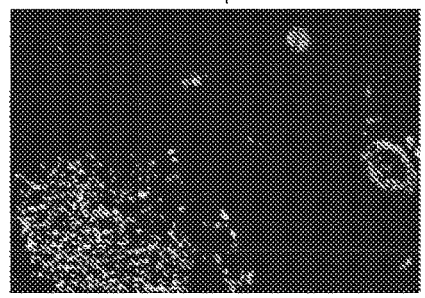
AdCAGpA
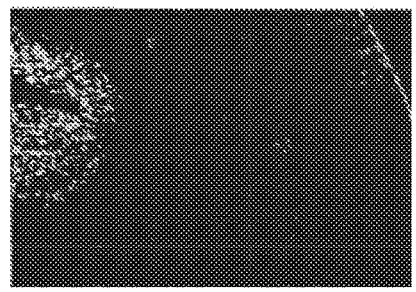
AdCAGsCD59
FIG. 23A
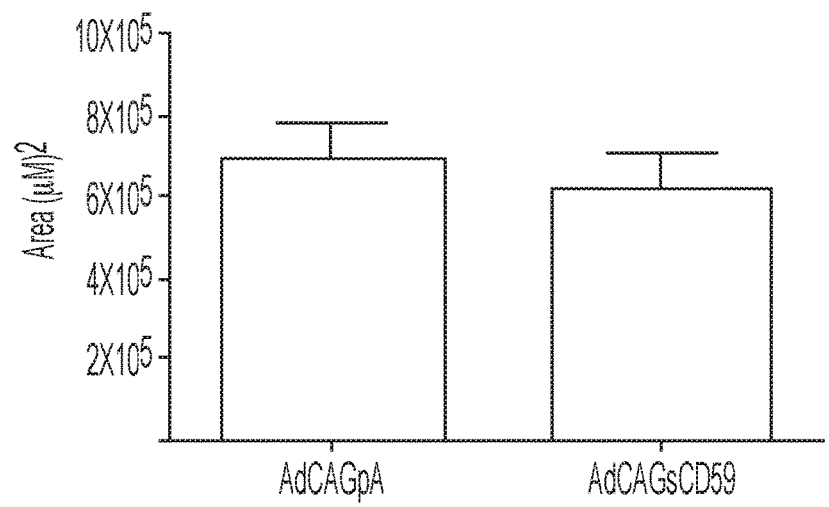
FIG. 23B Subretinal Adenovirus
AdCAGpA
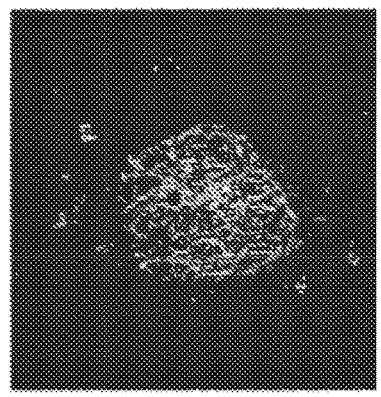
AdCAGsCD59
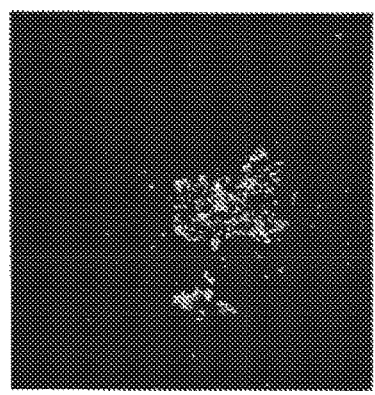
FIG. 24A
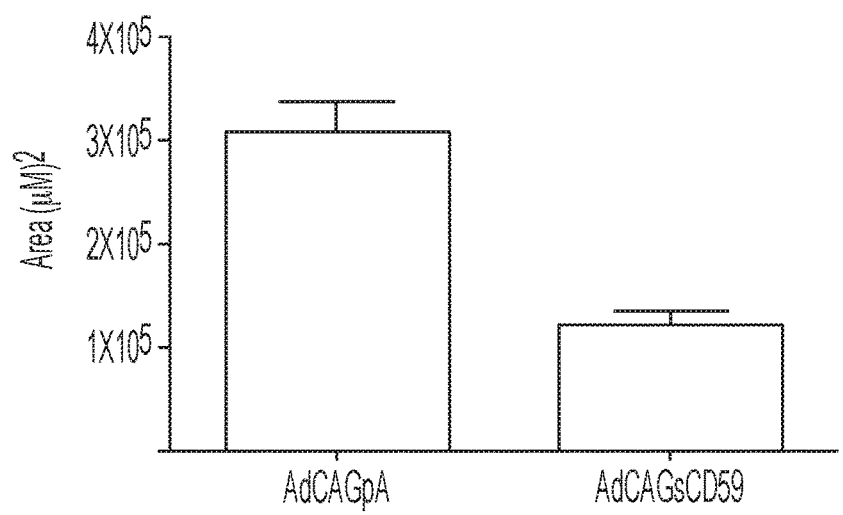
FIG. 24B Figure 26
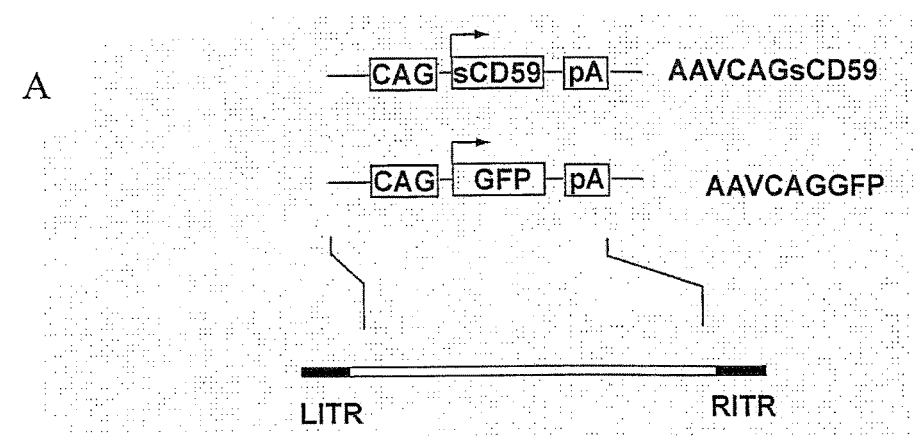
A
B
Intravitreal Adeno-Associated Virus (AAV)
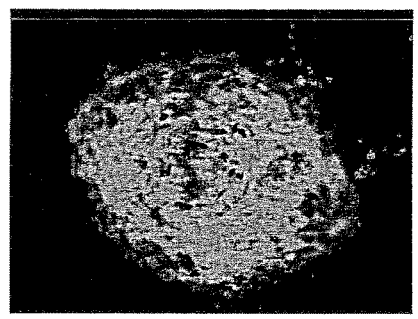
AAVCAGGFP        AAVCAGsCD59

COMPOSITIONS, KITS AND METHODS FOR TREATMENT OF COMPLEMENT-RELATED DISORDERS

RELATED APPLICATION

The present application claims the benefit of international application number PCT/US2011/047761 filed Aug. 15, 2011 entitled, "Compositions, kits and methods for treatment of complement-related disorders" inventors Rajendra Kumar-Singh, Siobhan M. Cashman, and Kasmir Ramo, which claims the benefit of U.S. provisional application Ser. No. 61/373,596 filed Aug. 13, 2010, which is hereby incorporated herein by reference in its entirety.

GOVERNMENT SUPPORT

This invention was made with government support under grant numbers EY014991 and EY013837 awarded by the National Institutes of Health. The government has certain rights in the invention.

TECHNICAL FIELD

Methods, compositions and kits for regulating complement activity or treating a complement activity disorder in a subject, methods for making a composition for treating a complement activity disorder in a subject, and methods and kits for assaying potential therapeutic agents for treatment of human MD are provided herein.

BACKGROUND

Age-related macular degeneration (AMD) is a disease associated with aging that gradually destroys sharp, central vision, and is the leading cause of blindness in the elderly (Klein et al. 2007 Ophthalmology 114: 253-262). The macula is a specific tissue located in the center of the retina, the light-sensitive tissue at the back of the eye that converts light or an image into electrical impulses.

AMD is classified as either wet or dry (Inana et al. U.S. Pat. No. 7,309,487 issued Dec. 18, 2007). Wet AMD is characterized by growth of abnormal blood vessels behind the retina under the macula. These new blood vessels are fragile and often leak blood and fluid. The blood and fluid raise the macula from its normal place at the back of the eye, causing loss of central vision. Wet AMD is treated with laser surgery, photodynamic therapy, and injections into the eye. None of these treatments, however, cures wet AMD, rather the treatments slow progression of the disease. Dry AMD is characterized by slow breakdown of light-sensitive cells in the macula, gradually blurring central vision in the affected eye. Over time, less of the macula functions and central vision is gradually lost. There is no known form of treatment for advanced stage dry AMD, and vision loss is inevitable. A specific high-dose formulation of antioxidants and zinc has been shown to prevent intermediate stage AMD from progressing to advanced AMD.

There is a need for methods of assaying (i.e., prognosticating or diagnosing) human macular degeneration (MD), methods of assaying among chemical entities to identify potential therapeutic agents to treat AMD, and methods of treating a human subject having AMD.

SUMMARY

An aspect of the invention provides a pharmaceutical composition including a nucleotide sequence encoding a membrane-independent CD59 protein and a pharmaceutically acceptable buffer, such that the composition is sufficiently pure for administration to a human subject In a related embodiments of the pharmaceutical composition, the nucleotide sequence includes ATGGGAATCCAAGGAGGGTCTGTCCTGTTCGGGCT-GCTGCTCGTCCTGGCTGTCTTCTGCCATTCAGGT-CATAGCCTGCAGTGCTACAACTGTCCTAAC-CCAACTGCTGACTGCAAAACAGCCGTCAATTGT-TCATCTGATTTTGATGCGTGTCTCATTACCAAAG-CTGGGTTACAAGTGTATAACAAGTGTTGGAAGT-TTGAGCATTGCAATTTCAACGACGTCACAA CCCGCTTGAGGGAAAATGAGCTAACGTACTACT-GCTGCAAGAAGGACCTGTGTAACTTTAAC-GAACAGCTTGAAAATTAA (SEQ ID NO: 5) or a portion or derivative therof. In various embodiments, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ID NO: 5 or a portion or derivative therof.

In a related embodiment of the pharmaceutical composition, the protein includes amino acid sequence MGIQGGSVLFGLLLVLAVFCHSGHSLQCYNCP-NPTADCKTAVNCSSDFDACLITKAGLQVYNKCWK-FEHCNFNDVTTRLRENELTYYCCKKDLCNF-NEQLEN (SEQ ID NO: 4) or a portion or derivative therof. In related embodiments of the pharmaceutical composition, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

In a related embodiment, the nucleotide sequence is operably linked to a promoter sequence causing expression of the protein in a cell, and the membrane-independent CD59 protein includes at least one mutation resulting in loss of function of a glycosyl phosphatidyl inositol (GPI) anchoring domain of the encoded CD59 protein. In various embodiments of the pharmaceutical composition, the at least one mutation includes at least one selected from the group of a substitution, a deletion, and an addition. The mutation for example is at an or adjacent to an omega position, whereby the mutation reduces or eliminates the attachment of the GPI anchor or reduces or eliminates the effective functionality of the GPI anchor to attach to a cell membrane.

In a related embodiment, the nucleotide sequence encoding the membrane-independent CD59 protein does not further encode a fusion to a peptide or protein domain that binds to a cell membrane or membrane associated entity.

In a related embodiment, the pharmaceutical composition is formulated sufficiently pure for administration to any mammalian subject, for example a cat, a dog, a cow, a pig, and a bat. In a related embodiment, the pharmaceutical composition is formulated for ocular delivery, for example formulated sterile for delivery in a dose effective to treat macular degeneration or formulated for delivery that is an injection. In various embodiments, the injection includes an intra-ocular injection, subconjunctival injection, or subtenon injection.

In a related embodiment, the pharmaceutical composition is formulated such that the nucleotide sequence is provided in a vector. In a related embodiment, the vector is an engineered viral vector recombinantly linked to the nucleotide sequence encoding the membrane-independent CD59 protein. For example the vector is at least one selected from an adenovirus, an adeno-associated virus, a herpesvirus, a poxvirus, and a lentivirus.

In related embodiments, the pharmaceutical composition is formulated to include a dose of the viral vector particles administered to an affected eye selected from a range of about $10^7$ to about $10^9$; about $10^8$ to about $10^{10}$; about $10^9$ to about $10^{11}$; about $10^{11}$ to about $10^{12}$; and about $10^{11}$ to about $10^{13}$.

In a related embodiment, the vector is a synthetic gene delivery vector for delivery of the nucleotide sequence, for example the synthetic gene delivery vector is selected from: a liposome, a lipid/polycation (LPD), a peptide, a nanoparticle, a gold particle, and a polymer.

In a related embodiment, the pharmaceutical composition further includes a pharmaceutically acceptable salt and a pharmaceutically acceptable emollient. In a related embodiment, the pharmaceutical composition is provided as an eye drop or an ointment. In a related embodiment, the pharmaceutical composition having sufficient purity to administer to a human, is formulated to be administered by at least one route selected from the group of: intravenous, intramuscular, intraperitoneal, intradermal, intrapulmonary, intravaginal, rectal, oral, buccal, topical, sublingual, intranasal, ocular, intraocular, and subcutaneous.

In related embodiments, the pharmaceutical composition further includes at least one agent selected from: an anti-tumor, an antiviral, an antibacterial, an anti-mycobacterial, an anti-fungal, an anti-proliferative and an anti-apoptotic.

In a related embodiment, the nucleotide sequence encoding the membrane-independent CD59 includes a deletion encoding at least one amino acid sequence in a GPI anchoring domain. In a related embodiment, the nucleotide sequence encoding the membrane-independent CD59 protein includes at least one single amino acid alteration resulting in decrease or loss of function of the GPI anchoring domain.

An aspect of the invention provides a method for making a composition for treating a subject for age-related macular degeneration (AMD) in a subject, the method including: providing a cell with a nucleotide sequence encoding a recombinant membrane-independent CD59 protein under conditions such that the cell expresses and secretes the CD59 protein locally, thereby making the composition for treating the subject, such that the composition is sufficiently pure for administration to the human subject.

In a related embodiment of the method, providing the cell with the nucleotide sequence is performed in vivo in the subject including contacting at least one ocular tissue of the subject with the cell, thereby treating the subject for AMD.

In a related embodiment, such that the providing is ex vivo, and the method further includes after providing the cell with the nucleotide sequence, injecting the cell and contacting at least one ocular tissue of the subject with the cell, thereby treating the subject for AMD.

In a related embodiment of the method, the cell is an autologous cell obtained from the subject. Alternatively, the cell is isologous or heterologous.

In related embodiments of the method, the nucleotide sequence is provided in a viral vector, for example the viral vector is derived from a genetically engineered genome of at least one virus selected from the group consisting of an adenovirus, an adeno-associated virus, a herpesvirus, and a lentivirus.

In a related embodiment of the method, the nucleotide sequence is provided in a synthetic gene delivery vector for example selected from: a liposome, a lipid/polycation (LPD), a peptide, a nanoparticle, a gold particle, and a polymer.

In related embodiments, the contacting is at least one of: subretinal; subconjunctival; subtenon; subcutaneous; intravenous; and intravitreal. In related embodiments, the injecting is at least one of: subretinal; subconjunctival; subtenon; subcutaneous; intravenous; and intravitreal. In related embodiments, the tissue includes at least one tissue selected from: retinal pigment epithelium, retina, choroid, sclera, Bruch's membrane, and choroidal blood vessels.

In a related embodiment of the method, the nucleotide sequence includes SEQ ID NO: 5 or a portion or derivative therof. In various embodiments of the method, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ID NO: 5 or a portion or derivative therof.

The protein in a related embodiment of the method includes amino acid sequence as shown in SEQ ID NO: 4 or a portion or derivative therof. In related embodiments of the method, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

An aspect of the invention provides a method of regulating complement activity or treating a complement activity disorder in a subject, the method including: contacting an affected tissue or organ of the subject at risk for or suffering from the complement activity disorder with a composition including a vector carrying a nucleotide sequence, encoding a membrane-independent human CD59 protein operably linked to a promoter sequence causing expression of the membrane-independent CD59 protein in a cell, such that the membrane-independent CD59 protein includes at least one mutation resulting in loss of function of glycosyl phosphatidyl inositol (GPI) anchoring domain, and such that the CD59 is soluble and is not further engineered to be membrane targeting; and, observing a physiological indicium of the complement activity disorder after contacting, in comparison to an abnormal amount of the physiological indicium observed prior to contacting, such that a decrease after contacting compared to prior to contacting is a positive indication that the affected tissue or organ is treated.

In a related embodiment, the composition is sufficiently pure to administer to a human or to any mammalian subject.

In a related embodiment of the method, the nucleotide sequence includes SEQ ID NO: 5 or a portion or derivative therof. In various embodiments of the method, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ED NO: 5 or a portion or derivative therof.

In a related embodiment of the method, the protein includes amino acid sequence as shown in SEQ ID NO: 4 or a portion or derivative therof. In related embodiments of the method, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

In related embodiments of the method, the affected tissue is selected from: epithelial, endothelial, and vascular. In related embodiments of the method, the affected organ or tissue is selected from: brain, eye, heart, kidney, mouth, throat, lung, stomach, liver, pancreas, knee, leg, hand, and vascular system.

In related embodiments of the method, the disorder is selected from: macular degeneration, age-related macular degeneration, inflammatory bowel disease, thyroiditis, cryoglobulinaemia, foetal loss, organ graft rejection, sepsis, viral infection, fungal infection, bacterial infection, toxic shock syndrome (TSS), membranoproliferative glomerulonephritis, dense deposit disease, peroximal nocturnal hemoglobinurea, lupus nephritis, membranous nephritis, immunoglobulin A nephropathy, goodpasture syndrome, post-streptococcal glomerulonephritis, systemic lupus erythematosus, atypical hemolytic uremic syndrome, systemic lupus erythromatosis, lupus arthritis, rheumatoid arthritis, Sjögren's syndrome, Behçet's syndrome, systemic sclerosis, Alzheimer's disease, multiple sclerosis, myasthenia gravis, Guillain-Barré syndrome, cerebral lupus, stroke, adult respiratory distress syndrome, chronic obstructive pulmonary disease, cystic fibrosis, haemolytic anaemia, paroxysmal cold haemoglobinuria, paroxysmal nocturnal haemoglobinuria, vasculitis, pemphigus, bullous pemphigoid, phototoxic reactions, psoriasis, anaphylactic shock, allergy, asthma, myocardial infarction, and atherosclerosis. In a related embodiment, the subject is a tissue or organ donor or recipient.

In a related embodiment, the disorder includes macular degeneration, and observing further includes measuring the indication selected from: visual acuity; visual aberrations; and amount of MAC deposition. In a related embodiment, the disorder includes bacterial infection or TSS, and observing further includes measuring the indication selected from: bacterial titer in a tissue or bodily fluid, extent of fever, and extent of inflammation. In a related embodiment, the disorder includes membranoproliferative glomerulonephritis, and observing further includes measuring the indication selected from: serum complement; urine protein; urine nitrogen; urine creatinine; glomerular filtration rate; effective renal blood flow; filtration fraction; and glomerular sieving. In a related embodiment, the disorder includes atherosclerosis, and observing further includes measuring the indication selected from: serum low density cholesterol; serum total cholesterol; angioscopy; and quantitative colorimetric angioscopy.

An aspect of the invention provides a method of assaying a serum complement component for prognosis or diagnosis of macular degeneration (MD), the method including: contacting a first sample of cells to a sample of a serum and measuring resulting lysis, and comparing extent of lysis to that in a second sample of control cells not so exposed to the serum and otherwise identical, such that the serum added to the first sample of cells is obtained from a patient in need of diagnosis for MD and an optional control serum is obtained from a normal subject and added to an optional third sample of cells, such that a greater extent of lysis in the first sample compared to that in the second sample and the optional third sample is an indication of prognosis or diagnosis of MD.

In a related embodiment, the method further involves contacting at least a fourth sample of cells to a candidate therapeutic composition and otherwise identically to the serum and measuring lysis, such that the extent of lysis of the third sample compared to that in the first sample and the second sample is a measure of protection by the candidate composition, thereby assaying for a potential therapeutic agent for efficacy in treatment of macular degeneration.

In a related embodiment, the method further includes prior to contacting with serum, contacting the cells with a vector encoding a gene capable of expressing a recombinant membrane-independent human CD59 (rmihCD59) protein.

In related embodiments of the method, the rmihCD59 protein lacks a glycosyl phosphatidyl inositol anchoring domain, and such that a decrease in cell lysis in the presence of rmihCD59 compared to absence of rmihCD59 is an indicium of suitability of the patient for treatment of macular degeneration with srCD59.

In a related embodiment of the method, the protein includes amino acid sequence as shown in SEQ ID NO: 4 or a portion or derivative therof. In related embodiments of the method, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

In a related embodiment of the method, the vector encoding the gene includes a nucleotide sequences as shown in SEQ ID NO: 5 or a portion or derivative thereof. In various embodiments of the method, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ID NO: 5 or a portion or derivative therof.

An aspect of the invention provides a pharmaceutical composition comprising a membrane-independent CD59 protein as shown in SEQ ID NO: 4; and a pharmaceutically acceptable buffer, wherein the composition is sufficiently pure for administration to a human subject.

In a related embodiment of the pharmaceutical composition, the nucleotide sequence includes SEQ ID NO: 5 or a portion or derivative therof. In various embodiments, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ID NO: 5 or a portion or derivative therof.

In a related embodiment of the pharmaceutical composition, the protein includes amino acid sequence SEQ ID NO: 4 or a portion or derivative therof. In related embodiments of the pharmaceutical composition, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

In a related embodiment of the pharmaceutical composition, the membrane-independent CD59 protein includes at least one mutation resulting in loss of function of a glycosyl phosphatidyl inositol (GPI) anchoring domain of the encoded CD59 protein; the mutation in various embodiments includes at least one selected from the group of: a substitution, a deletion, and an addition.

In a related embodiment, the membrane-independent CD59 protein does not further encode a fusion to a peptide or protein domain that binds to a cell membrane or membrane associated entity.

In a related embodiment, the pharmaceutical composition is formulated sufficiently pure for administration to any mammalian subject for example a horse, a cow, a goat, a dog, and a cat. The pharmaceutical composition in a related embodiment is formulated for ocular delivery. In a related embodiment, the pharmaceutical composition is formulated sterile for delivery in a dose effective to treat macular degeneration for example wet age-related macular degeneration.

In various embodiments, the pharmaceutical composition is formulated for delivery that is an injection, for example intra-ocular injection, subconjunctival injection, or subtenon injection. In related embodiments, the pharmaceutical composition further includes at least one selected from the group of: a liposome, a lipid/polycation (LPD), a peptide, a nanoparticle, a gold particle, and a polymer. For example, the composition further includes a peptide for overall delivery composition.

In related embodiments, the pharmaceutical composition further includes a pharmaceutically acceptable salt and a pharmaceutically acceptable emollient. In a related embodiment, the pharmaceutical composition is provided as an eye drop or an ointment. In a related embodiment, the pharmaceutical composition is a solution that is at least one selected from the group of: buffered, pH neutral, and isotonic.

The pharmaceutical composition is various embodiments is formulated for at least one route selected from the group of: intravenous, intramuscular, intraperitoneal, intradermal, intrapulmonary, intravaginal, rectal, oral, buccal, topical, sublingual, intranasal, ocular, intraocular, and subcutaneous. In various embodiments, the pharmaceutical composition further includes at least one agent selected from the group consisting of: anti-tumor, antiviral, antibacterial, anti-myco-bacterial, anti-fungal, anti-proliferative and anti-apoptotic.

In a related embodiment of the pharmaceutical composition, the protein includes a deletion encoding at least one amino acid sequence in a GPI anchoring domain. In a related embodiment, the protein includes at least one single amino acid alteration resulting in decrease or loss of function of the GPI anchoring domain.

An aspect of the invention provides a kit for regulating complement activity or treating a complement activity disorder in a subject, the kit comprising: a pharmaceutical composition including a membrane-independent CD59 protein and/or a nucleotide sequence encoding the CD59 protein, such that the composition is sufficiently pure for administration to the subject; instructions for use; and, a container.

In a related embodiment of the kit, the nucleotide sequence includes SEQ ID NO: 5 or a portion or a derivative thereof. In various embodiments of the kit, the nucleotide sequence includes at least about 30%, about 35%, about 40%, about 45%, about 50%, about 55%, about 60%, about 65%, about 70%, about 75%, about 80%, about 85%, about 90%, about 95%, or about 99% identity to SEQ ID NO: 5 or a portion or derivative therof.

In a related embodiment of the kit, the protein includes amino acid sequence as shown in SEQ ID NO: 4 or a portion or derivative therof. In various embodiments of the kit, the protein includes an amino acid sequence at least about 30%, about 35%, about 40%, about 45%, about 50%, about 55%, about 60%, about 65%, about 70%, about 75%, about 80%, about 85%, about 90%, about 95%, or about 99% identical to SEQ ID NO: 4.

In a related embodiment of the kit, the nucleotide sequence is operably linked to a promoter sequence causing expression of the protein in a cell, such that the membrane-independent CD59 protein includes at least one mutation resulting in loss of function of a glycosyl phosphatidyl inositol (GPI) anchoring domain of the encoded CD59 protein. For example, the mutation is at least one selected from the group of: a substitution, a deletion, and an addition.

In a related embodiment, the nucleotide sequence encoding the membrane-independent CD59 protein does not further encode a fusion to a peptide or protein domain that binds to a cell membrane or membrane associated entity.

The kit in various embodiments further includes an applicator for contacting or administering the pharmaceutical composition to the subject, for example the applicator is at least one selected from the group of: a bottle, a sprayer, a fluid dropper, a solution dropper, an inhaler, a gauze, a strip, a brush, and a syringe.

In various embodiments of the kit, the composition is formulated for delivery to the subject, for example the composition is formulated as an injection; a cream, an ointment; a lotion; an oil; a spray; a powder; a patch; a solution such as an ophthalmic solution, an irrigation solution, or an eye drop solution; or a contact lens.

In a related embodiment of the kit, the composition is formulated sufficiently pure for administration to a subject which is a mammal for example a human, a cow, a dog, a cat, a pig, and a horse.

In a related embodiment of the kit, the composition is formulated for ocular delivery. In a related embodiment, the composition is formulated sterile for delivery in a dose effective to treat the complement activity or the disorder. In various embodiments of the kit, the composition is formulated for delivery that is an injection, for example intraocular injection, subconjunctival injection, or subtenon injection.

In a related embodiment of the kit, the composition is formulated wherein the nucleotide sequence is provided in a vector. In a related embodiment, the vector is an engineered viral vector recombinantly linked to the nucleotide sequence encoding the membrane-independent CD59 protein. For example, the vector is at least one selected from an adenovirus, an adeno-associated virus, a herpesvirus, a poxvirus, and a lentivirus. In various embodiments of the kit, the composition is formulated to include a dose of the viral vector particles administered to an affected eye selected from a range of about $10^7$ to about $10^9$; about $10^8$ to about $10^{10}$; about $10^9$ to about $10^{11}$; about $10^{11}$ to about $10^{12}$; and about $10^{11}$ to about $10^{13}$. In a related embodiment, the vector is a synthetic gene delivery vector for delivery of the nucleotide sequence. In a related embodiment, the synthetic gene delivery vector is selected from the group of: a liposome, a lipid/polycation (LPD), a peptide, a nanoparticle, a gold particle, and a polymer. In a related embodiment, the kit and/or composition further comprises a POD composition.

In a related embodiment, the composition further includes a pharmaceutically acceptable salt and a pharmaceutically acceptable emollient. In related embodiments of the kit, the composition is provided or formulated as an eye drop or ointment. In a related embodiment, the composition is of sufficient purity to administer to a mammal. For example the composition is of sufficient purity to administer to a human, a dog, a cat, a horse, a pig, or a cow.

In various embodiments of the kit, the pharmaceutical composition further includes at least one agent selected from the group consisting of: anti-tumor, antiviral, antibacterial, anti-mycobacterial, anti-fungal, anti-proliferative and anti-apoptotic.

In a related embodiment of the kit, the nucleotide sequence encoding the membrane-independent CD59 includes a deletion encoding at least one amino acid sequence in a GPI anchoring domain. For example, the nucleotide sequence includes a deletion of the C-terminal 26 amino acids encoding the signal sequence for attachment of the GPI anchor.

In related embodiments of the kit, the protein and/or the nucleotide sequence encoding the protein includes a deletion of the C-terminal amino acids, for example the deletion is of at least: about one amino acid to four amino acids, about four amino acids to eight amino acids, about eight amino acids to 12 amino acids, about 12 amino acids to about 16 amino acids, about 16 amino acids to about 20 amino acids, or about 20 amino acids to about 24 amino acids.

In a related embodiment of the kit, the protein and/or the nucleotide sequence encoding the membrane-independent protein includes at least one single amino acid alteration resulting in decrease or loss of function of the GPI anchoring domain.

In various embodiments of the kit, the pharmaceutical composition is any pharmaceutical composition described herein. The kit in related embodiments includes the instructions selected from the group of: a method of assaying a serum complement component for prognosis or diagnosis of macular degeneration; a method of making a composition for treating a subject for age-related macular degeneration (AMD) in a subject, and a method of regulating complement activity or treating a complement activity disorder in a subject.

An aspect of the invention provides a pharmaceutical composition comprising: a membrane-independent CD59 protein as shown in SEQ ID NO: 4, or a vector carrying a nucleotide sequence as shown in SEQ ID NO: 5 that encodes the protein, such that the vector including an adenovirus vector or an adeno-associated virus vector; and a pharmaceutically acceptable buffer, such that the composition is sufficiently pure for administration to a human subject.

BRIEF DESCRIPTION OF THE DRAWINGS

FIG. 1 panel B is a photograph of Western blots using a monoclonal antibody specific for binding to human CD59 (top) and for control protein actin (bottom), showing presence of human CD59 in lysates of cells contacted with AdCAGCD59 (dark band at approximately 18 kD in the mouse hepa-1c1c7 cell lysate group, left channel). CD59 signal was not detected in cell lysates from cells contacted with the control virus vector or in lysates in control cells not contacted with vector (mouse hepa-1c1c7 cell lysate group, middle and right channels). Endogenous human CD59 was also detected in human embryonic retinoblast (911) cell lysates (faint band at approximately 18 kD in the 911 cell lysate group). This signal was much weaker compared to the signal from the mouse cells contacted with AdCAGCD59 (comparing dark band at approximately 18 kD in the mouse hepa-1c1c7 cell lysate group, left channel to faint band at approximately 18 kD in the 911 cell lysate group). The second Western blot was a control for expression of housekeeping gene β-actin.

FIG. 1 panel C is a set of photomicrographs showing AdCAGCD59 contacted cells (left), and these cells immunostained with anti-hCD59 antibody (right; indicated CD59). The left top photomicrograph was visualized using differential interference contrast (DIC) of the cells, at two different magnifications (length bars 100 μm and 20 μm). The right photomicrographs show immunohistochemistry detection of these cells for expression of CD59 and localization on the cell membrane. A substantial amount or possibly all of the cells were found to express CD59 protein. FIG. 1 panel C (right) is a set of photomicrographs of control cells (contacted with control vector AdCAGGFP) treated as in the left photomicrographs. These data show that CD59 was not expressed in these cells.

FIG. 2 panel A is a line graph showing percent of lysis of control cells not contacted with vector, on the ordinate, as a function of concentration of serum (normal human serum, herein NHS), on the abscissa, which cells were incubated. Lysis of untreated control cells was observed to be a function of serum concentration during the incubation. The lowest serum concentration that yielded maximal cell lysis was 1% (1/100 dilution; cell lysis was 96.06%±0.87%). This serum concentration was used in subsequent Examples herein.

FIG. 2 panels B, C, and D are printouts of cell sorting data showing results of human serum cell lysis assays with extent of propidium iodide (PI) labeling of cells shown on the abscissa (acquired in the FL3-H channel) and the number of cells on the ordinate. FIG. 2 panel B shows that in untreated cells (labeled uninfected), the cells treated with HI-NHS sorted to a location of lesser PI uptake cells treated with NHS (greater PI uptake). FIG. 2 panel C shows that cells contacted with AdCAGGFP vector were sorted similarly as untreated cells. FIG. 2 panel D shows that substantially all of the cells treated with vector AdCAGCD59 were sorted to the same position as those treated with heat inactivated NHS (HI-NHS), i.e., susceptibility to NHS was substantially or even entirely decreased by pretreatment with AdCAGCD59. In this example, PI is preferentially taken up by non-living cells, viz., the peak on the right. Cells contacted with the AdCAGCD59 vector were significantly protected, i.e., reducing complement mediated cell lysis to 12.29%±0.18%. FIG. 2 panel C shows that mouse cells contacted with the control vector (AdCAGGFP) were susceptible to cell lysis due to human serum complement (cell lysis was 95.27%±0.01%). Similarly, FIG. 2 panel B shows that control cells not contacted with vector were susceptible to human complement and cell lysis. These data show that cells were protected from lysis due to expression of human CD59 from the AdCAGCD59 vector, rather than from contact with an adenovirus vector.

FIG. 2 panel E is a bar graph comparing percent cell lysis (ordinate) of different groups of cells on the abscissa: control cells (not contacted with vector), cells contacted with control vector AdCAGGFP, and cells contacted with AdCAGCD59. Each bar represents a different treatment sample of the cells. The data in this graph show that cells contacted with AdCAGCD59 vector were significantly protected, as complement mediated cell lysis was 12.29%±0.18% (right bar). Cells treated with the control vector AdCAGGFP were susceptible to human complement with cell lysis of 95.27%±0.01% (middle bar). Untreated cells were susceptible to human complement and cell lysis (also about 95% cell lysis; left bar). These data show that human CD59 pretreatment of cells with AdCAGCD59 vector protected the cells from lysis.

FIG. 2 panel F is a line graph showing percent cell lysis (ordinate) of contacted cells as a function of multiplicity (vector particles/cell of pretreatment; abscissa). In cells contacted with AdCAGCD59 vector, cell lysis decreased with increasing multiplicity. Treatment with 250 virus particles (vp/cell) resulted in inhibition of cell lysis by more than 50%. Cells contacted with the control vector showed complete lysis of cells even at highest multiplicities.

FIG. 3 panel A shows mouse cells on poly-D-lysine coated chamberslides incubated with 10% NHS at 37° C. for one to ten minutes and subsequently washed and fixed. The left photomicrographs are visualized by DIC at different magnifications (as indicated by bars of length 100 µm and 20 µm). The right photomicrographs show results of cells contacted with anti-MAC antibody and with DAPI at different magnifications (100 µm and 20 µm). DAPI is 4'-6-Diamidino-2-phenylindole, a compound that forms fluorescent complexes with natural double-stranded DNA. These photomicrographs show that incubation of cells with NHS for five minutes caused significant changes in cell morphology compared to control cells incubated with HI-NHS; cells lost their extensive cytoplasmic processes and became round and granular (FIG. 3 panel A, left photomicrographs) compared to cells treated with HI-NHS (FIG. 3 panel B, left photomicrographs). Immunocytochemical analysis using a monoclonal antibody directed to a neoepitope on the C5b-9 complex showed extensive membrane staining at the borders of cells treated with NHS confirming deposition of the MAC on these cells (FIG. 3 panel A) compared to control cells treated with HI-NHS (FIG. 3 panel B).

FIG. 3 panel B shows results of examples similar to that in FIG. 3 panel A, except using HI-NHS. The data show that the cells did not change morphology, i.e., the HI-NHS did not have the same deleterious effect on cells as NHS.

FIG. 3 panel C is a set of photomicrographs taken with DIC, in which the left photomicrograph shows cells contacted with NHS and then stained with trypan blue, and the right photomicrograph shows cells contacted with HI-NHS and then stained with trypan blue. Lysis of a substantial number of NHS treated cells was observed as determined by trypan blue staining (left); substantially no lysis was observed with HI-NHS contacted cells (right), as indicated by normal cell morphology and absence of trypan blue uptake (right). Further, cells treated with HI-NHS maintained normal cell morphology, while those exposed to NHS lost processes associated with normal cells. Images are representative of three independent experiments for each type of serum tested.

FIG. 4 panel B is a set of photomicrographs of another sample of cells contacted with the AdCAGCD59 vector expressing CD59 with the same experimental protocol as FIG. 4 panel A. In contrast to data in FIG. 4 panel A, cells contacted with the CD59 vector retained normal morphology, and were protected from MAC stain even after seven minutes of incubation with NHS. Images are representative of three independent experiments for each type of serum experiment.

FIG. 4 panel C is a set photomicrographs taken by DIC of cells contacted with AdCAGGFP and then stained with trypan blue (left), and cells contacted with AdCAGCD59 and then stained with trypan blue (right).

FIG. 4 panels A, B, and C show that contacting mouse hepa-1c1c7 cells with AdCAGCD59 vector significantly protected these cells from MAC deposition and lysis (FIG. 4 panel B and 4 panel C right photomicrograph). Cells contacted with CD59 expressing vector and then exposed to NHS for five minutes maintained normal healthy morphological characteristics (FIG. 4 panel B, upper row, middle photomicrograph and lower right photomicrograph). Cells contacted with the control adenovirus vector and expressing GFP were not protected against MAC deposition after five minutes of NHS treatment (FIG. 4 panel A). Abnormal morphological changes were observed in these cells including loss of cytoplasmic processes and round and granular shape (FIG. 4 panel A, upper row, middle and lower right photomicrographs). MAC immunostaining was observed (FIG. 4 panel A, middle row, middle and lower right photomicrographs), and lysis of a substantial amount of control cells was observed by trypan blue staining (FIG. 4 panel C, left photomicrograph). These photomicrographs further show a small extent of MAC staining in some AdCAGCD59 contacted cells after seven minutes of NHS treatment (FIG. 4 panel B, middle row, right photograph). Control cells contacted with AdCAGGFP after seven minutes of NHS treatment, MAC staining was significantly stronger (FIG. 4 panel A, middle row, right photomicrograph) than in cells treated with AdCAGCD59 (FIG. 4 panel B, middle row, right photomicrograph).

FIG. 5 shows the inverse relationship between human MAC deposition and amount of adCAGCD59 adenovirus used to pretreat cells.

FIG. 6 panel A (left) shows human MAC deposition immunochemistry data obtained from eyecup tissues (dissected to a flat surface, length bar 1 mm) contacted for 15 minutes with an anti-emmprin antibody then by 50% NHS. Photomicrographs 1-3 (right) show two magnifications (length bars 100 and 400 µm) of the dissected cells. Extensive MAC immunostaining of eyecup cells was observed, and the RPE monolayer of these eyecups appeared convoluted and various patterns of staining were observed.

FIG. 6 panel B shows data as in FIG. 6 panel A, however were contacted with HI-NHS for 15 minutes instead of NHS. No MAC immunostaining on the RPE of the murine eyecups was observed compared to extensive immunostaining observed of cells incubated with NHS (FIG. 6 panel A).

FIG. 6 panel C shows data as in FIG. 6 panels A and B, however incubated with 100% NHS for 60 minutes at 37°

C., and not contacted anti-emmprin antibody before the addition of the NHS. Data show staining was occasional, scattered and weak.

FIG. 6 panel D shows primary murine RPE cells analyzed by human MAC immunochemistry results, DIC, and DAPI for cells contacted with an anti-emmprin antibody followed by NHS for seven minutes. Cells are shown at two different magnifications (as indicated by bars of length of 300 μm and 75 μm). Extensive MAC immunostaining was observed for RPE cells as was observed for eyecups (FIG. 6 panel B).

FIG. 6 panel E shows results for primary murine RPE cells as in FIG. 6 panel D but with HI-NHS for 7 minutes at 37° C. Less extensive MAC immunostaining was observed than in cells incubated with NHS (FIG. 6 panel D).

Figure 7:
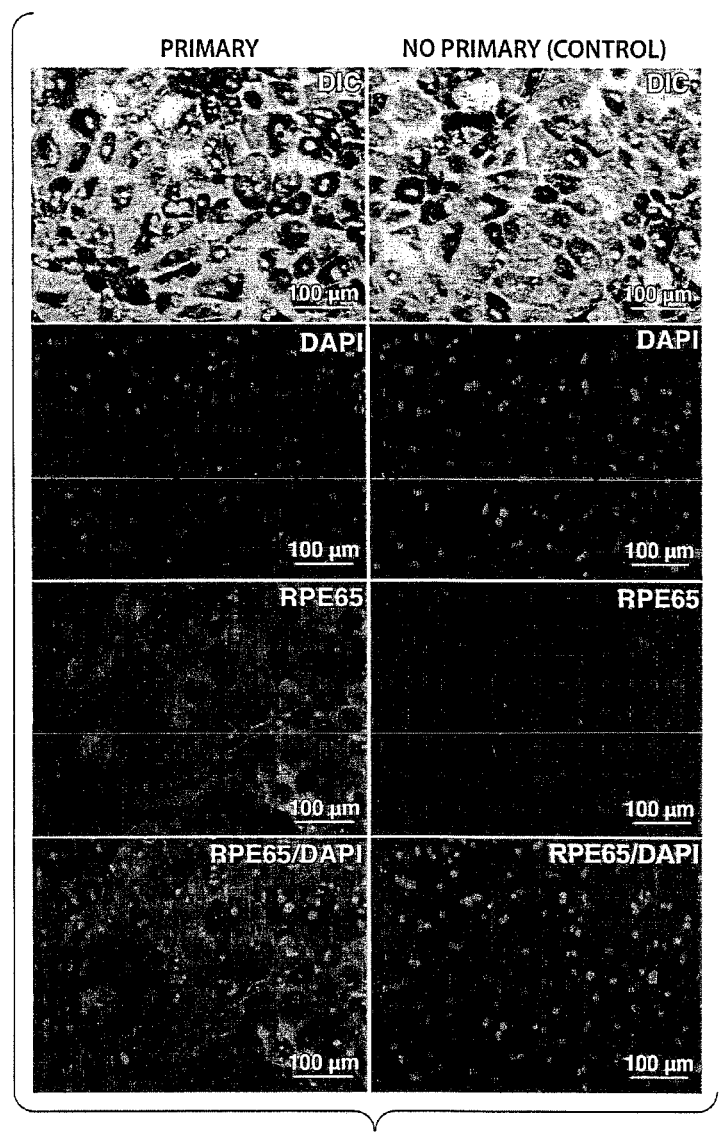
Figure 9A:
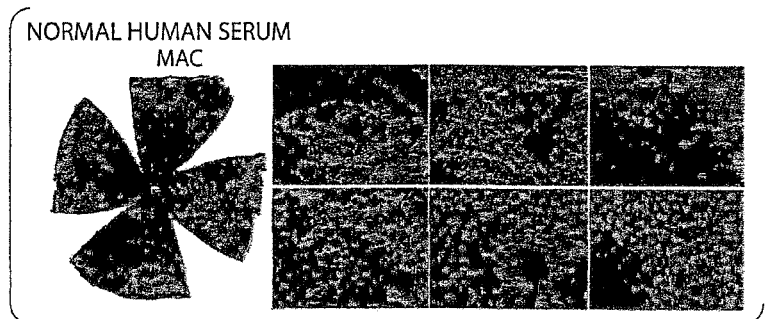
Figure 9B:
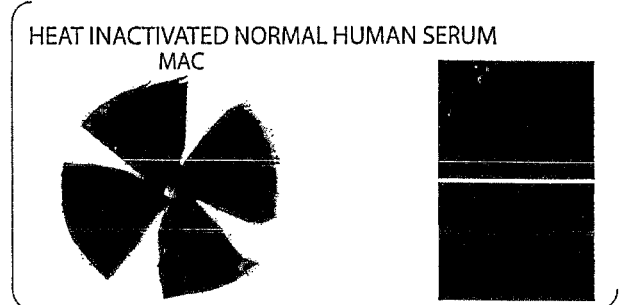
Figure 9C:
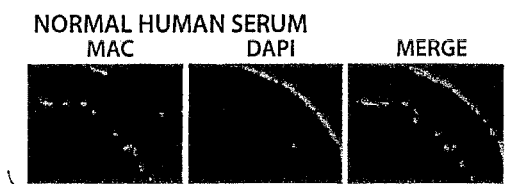
Figure 9D:
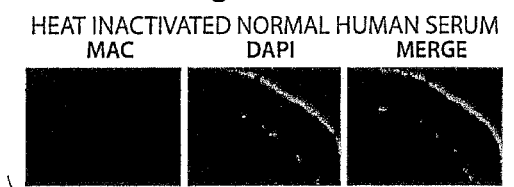

FIG. 7 is a set of photomicrographs showing of RPE cells tested analyzed with a double antibody assay using anti-mouse RPE65 antibody (indicated RPE65 in the figure, third row) visualized by an appropriate Cy3-conjugated secondary antibody. The column on the left shows photomicrographs of cells stained with anti-mouse RPE65 antibody (Primary). The column on the right shows photomicrographs of control cells not contacted with the primary anti-RPE65 antibody and further treated with secondary antibody, indicated in the figure as No Primary (Control). Cells were visualized by each of DIC, DAPI, and by superimposing the RPE65 and DAPI staining (indicated RPE65/DAPI, fourth row).

FIG. 8 is a set of photomicrographs showing data obtained by contacting RPE cells with anti-emmprin antibody and 50% NHS for four minutes (FIG. 8 panel A, left column), or contacting RPE cells with the anti-emmprin antibody and 50% NHS for seven minutes (FIG. 8 panel A, right column), or contacting RPE cells with the anti-emmprin antibody and 50% HI-NHS for seven minutes (FIG. 8 panel B), or contacting RPE cells with 50% NHS alone for seven minutes (control; FIG. 8 panel C). Top row: cells visualized by BF; second row: cells stained with DAPI; third row: cells contacted with anti-human C5b-9 antibody; and fourth row: merges/overlay of the DAN and antibody second and third row results.

FIG. 8 panel A shows extensive MAC immunostaining on the RPE cells treated with the anti-emmprin antibody and 50% NHS for four minutes (left column, third row), and after seven minutes of NHS treatment. It was observed that a substantial amount/number of RPE cells have detached from the slide (right column, third row). FIG. 8 panel A shows that cell aggregates of high confluence areas occasionally remained and that these areas are strongly positive for MAC (left and right columns, third row).

FIG. 8 panel B shows that HI-NHS treated cells did not bind to anti-MAC antibody (third row).

FIG. 9 is a set of photographs showing mouse eyecup tissues and photomicrographs of mouse cornea tissues.

FIG. 9 panel A shows results for eyecup tissues (dissected to present a flat surface) contacted with an anti-mouse emmprin antibody followed by addition of NHS (final concentration 50% for 15 minutes at 37° C.). After exposure to NHS, RPE monolayer appeared convoluted and displayed various patterns of staining due to different amounts of MAC deposition and various amounts of cell damage.

FIG. 9 panel B shows results for eyecup tissues contacted with an anti-mouse emmprin antibody followed by addition of HI-NHS (final concentration 50% for 15 minutes at 37° C.). Cells contacted with HI-NHS show absence of MAC immunostaining in RPE cells and corneal endothelium.

FIG. 9 panel C shows results for cornea tissues contacted with an anti-mouse emmprin antibody followed by addition of NHS (final concentration 50% for 20 minutes at 37° C.). After exposure to NHS, RPE monolayer appeared convoluted and displayed various patterns of staining due to different amounts of MAC deposition and various amounts of cell damage.

FIG. 9 panel D shows sells contacted with HI-NHS show absence of MAC immunostaining in RPE cells and corneal endothelium.

Figure 10A:
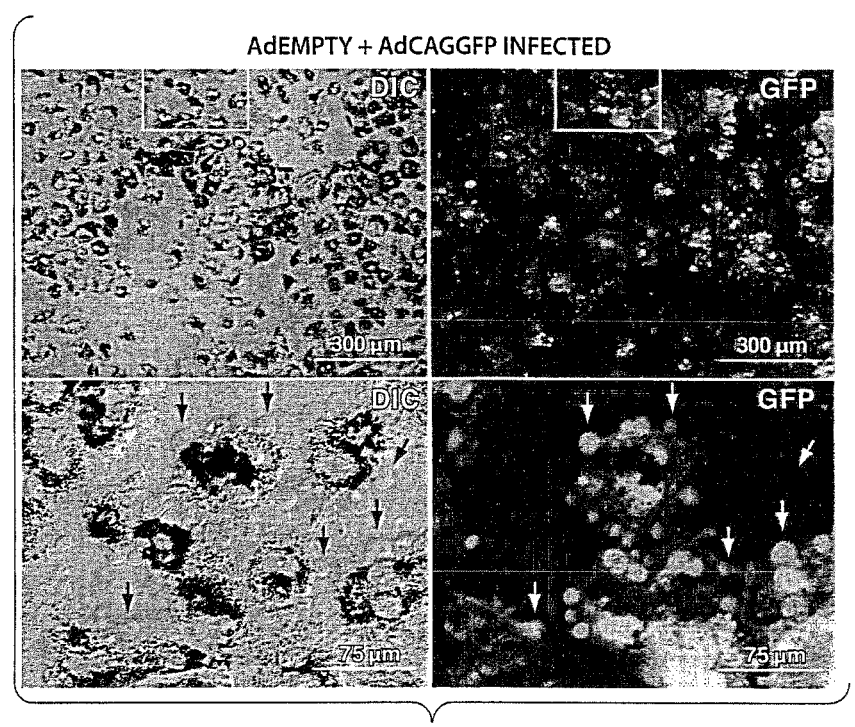
Figure 10B:
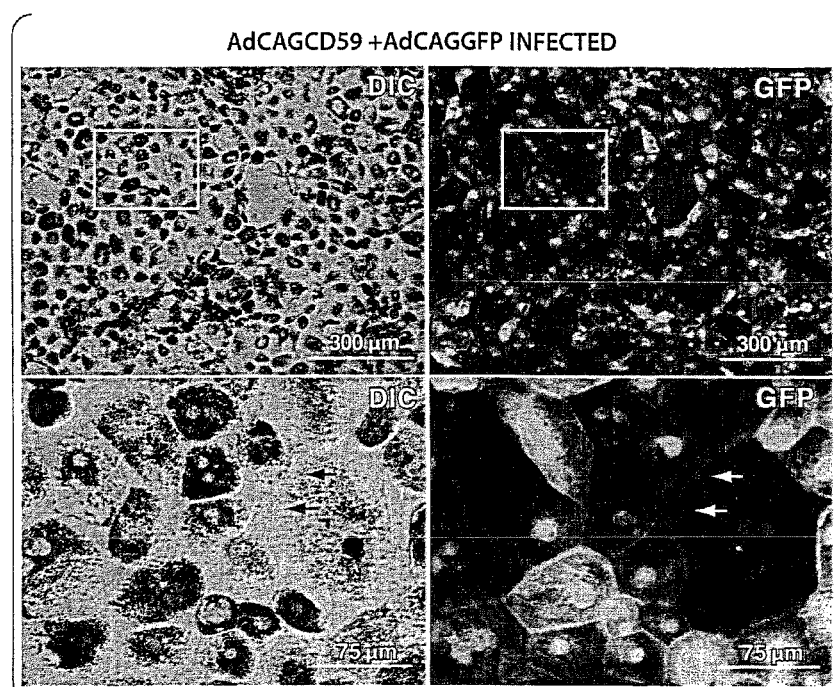
Figure 11A:
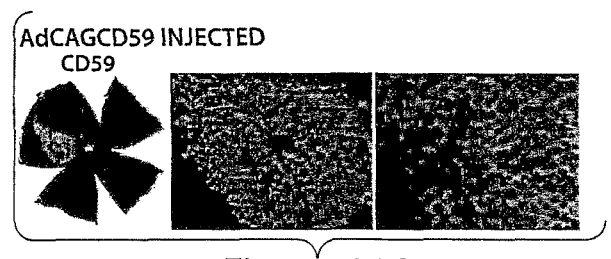
Figure 11B:
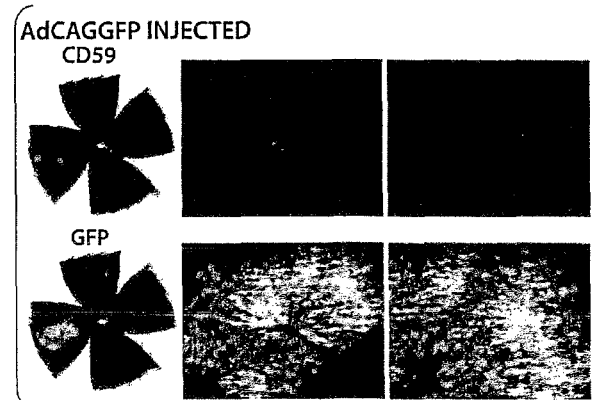
Figure 11C:
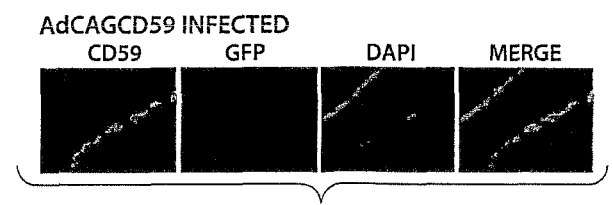
Figure 11D:
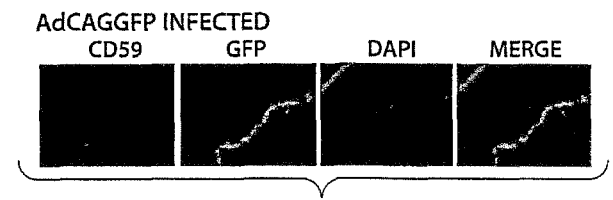
Figure 12A:
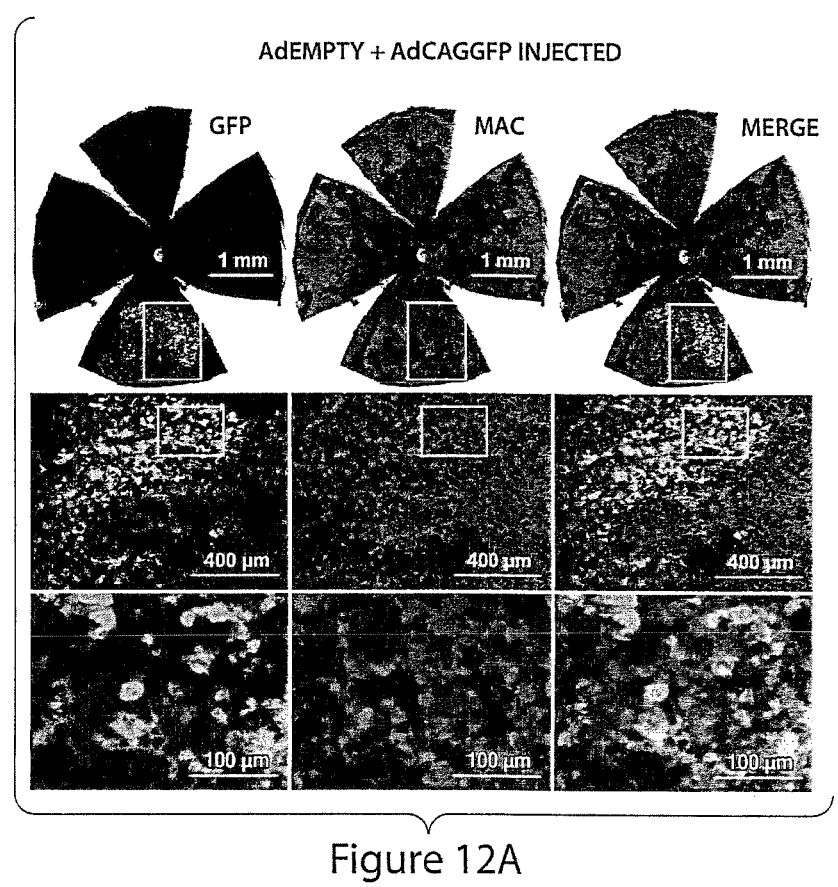
Figure 12B:
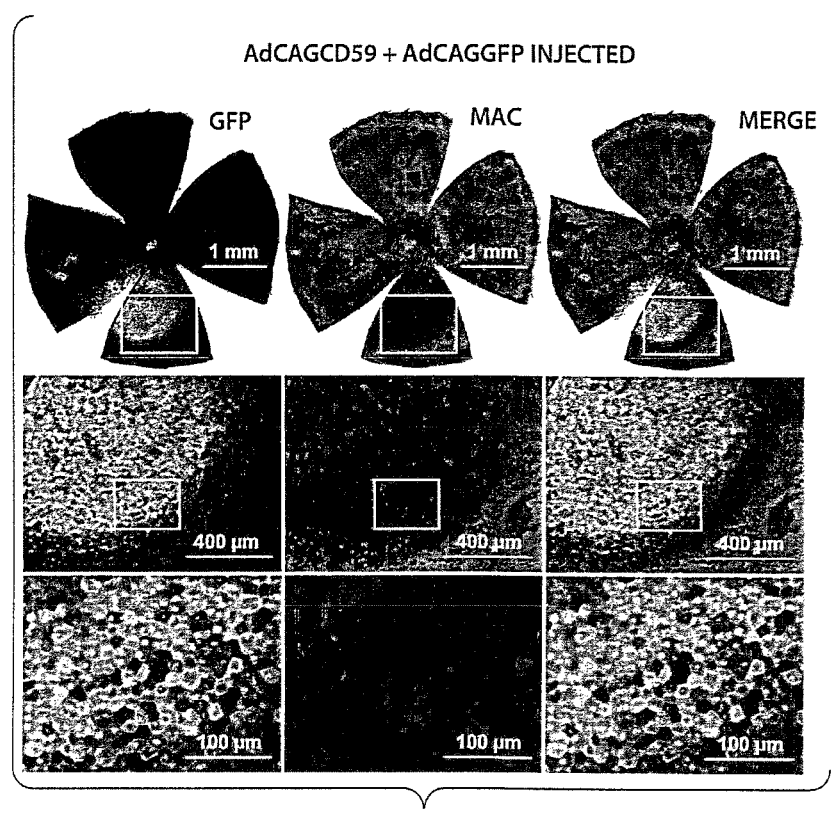
Figure 12C:
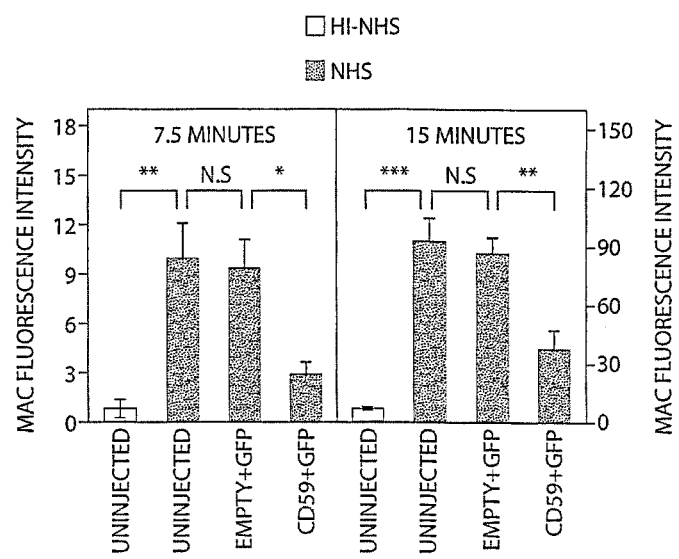
Figure 12D:
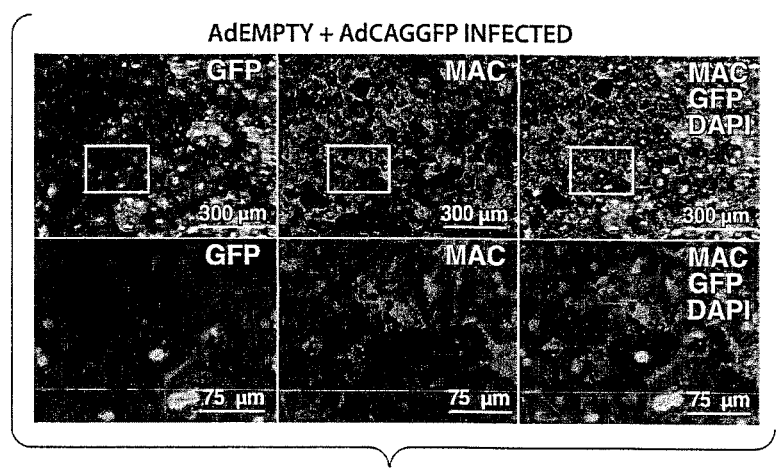
Figure 12E:
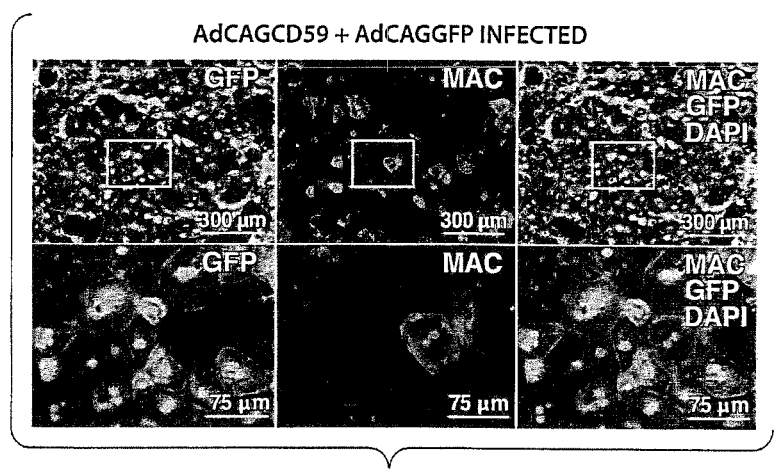

FIG. 10 is a set of photomicrographs of cells pre-treated with mixtures of control vectors and hCD59 expressing vectors.

FIG. 10 panel A shows primary mouse RPE cells pre-treated with a mixture of AdEMPTY+AdCAGGFP (4:1 ratio, total of 1×10³ vp/cell), then contacted three days post infection with anti-emmprin antibody and with 50% NHS for seven minutes after washings and fixation. Cells were observed with DIC (left) or by GFP fluorescence (right).

FIG. 10 panel B shows primary mouse RPE cells pre-treated as in FIG. 10 panel A except with a mixture of AdCAGCD59+AdCAGGFP (4:1 ratio, total of 1×10³/cell). Use of AdCAGGFP revealed vesicles (FIG. 10 panels A and B, arrows). The data show inhibition of MAC-associated vesiculation by adenovirus-mediated delivery of hCD59.

FIG. 11 is a set of photographs of dissected tissues, and a set of photomicrographs of these tissues to analyze cell data.

FIG. 11 panel A shows eyecup tissues pre-treated for six days by subretinal injection of either AdCAGCD59. Tissues were stained by immunohistochemistry for expression of CD59, and tissue fluorescence of GFP was detected directly. FIG. 11 panel B shows eyecup tissues as in FIG. 11 panel A, except pre-treated with control vector AdCAGGFP. FIG. 11 panel C shows cornea tissues were harvested from mice and pre-treated ex vivo for three days with either AdCAGCD59. FIG. 11 panel D shows cornea tissues as in FIG. 11 panel C except pre-treated with control vector AdCAGGFP.

Data from FIG. 11 panels A and C show expression of human CD59 by murine RPE and corneal endothelium following pre-treatment with AdCAGCD59. AdCAGCD59 and AdCAGGFP pre-treated corneas visualized with anti-CD59 antibody.

FIG. 12 is a set of photographs, photomicrographs and a bar graph of data from flatmounts of eyecups from eyes contacted by injection with a mixture of control vectors AdEMPTY+AdCAGGFP (9:1 ratio, 3×10⁸ vp/cell), in FIG. 12 panel A, and vectors AdCAGCD59+AdCAGGFP in FIG. 12 panel B (9:1 ratio, 3×10⁸ vp/cell). Cells were contacted six days post-injection with the anti-mouse emmprin antibody followed by 50% NHS for 15 minutes. GFP (left in each set) shows fluorescence at the site of injection (1 mm length bar), and photomicrographs below are two magnifications of the site of injection (length bars 400 μm and 100 μm). MAC shows MAC staining with anti-human C5b-9 antibody, with photomicrographs below magnifications of the site of injection (as indicated by bars of length of 400 μm and 100 μm). Merge is an overlay of the GFP and the MAC dissected tissue photographs (1 mm magnification).

FIG. 12 panels A and B data show that MAC immunostaining of control tissues contacted with a mixture of control vectors is substantial, and that MAC in control cells was significantly more extensive and stronger than the MAC at the area of GFP expression in tissues receiving injection of the mixture of AdCAGCD59 and AdCAGGFP (FIG. 12 panel B). RPE cells at the GFP expressing area of control injected eyecups were observed to be extensively damaged as indicated by rounded shape, loss of normal hexagonal morphology and loss of defined cell boundaries (FIG. 12 panel A middle row).

FIG. 12 panel B show that human MAC deposition was significantly reduced on the RPE at the area of GFP expression, correlating with human CD59 expression compared to the rest of the eyecup tissue. RPE cells in this area were observed to be undamaged with defined cell boundaries and normal hexagonal morphology.

FIG. 12 panel C graphs show eyecup tissues contacted with serum for either 7.5 minutes (left graph) or 15 minutes (right graph). Serum was HI-NHS (open bars) or NHS (closed bars). The four types of tissues: uninjected/not contacted with adenovirus and contacted with HI-NHS (Uninjected, open bar first from the left), uninjected/not contacted with adenovirus and contacted with NHS (Uninjected, closed bar second from left), tissues injected with a mixture of control adenovirus and contacted with NHS (EMPTY+GFP, closed bar second from the right), tissues injected with a mixture of AdCAGCD59+AdCAGGFP adenovirus and contacted with NHS (CD59+GFP, closed bar first from the right). Data expressed as means±s.e.m. *p<0.01, p<0.001, *p<0.0001 show at both treatment periods that CD59 contacted cells had lower levels of MAC.

FIG. 12 panel D is a set of photomicrographs of primary RPE cells injected with a mixture of control vectors (AdEMPTY +AdCAGGFP), then treated with the anti-mouse emmprin antibody followed by 50% NHS for 15 minutes at 37° C. six days post-injection. Images are representative of three separate experiments.

FIG. 12 panel E shows primary RPE cells as in FIG. 12 panel D but injected with a mixture of hCD59 expressing vectors (AdCAGCD59+AdCAGGFP). Significantly less MAC deposition was observed than in comparable cells in FIG. 12 panel D.

Figure 13A:
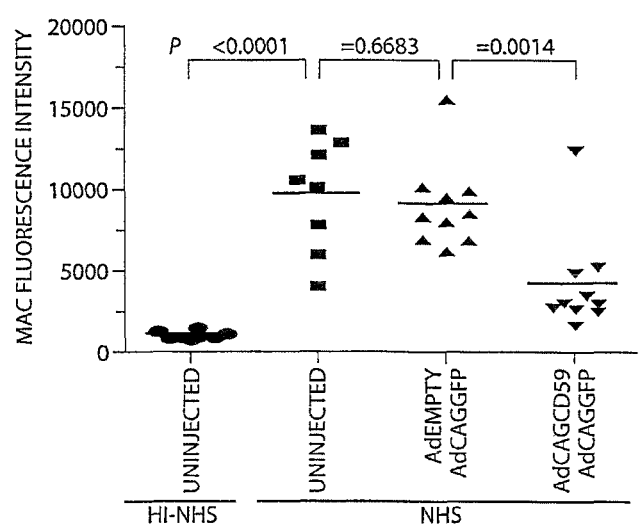
Figure 13B:
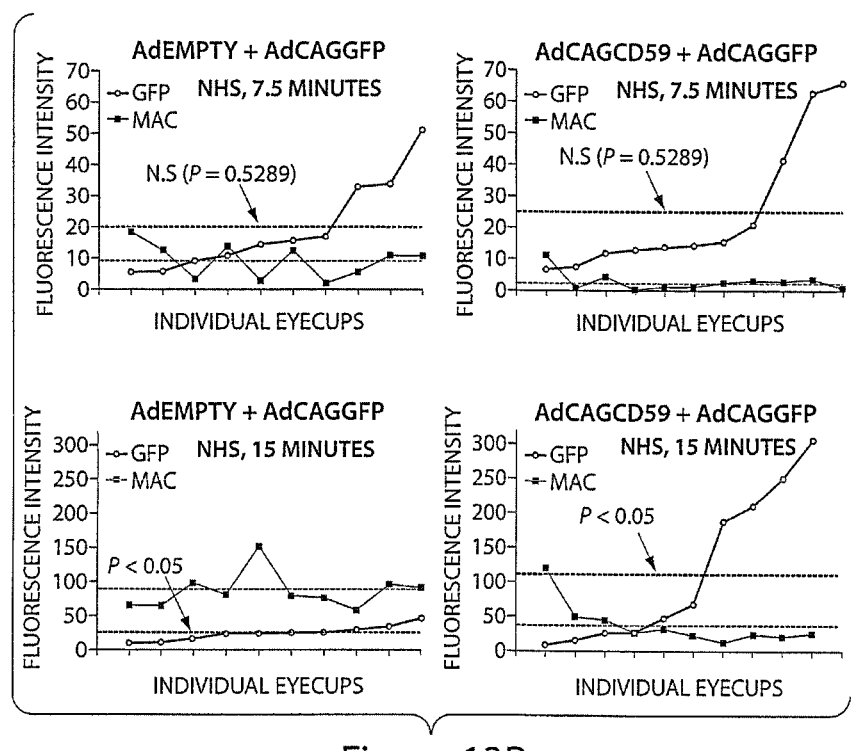
Figure 14A:
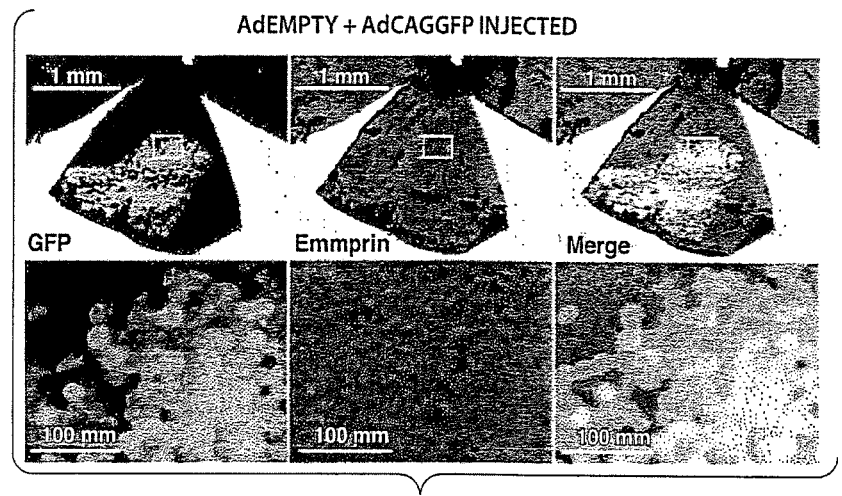
Figure 14B:
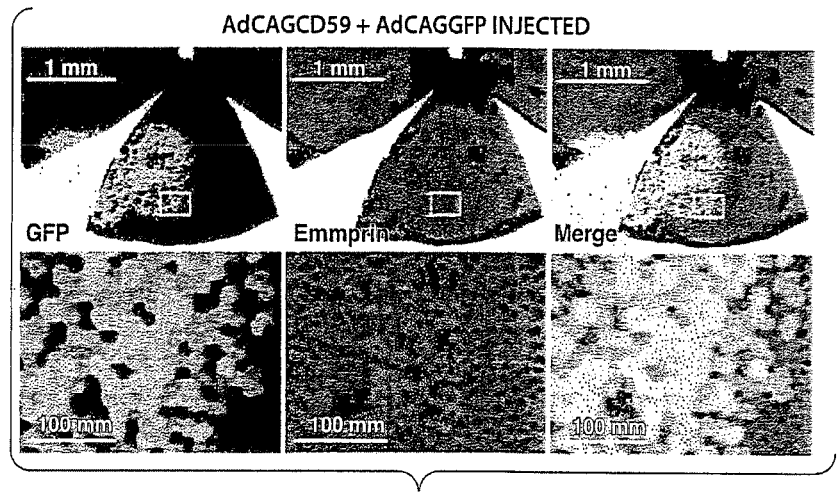
Figure 14C:
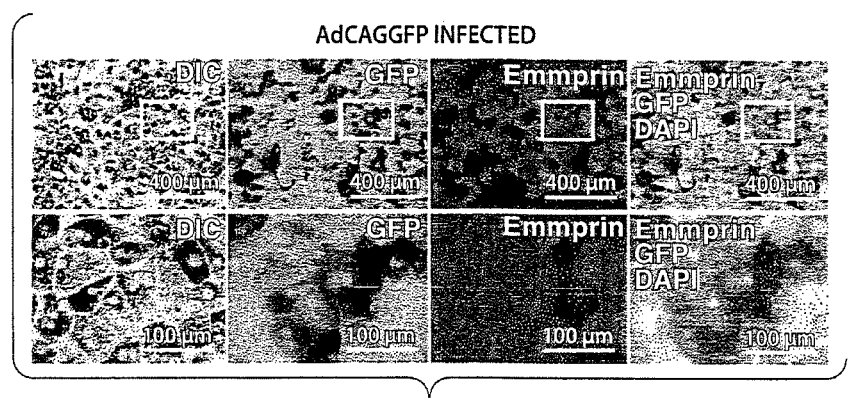
Figure 14D:
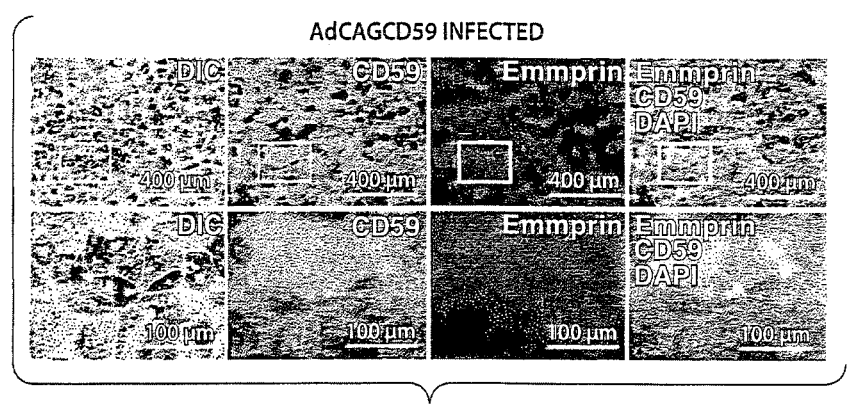

FIG. 13 panel A is a graph showing quantification of the MAC immunofluorescence at the area of GFP expression with MAC fluorescence intensity on the ordinate and nature of injected material to which RPE cells were contacted on the abscissa. Control cells contacted with NHS have a MAC fluorescence intensity between 5,000 and 15,000, with a median of about 10,000. In contrast, control cells contacted with HI-NHS have a MAC fluorescence intensity of less than 2,500. RPE cells contacted with a mixture of AdEMPTY and AdCAGGFP and contacted with NHS have a MAC fluorescence intensity between 6,000 and 10,000, with a median of about 9,000. RPE cells contacted with a mixture of AdCAGCD59 and AdCAGGFP and contacted with NHS have a MAC fluorescence intensity between 2,000 and 1 1,000, with a median less than 5,000 due to one out-lying point. This data show an overall reduction of about 55% in mean MAC fluorescence intensity for AdCAGCD59 and AdCAGGFP injected eyecup tissues (n=10) compared to control injected eyecup tissues (n=10), which was statistically significant (p=0.0014, FIG. 13 panel A).

FIG. 13 panel B is a set of line graphs of quantification of fluorescence intensity at the site of injection (ordinate) of individual eyecup tissues (abscissa). Both GFP fluorescence and MAC immunofluorescence intensity at the area of GFP expression are shown for eyecups from eyes injected with mixtures of control (AdEMPTY+AdCAGGFP, left) vectors or hCD59 expressing vector (AdCAGCD59+AdCAGGFP, right). Length of serum treatment (7.5 minutes, top row; 15 minutes, bottom row) is indicated on each photomicrograph. The data points are the GFP or MAC fluorescence intensity from one eyecup, arranged from left to right in the order of increasing GFP fluorescence intensity. Lines are the means for each set of data. An inverse relationship was observed between GFP and MAC fluorescence intensities on the AdCAGCD59+AdCAGGFP—contacted eyecups contacted with NHS. The symbol N.S. signifies that the differences are not statistically significant.

FIG. 14 is a set of photomicrographs showing immunochemistry data for RPE cells contacted with control mixture of AdEMPTY and AdCAGGFP (FIG. 14 panel A) or a mixture of AdCAGCD59 and AdCAGGFP (FIG. 14 panel B). Six days post-infection with the indicated adenovirus mixtures, cells were contacted with first primary goat anti-mouse emmprin antibody followed by first secondary Cy3-conjugated donkey anti-goat IgG antibody. GFP shows fluorescence at the site of injection, and below are two magnifications at site of injection. Emmprin shows emmprin immunofluorescence, and two magnifications at the site of injection. Merge is an overlay of the GFP and the emmprin. Images are representative of three separate experiments. Data in FIG. 14 panels A and B show no significant difference in emmprin iummnofluoresence between the area of transgene expression and the rest of the eyecup or uninjected eyecups.

FIG. 14 panel C shows data for RPE cells contacted by injection with AdCAGGFP. Three days later cells were contacted with first primary goat anti-mouse emmprin antibody followed by first secondary Cy3-conjugated donkey anti-goat IgG antibody, washed, fixed, and were incubated with the second primary-mouse anti-hCD59 antibody followed by second secondary-Cy2-conjugated goat anti-mouse IgG antibody. Cell nuclei were labeled with DAPI and visualized by DIC, GFP, and Emmprin. Images are representative of three separate experiments.

FIG. 14 panel D shows results for RPE cells injected as in FIG. 14 panel C except with AdCAGCD59, and immunochemistry was observed as above. Data in FIG. 14 panels C and D show that no significant change in emmprin was observed due to expression of hCH59 (compared to GFP).

Figure 15:
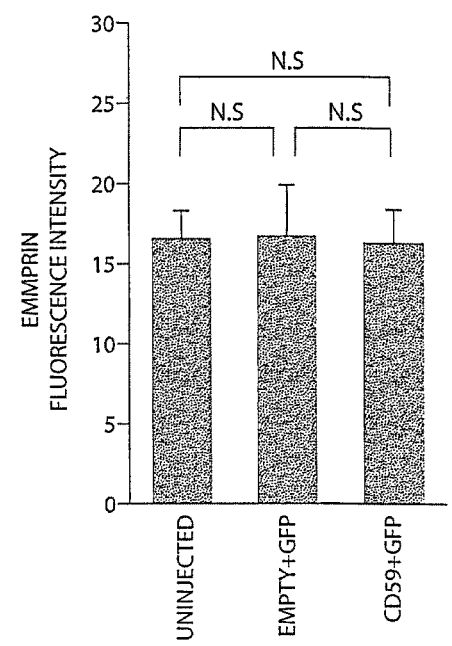

FIG. 15 is a bar graph showing emmprin immunofluorescence (ordinate) by RPE cells that were contacted with vectors (as shown on the abscissa) before emmprin immunostaining. The RPE cells shown were control not contacted (left bar), contacted with a mixture of control vectors (EMPTY+AdCAGGFP; middle bar), and a mixture of hCD59 expressing vector and GFP (CD59+GFP, right bar). For each group, twelve images (acquired with a 40X× objective) from three eyecups were quantified. Graph includes data obtained from experiments shown in FIG. 14 panels A and B. Data are expressed as means±s.e.m. The data show that there was no effect on emmprin staining by the pretreatments.

Figure 16:
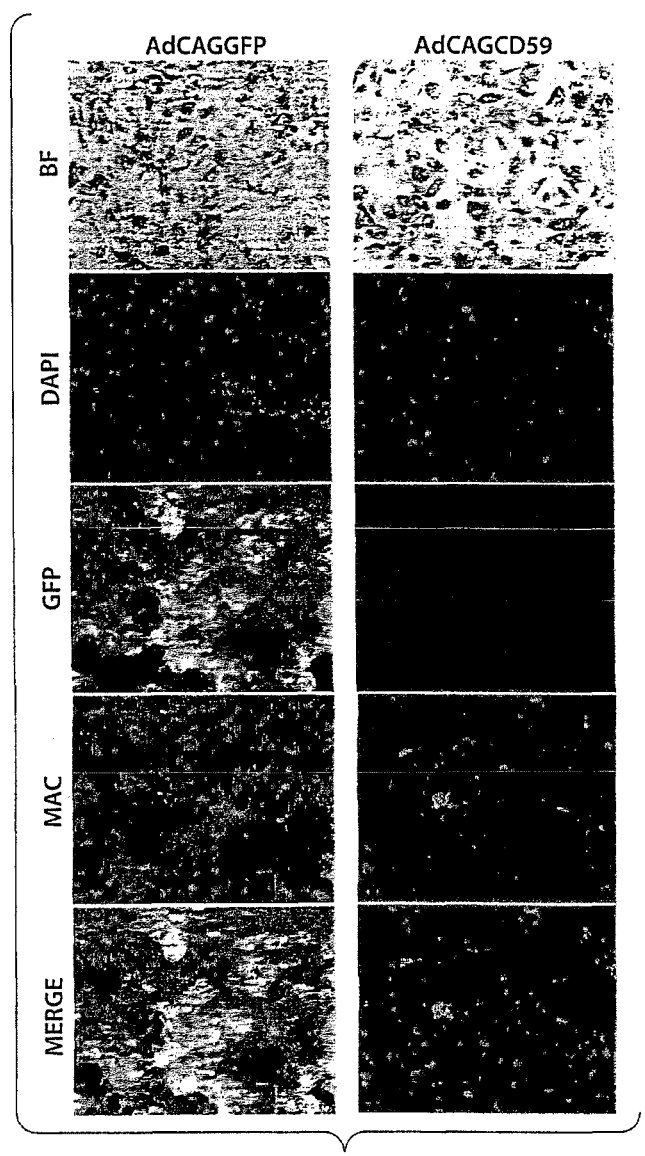
Figure 17A:
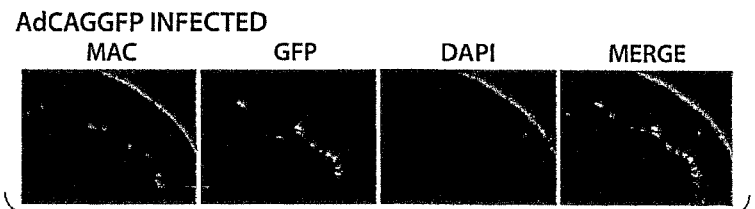
Figure 17B:
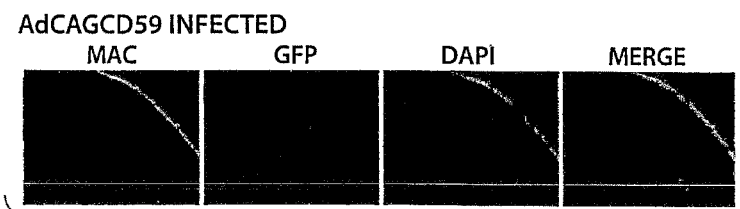
Figure 17C:
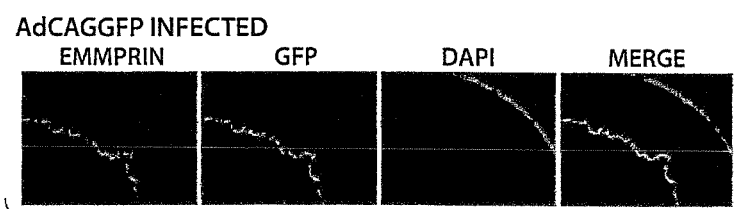
Figure 17D:
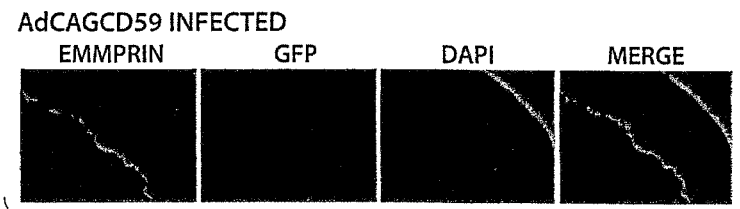
Figure 18A:
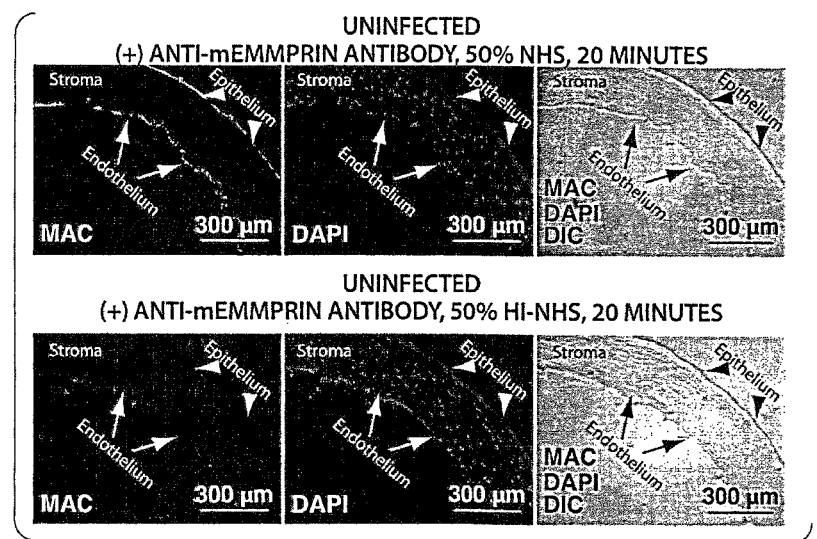
Figure 18B:
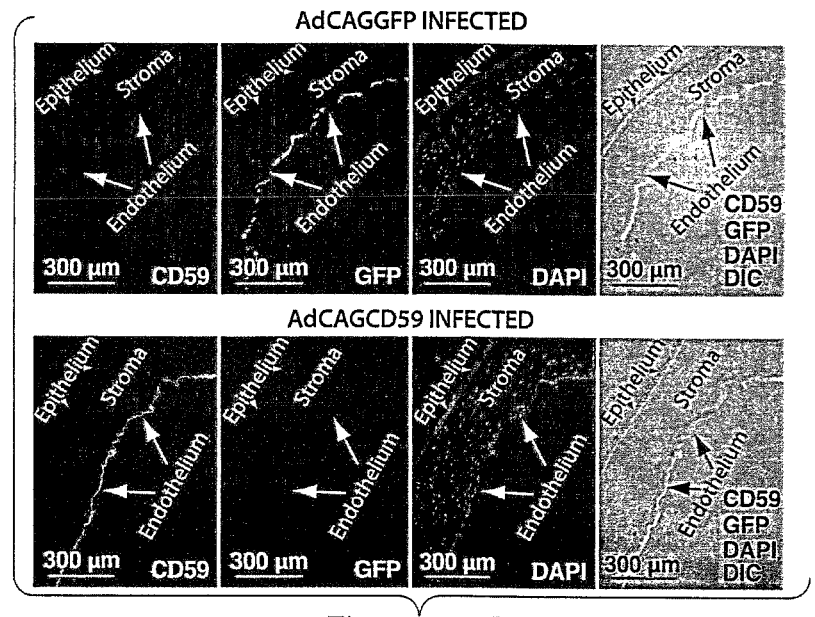
Figure 18C:
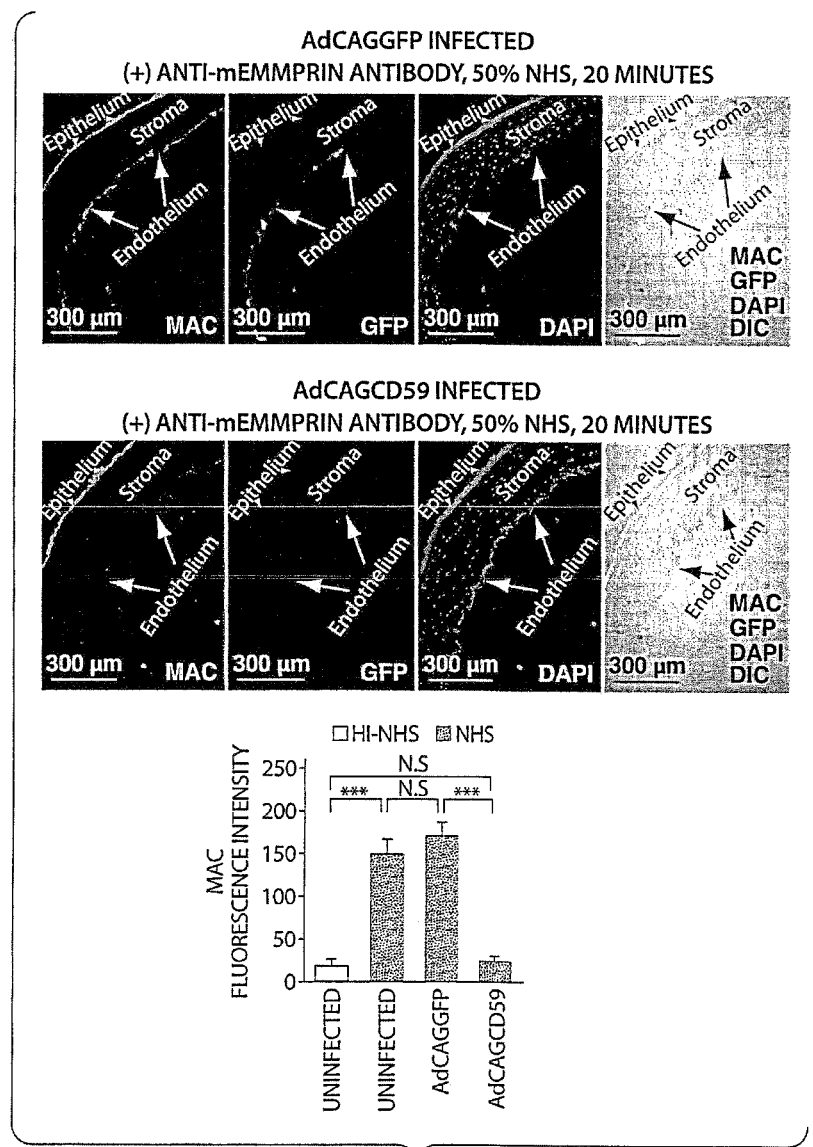
Figure 18D:
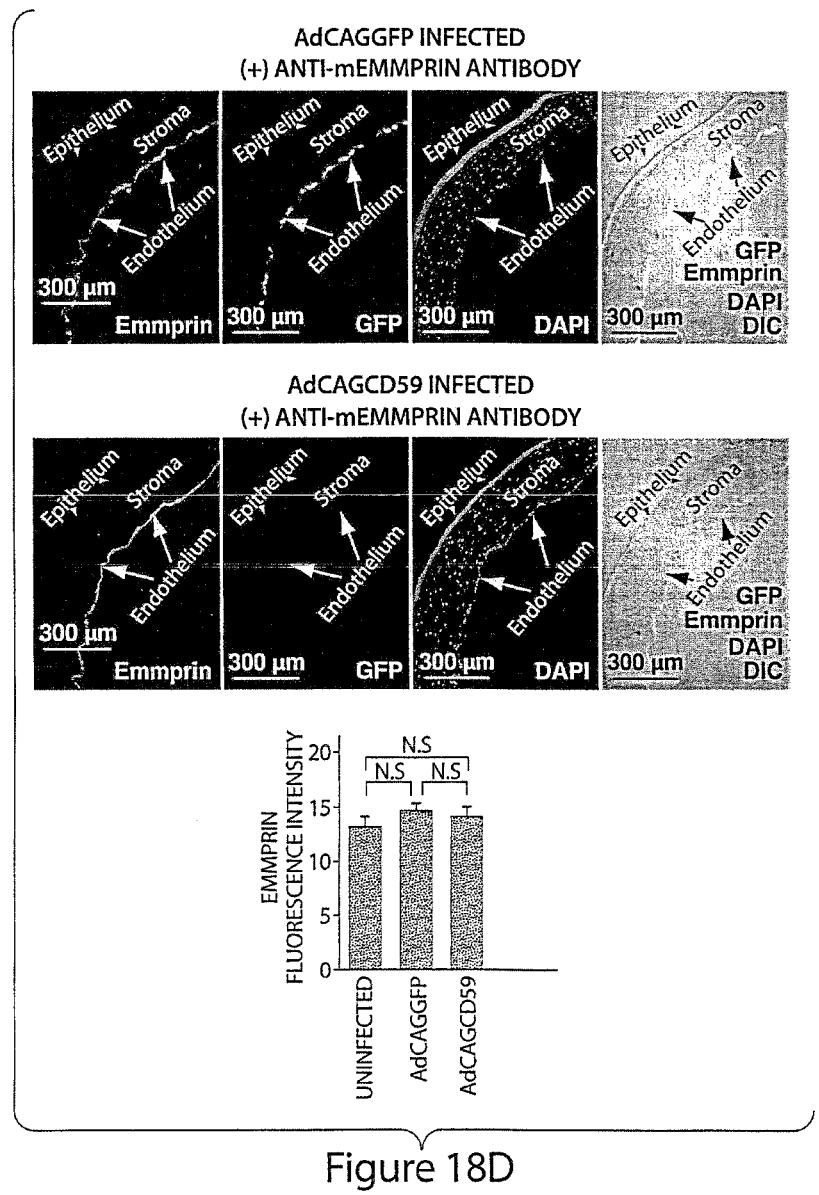

FIG. 16 is a set of photographs of primary mouse RPE cells three days after pretreatment. RPE cells were contacted with AdCAGGFP (left column) or with AdCAGCD59 (right column). Pigmentation of RPE cells contacted with AdCAGGFP (BF photograph, left column) was observed to be similar to pigmentation of cells contacted with AdCAGCD59 (BF photograph, right column). RPE cells contacted with AdCAGGFP and stained with DAN showed the same amount of fluorescence (DAPI photograph, left column) compared to RPE cells contacted with AdCAGCD59 and stained with DAPI (DAPI photograph, right column). RPE cells contacted with AdCAGGFP showed significantly greater green fluorescence (GFP photograph, left column) compared to RPE cells contacted with AdCAGCD59 (GFP photograph, right column). RPE cells contacted with AdCAGGFP followed by anti-mouse emmprin antibody and NHS showed significantly greater MAC immunofluorescence (MAC photograph, left column) compared to RPE cells contacted with AdCAGCD59 followed by the same anti-mouse emmprin and NHS treatment and detected by anti-human MAC antibody (MAC photograph, right column).

FIG. 17 is a set of photomicrographs that show that protection from MAC on the corneal endothelium of AdCAGCD59 contacted corneas (FIG. 17 panels B and D) was not due to a difference in emmprin expression or anti-emmprin antibody binding, as immunohistochemistry showed no differences in emmprin immunostaining of the corneal endothelium between AdCAGCD59 and AdCAG-GFP contacted corneas (FIG. 17 panel C, emmprin photograph compared to FIG. 17 panel D, emmprin photograph). These photographs further show significant reduction in MAC immunostaining on the corneal endothelium of AdCAGCD59 contacted corneas (FIG. 17 panel B, MAC photograph) compared to MAC immunostaining on the corneal endothelium of AdCAGGFP contacted corneas (FIG. 17 panel A, MAC photograph).

FIG. 17 panel A is a set of photographs showing a section from a cornea contacted with a control AdCAGGFP and followed by anti-mouse emmprin antibody and NHS. The photograph labeled MAC shows MAC immunostaining with anti-MAC antibody on the endothelium of this cornea. The photograph labeled GFP shows GFP fluorescence on the corneal endothelium. The photograph labeled DAN shows labeled DNA fluorescence of the corneal cells. The photograph labeled merge shows an overlay of the previous photographs.

FIG. 17 panel B is a set of photographs showing cells contacted with AdCAGCD59 followed by the same anti-mouse emmprin and NHS treatment as the cornea in FIG. 17 panel A. The photograph labeled MAC shows MAC immunostaining on the endothelium of this cornea. The photograph labeled GFP shows absence of GFP fluorescence by these cells. The photograph labeled DAPI shows labeled DNA fluorescence of the corneal cells. The photograph labeled merge shows an overlay of the previous photographs.

FIG. 17 panel C is a set of photographs showing cells contacted with a control AdCAGGFP. The photograph labeled emmprin shows emmprin antibody immunostaining of these cells. The photograph labeled GFP shows direct GFP fluorescence by these cells. The photograph labeled DAPI shows labeled DNA fluorescence of these cells. The photograph labeled merge shows an overlay of the previous photographs.

FIG. 17 panel D is a set of photographs showing cells contacted with AdCAGCD59. The photograph labeled emmprin shows emmprin antibody immunostaining of these cells. The photograph labeled GFP shows direct GFP fluorescence by these cells. The photograph labeled DAPI shows labeled DNA fluorescence of these cells. The photograph labeled merge shows an overlay of the previous photographs.

FIG. 18 is a set of photographs and bar graphs of corneas injected ex vivo with AdCAGGFP or AdCAGCD9 vectors and treated with or without emmprin antibody and NHS or HI-NHS, the bar graphs showing each of MAC and emmprin fluorescence intensity.

FIG. 18 panel A shows emmprin in control corneas not contacted with vector and contacted with anti-mouse emmprin antibody then with NHS (top row) or HI-NHS (bottom row). MAC staining (red in original not shown here), DAPI (blue in original) and DIC for these corneas were observed. Bright MAC immunostaining was observed on corneal endothelia of the corneas treated with NHS and minimal staining on the corneal endothelia treated with HI-NHS.

FIG. 18 panel B shows an immunohistochemical analysis similar to that in FIG. 18 panel A, but of corneas contacted for three days with AdCAGGFP or AdCAGCD59 adenovirus (top row and bottom row respectively, $1.5 \times 10^9$ vp). No CD59 expression was observed for the corneas contacted with the AdCAGGFP adenovirus (top), and strong CD59 expression was observed for corneas contacted with adCADCD59 adenovirus (bottom).

FIG. 18 panel C shows corneas contacted with AdCAG-GFP (top) or AdCAGCD59 (bottom) adenovirus, and contacted with 25 μg/ml goat anti-mouse emmprin antibody and with NHS (top row) or HI-NHS (bottom). The bar graph in FIG. 18 panel C shows quantification of MAC immunofluorescence (ordinate) on the corneal endothelium of twelve sections from four corneas groups in each group contacted with or without adenovirus (abscissa). The groups include: control (not contacted, indicated uninfected in the figure) corneas that were contacted with serum, (AdCAGGFP) corneas contacted with AdCAGGFP adenovirus before contact with serum, and (AdCAGCD59) corneas contacted with ADCAGCD59 adenovirus before contact with serum. The corneas groups were then exposed either to NHS (solid bars) or HI-NHS (open bars). Graph includes data shown in FIG. 18 panels A and C. Extensive MAC staining was observed for corneas contacted with AdCAGGFP adenovirus and contacted with NHS. ***$p<0.0001$, N.S., not significant. The data show that MAC in corneas contacted with CD59 was as low as that of control corneas.

FIG. 18 panel D shows corneas contacted with of AdCAGGFP (top row) or AdCAGCD59 (bottom row) adenovirus, and treated only with goat anti-mouse emmprin antibody. These corneas were not treated with NHS or HI-NHS as in FIG. 18 panel C. Emmprin expression, GFP fluorescence, DAPI and DIC staining are shown for these corneas at 300 μm magnification. The bar graph in FIG. 18 panel D shows quantification of MAC immunofluorescence (ordinate) on the corneal endothelium of twelve sections from four corneas groups in each group contacted with or without vectors (abscissa). The groups include: corneas not contacted with a vector before contact with NHS (indicated uninfected), corneas contacted with AdCAGGFP adenovirus before treatment with NHS, and (AdCAGCD59) corneas contacted with ADCAGCD59 adenovirus before treatment with NHS. The graph includes data from experiments shown in FIG. 18 panel D. Cell nuclei on all corneal sections were labeled with DAPI. All images are representative of sections obtained from four corneas for each group of infection or treatment. N.S., not significant. The data show no significant differences in emmprin among the groups of corneas.

Figure 19:
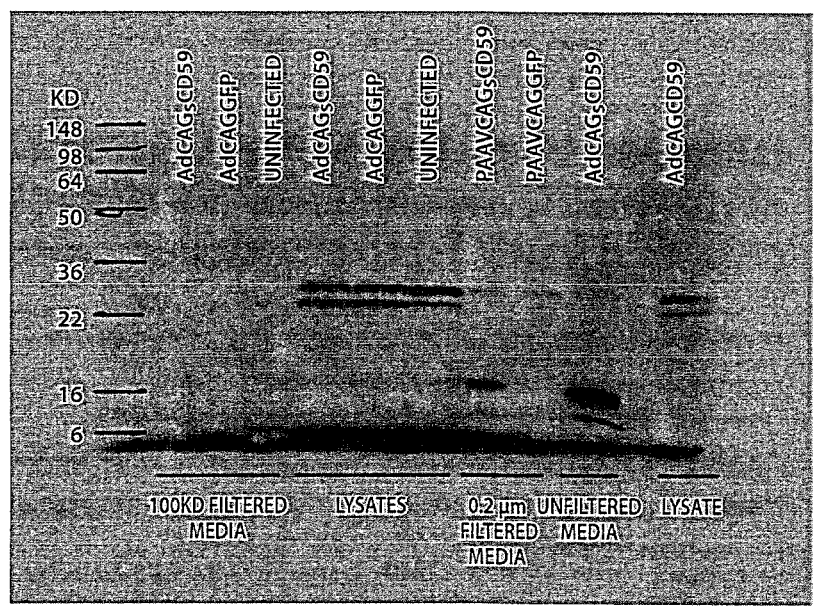

FIG. 19 is a photograph of a Western blot of cells contacted with vectors encoding human CD59 or control GFP as indicated. Samples were visualized with anti-CD59 antibody. Human CD59 was observed in unfiltered media from cells contacted with vector $AdCAG_sCD59$ (dark band at approximately 16 kD, second channel from the right indicated $AdCAG_sCD59$), a vector that expresses a soluble CD59 from which the glycosyl phosphatidyl inositol (GPI) linker was removed by recombinant deletion. $AdCAG_s$ CD59 thus was constructed to express a soluble secreted version of the CD59 construct used in examples above that encodes full-length membrane associated CD59 (Ad-CAGCD59/Lysate, first channel on the right). Molecular weight markers (6 to 148 KDa) are shown in the left channel. Cells were contacted with plasmids (indicated p) or adenovirus vectors (indicated Ad). Controls untreated cells received neither plasmids or vectors (indicated Uninjected), contacted with the membrane bound CD59 construct (CA- GCD59), or contacted with GFP expressing construct (CAGGFP). Samples were taken of media that were then filtered using a 100 kDa filter, or a 0.2 µm filter, or were unfiltered media, or were lysates. Control cells did not express CD59 (sixth channel from the left).

Figure 20A:
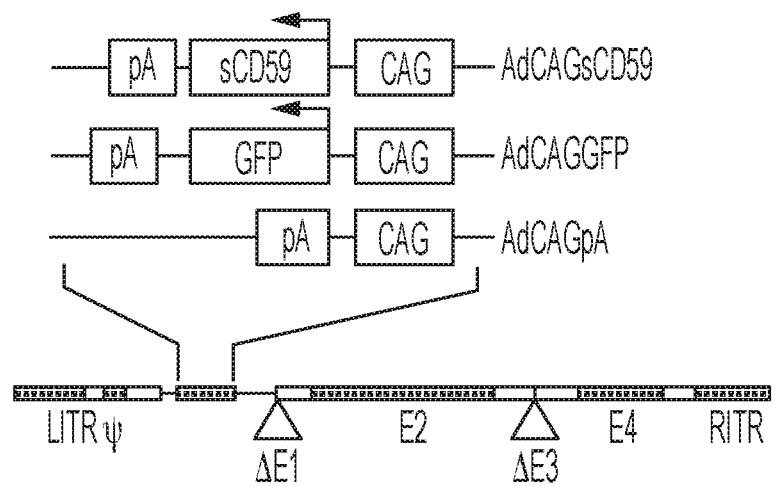
Figure 20B:
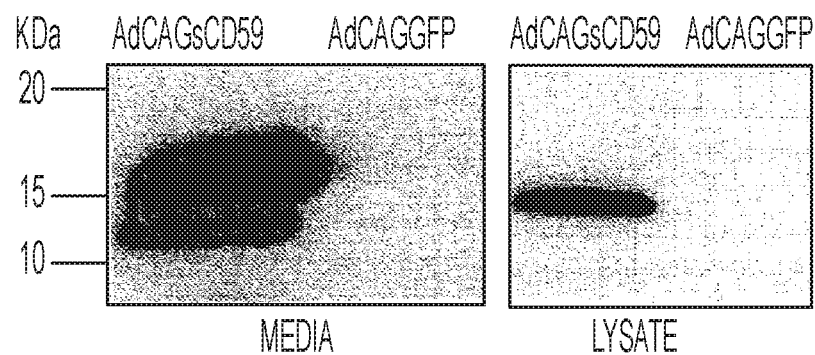

FIG. 20 is a drawing and set of photographs showing that sCD59 was expressed and efficiently secreted from adenovirus in vitro.

FIG. 20 panel A shows data obtained from constructs AdCAGsCD5p expressing human recombinant membrane-independent CD59 (sCD59), AdCAGGFP expressing GFP, and control AdCAGpA encoding neither CD59 nor GFP. Constructs were prepared by cloning each transgene into the deleted E1 region of an E1/E3-deleted adenovirus and is under control of the chicken β-actin promoter. Symbols: CAG, cytomegalovirus chicken β-actin β-globin promoter; Ψ, Ad packaging signal; LITR, adenovirus left inverted terminal repeat; Δ, deletion; E, early region labels; RITR, adenovirus right inverted terminal repeat.

FIG. 20 panel B is a set of photographs of Western blots of media (left photograph) and lysates (right photograph) obtained from ARPE-19 cells transfected with AdCAG-sCD59, an adenovirus vector expressing human sCD59. The photographs showed that secretion of the 14-17 kDa sCD59 protein into the media was substantial and was also detected in the cell lysates. An additional 11-13 kDa molecular weight band was detected in the media of the ARPE-19 cells transfected with AdCAGsCD59.

Figure 21A:
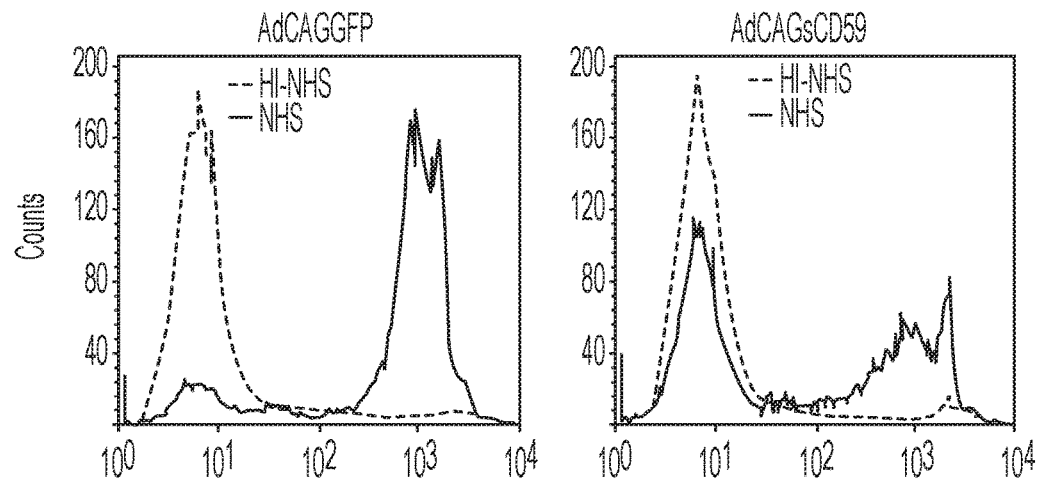
Figure 21B:
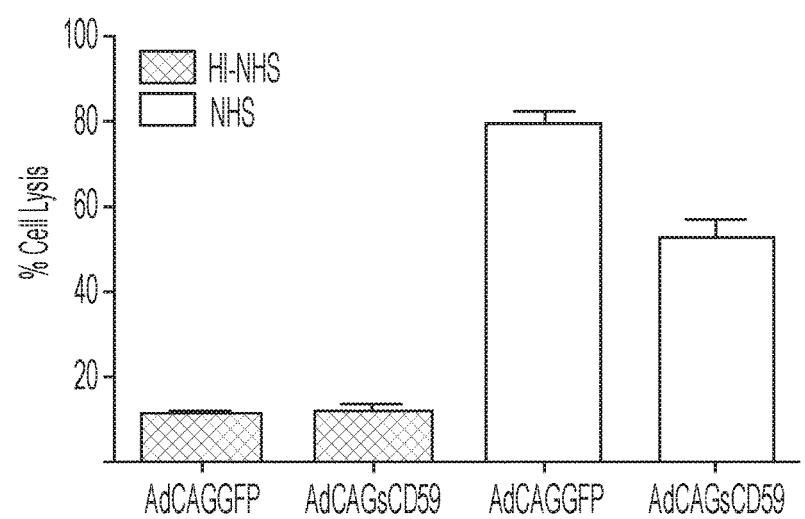

FIG. 21 is a set of printouts and graphs showing that AdCAGsCD59-conditioned media conferred significant protection in cells from human serum-mediated cell lysis.

FIG. 21 panel A are printouts of cell sorting data showing results of hepa-1c1c7 cells treated with either NHS or HI-NHS in media conditioned with either AdCAGGFP or AdCAGsCD59.

FIG. 21 panel B is a bar graph comparing percent cell lysis (ordinate) of hepa-1c1c7 cells treated with adenovirus strains (AdCAGsCD59, AdCAGGFP respectively) and serum: normal human serum (NHS, open bars) or heat-inactivated serum (HI-NHS, closed bars). No significant difference in cell lysis was observed in hepa-1c1c7 cells treated with HI-NHS in conditioned media from cells transfected with either AdCAGGFP or AdCAGsCD59. However, a significant reduction in cell lysis (34.08±6.40%, p<0.01) was observed in hepa-1c1c7 cells treated with NHS in media conditioned with AdCAGsCD59 relative to those cells treated with NHS in media conditioned with the control virus, AdCAGGFP.

Figure 22A:
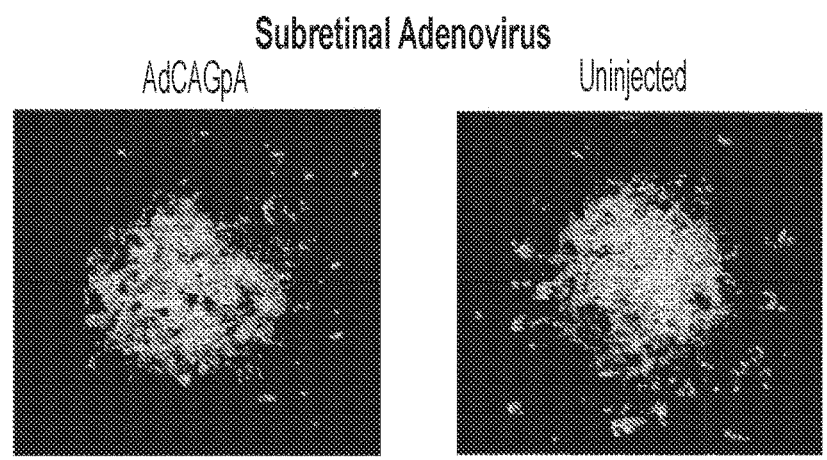
Figure 22B:
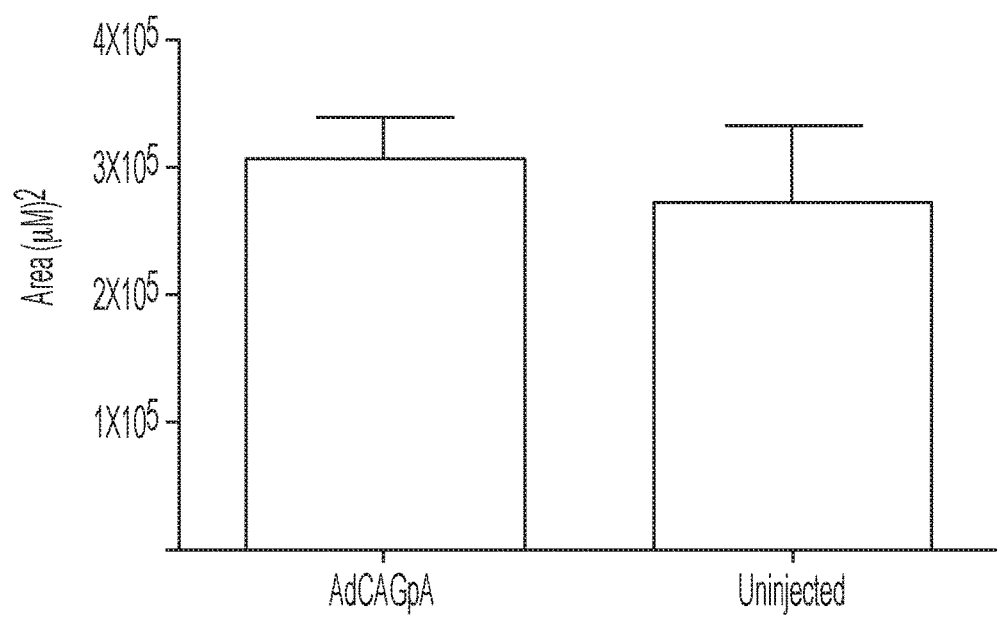

FIG. 22 is a set of photographs and a bar graph showing that delivery of adenovirus to mouse subretinal spaces did not affect size of laser-induced choroidal neovascularization (CNV). Mice were subretinally injected with AdCAGpA and control mice not injected were each subjected to laser burn treatment of eyes to induce CNV spots. The mice were sacrificed and eye tissues were stained with FITC-conjugated GSL I isolectin B4, a lectin specific for endothelial cells.

FIG. 22 panel A is a set of representative photomicrographs of eyecups from mice injected with AdCAGpA (left photograph) and eyecups from mice not injected (right photograph).

FIG. 22 panel B is a bar graph showing area ($\mu M^2$; ordinate) of CNV spots in mice having the following treatments (abscissa): injected with AdCAGpA (left bar), and not injected (right bar). No significant difference was observed in the size of CNV spots in mice injected with AdCAGpA compared to control mice (p>0.5).

FIG. 23 is a set of photographs and a bar graph that show that AdCAGpA and AdCAGsCD59 co-injected with AdCAGGFP resulted in equivalent levels of transduction and staining at sites distal to the sites of laser burn. Mice were subretinally injected with AdCAGpA:AdCAGGFP (1:10) or AdCAGsCD59:AdCAGGFP (1:10) respectively, and were subjected to laser burn treatment in the eyes to induce CNV spots. The mice were sacrificed and eye tissues were stained with FITC-conjugated GSL I isolectin B4.

FIG. 23 panel A is a set of representative photomicrographs showing RPE/choroid flatmounts in mice subretinally injected with AdCAGGFP:AdCAGpA(1:10; left photograph) and AdCAGGFP:AdCAGsCD59 (1:10; right photograph).

FIG. 23 panel B is a bar graph showing area ($\mu M^2$; ordinate) of CNV spots in mice injected the following adenovirus combinations (abscissa): AdCAGGFP:AdCAGpA(1:10; left bar) and AdCAGGFP:AdCAGsCD59 (1:10; right bar). No significant differences in area of transduction were observed between eyecups injected with AdCAGpA and AdCAGsCD59.

FIG. 24 is a set of photographs and a bar graph that show that AdCAGsCD59 delivered to murine RPE resulted in a significant reduction in laser-induced CNV. Mice were subretinally injected with AdCAGpA and AdCAGsCD59, respectively. The mice were subjected to laser burn treatment in the eyes to induce CNV spots. The mice were sacrificed and eye tissues were stained with FITC-conjugated GSL I, isolectin B4.

FIG. 24 panel A is a set of representative photomicrographs showing FITC-GSL I stained laser-induced CNV spots from eyes subretinally injected with either AdCAGpA (left photograph) or AdCAGsCD59 (right photograph).

FIG. 24 panel B is a bar graph showing area ($\mu M^2$; ordinate) of CNV spots in mice injected with the following adenovirus constructs (abscissa): AdCAGpA (left bar) and AdCAGsCD59 (right bar). Data show that AdCAGsCD59 transduction of murine RPE resulted in a 61.0±11.6% reduction in size of CNV spot area compared to AdCAGpA transduction of murine RPE (p<0.0001).

Figure 25A:
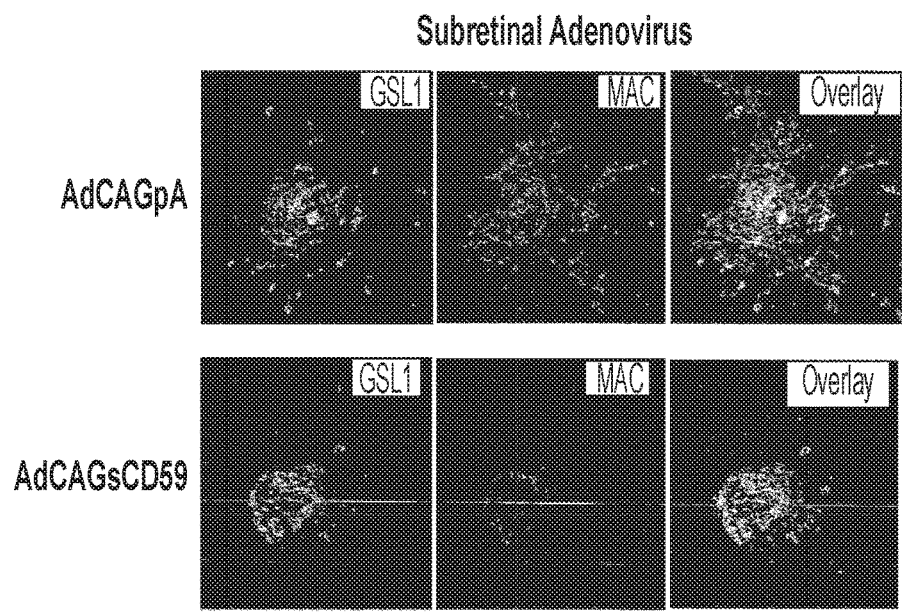
Figure 25B:
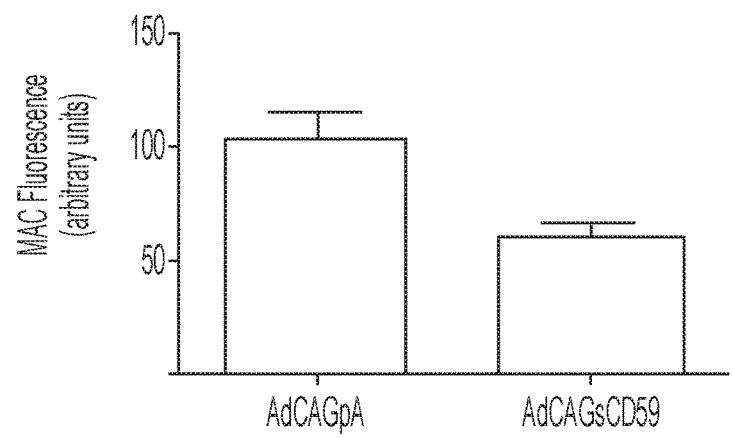

FIG. 25 is a set of photomicrographs and a bar graph showing that subretinally injecting AdCAGsCD59 significantly reduced MAC deposition at the site of laser-induced CNV.

FIG. 25 panel A is a set of representative photomicrographs showing laser-induced CNV spots in eyes injected with either AdCAGpA (first row) or AdCAGsCD59 (second row) and then stained with GSL I (left column) and anti-C9 antibody (MAC; middle column). The overlay (right column) illustrates deposition of MAC extending beyond the region stained positive for GSL I, particularly in the AdCAGpA-injected eyecup.

FIG. 25 panel B is a bar graph showing MAC fluorescence (ordinate) of CNV spots in mice injected with different adenovirus constructs (abscissa): AdCAGpA (left bar) and AdCAGsCD59 (right bar). A significant (40.9±13.3%, p<0.01) reduction in MAC deposition was observed in regions of laser burn in eyecups injected with AdCAGsCD59 compared to the eyecups injected with AdCAGpA.

Figure 26:
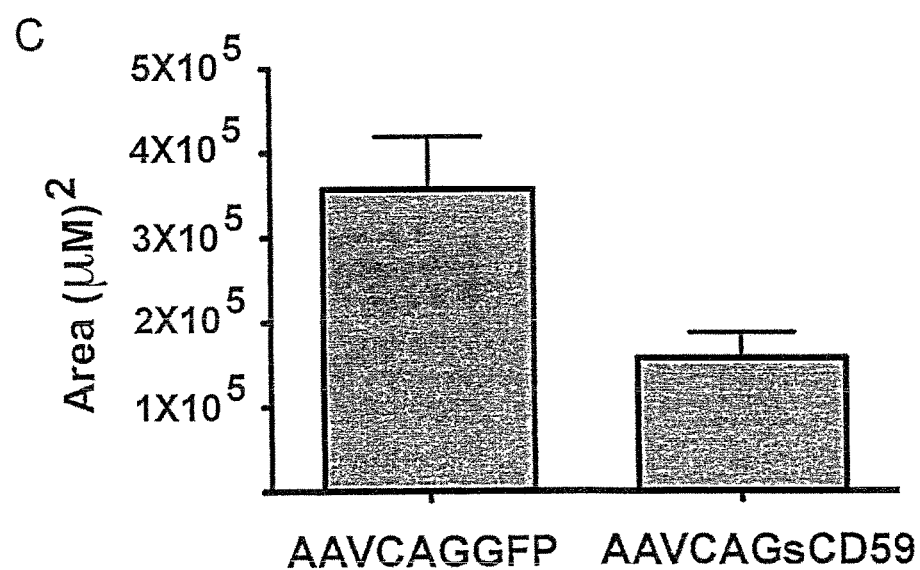

FIG. 26 is a drawing, a set of photographs and a bar graph showing that intravitreal delivery of an adeno-associated virus (AAV) expressing sCD59 resulted in significant protection against laser-induced CNV.

FIG. 26 panel A is a drawing of an expression cassette containing sCD59 under the control of the chicken β-actin promoter. The expression cassette was cloned into an AAV serotype 2 vector. A control AAV expressing GFP was also generated.

FIG. 26 panel B is a set of representative photomicrographs of laser-induced CNV spots observed in eyecups injected with AAVCAGGFP (left photomicrograph) or eyecups injected with AAVCAGsCD59 (right photomicrographs).

FIG. 26 panel C is a bar graph showing area ($\mu M^2$; ordinate) of CNV spots in mice injected with the following adenovirus constructs (abscissa): AAVCAGGFP (left bar), and AAVCAGsCD59 (right bar). A significant 56.0±18.1% (p<0.01) reduction in size of CNV was observed in eyecups injected with AAVCAGsCD59 compared eyecups injected with AAVCAGGFP.

Figure 27:
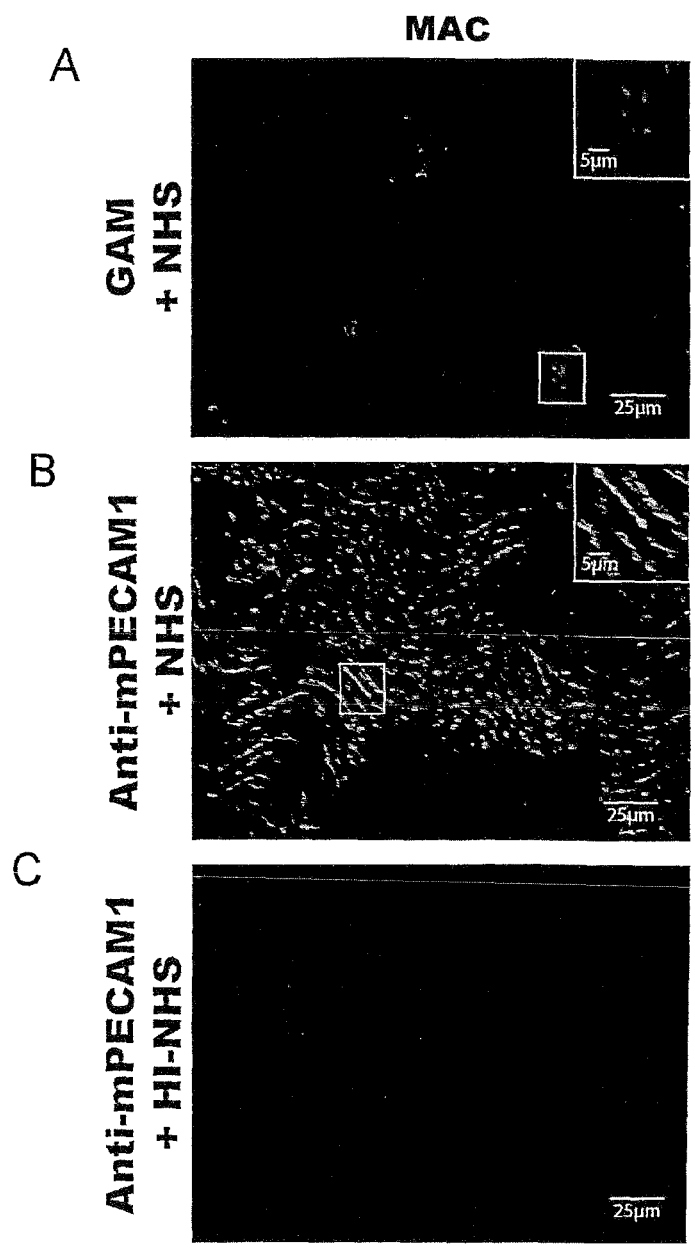

FIG. 27 is a set of photomicrographs showing that a cell specific antibody was required for deposition of human C5b-9 (MAC) on murine endothelial cells ex vivo. Images shown are representative of MAC deposition on endothelial cells of the lumen of murine aorta flatmount after incubation with: a generic anti-mouse (GAM) antibody and normal human serum (NHS; panel A), anti-mPECAM1 antibody and NHS (panel B), and anti-mPECAM1 antibody and heat-inactivated NHS (HI-NHS; panel C). The photomicrographs show MAC deposition on cells at different magnifications (length bars: 25 μm and 5 μm respectively). MAC deposition was observed with non-specific antibody (GAM) occuring in a few small patches, with individual cells stained most intensely along the cell membrane. The pattern of membrane staining on the aorta was similar after treatment with the anti-mPECAM1 antibody, and MAC deposition occurred more uniformly across the tissue. Aorta treated with anti-mPECAM1 antibody and HI-NHS showed little or no MAC staining.

Figure 28:
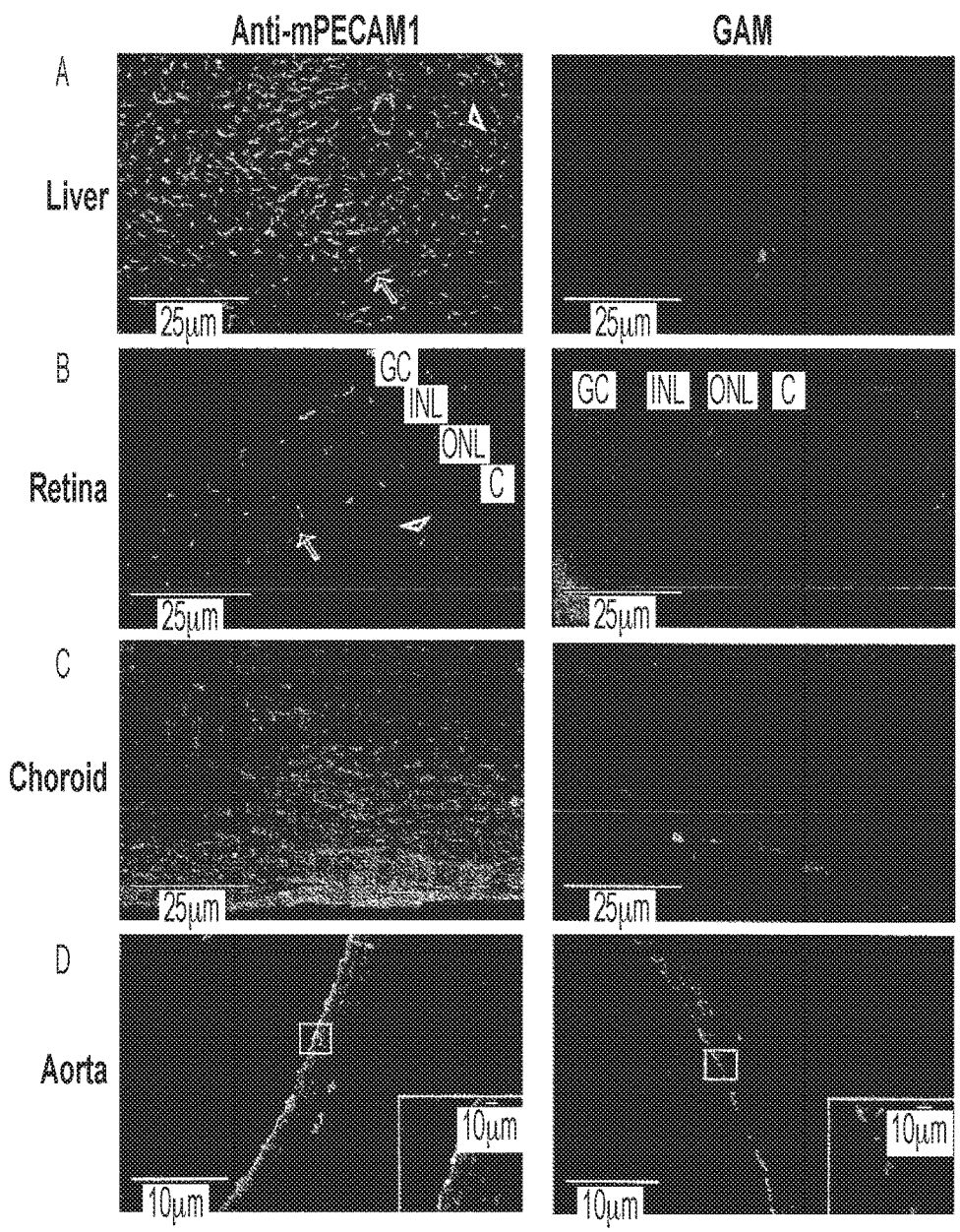

FIG. 28 is a set of photomicrographs showing that intracardial injection of anti-mPECAM1 (left column) antibody resulted in antibody binding to endothelial cells of various mouse tissues including the liver, retina, choroid and aorta in contrast to intracardial injection with GAM (right column). Anti-mPECAM1 bound to endothelial cells in the liver (panel A), particularly along the sinusoids (arrowhead) as well as the larger blood vessels (arrow). Cross-section of the posterior eyecup shows delivery and binding of antibody to endothelia of the choriocapillaris (arrowhead) and retinal vasculature (arrow; panel B). A flatmount of the choroid/RPE from BALB/C mice shows more clearly the binding of anti-mPECAM1 antibody to the choroidal endothelium (panel C). High levels of non-specific binding to aorta were observed, however anti-mPECAM1 antibody did bind the endothelial cell layer on the luminal surface (panel D). Intracardial injection of non-specific GAM antibody showed a lack of binding to endothelial cells. Symbols used include: GC, Ganglion Cell Layer; INL, Inner Nuclear Layer; ONL, Outer Nuclear Layer; C, Choroid Layer. The photomicrographs show MAC deposition on cells at different magnifications (length bars: 25 μm and 10 μm respectively).

Figure 29A:
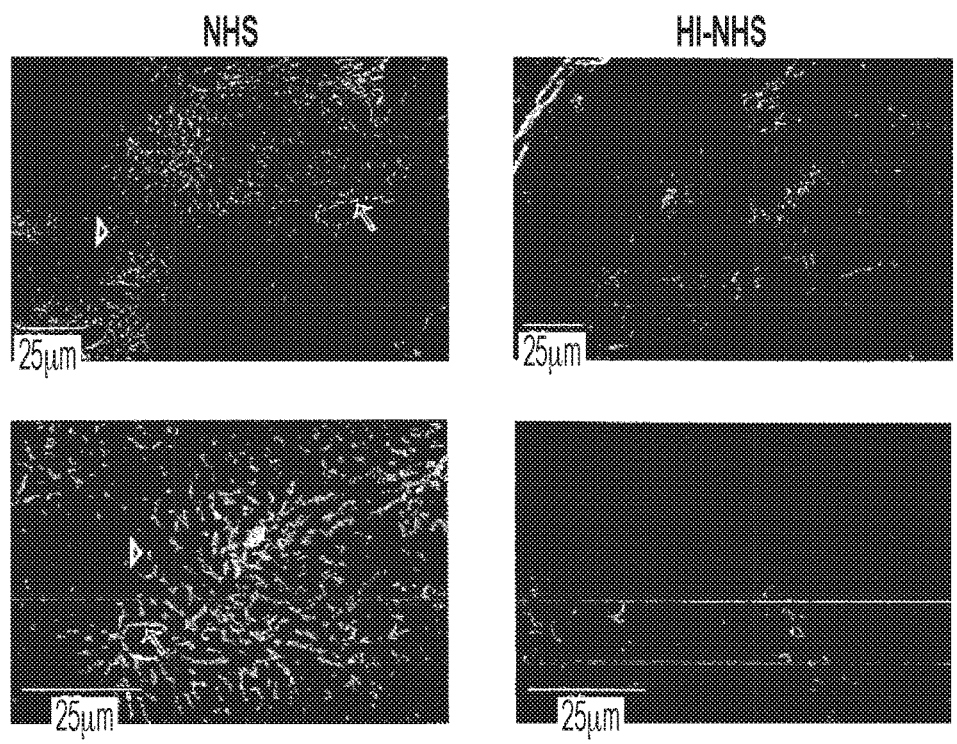
Figure 29B:
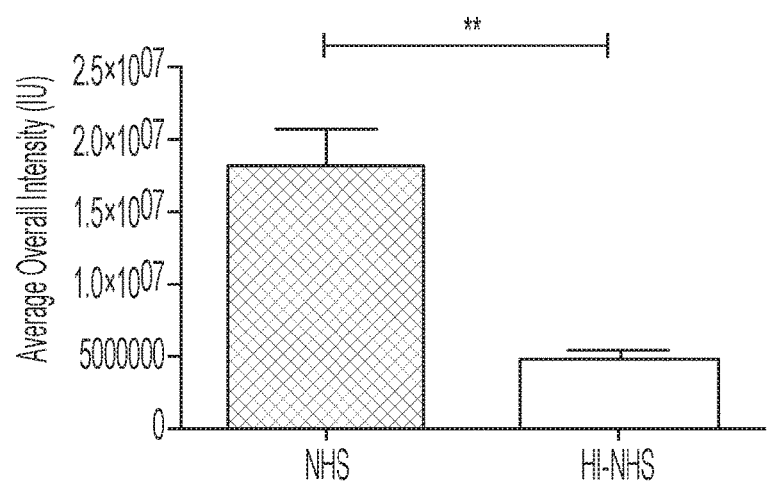

FIG. 29 is a set of photomicrographs and a graph showing that intracardial delivery of an anti-mPECAM1 antibody and perfusion with normal human serum (NHS) resulted in deposition of human C5b-9 (MAC) on endothelial cells of the murine liver.

FIG. 29 panel A is a set of photomicrographs of mice intra-cardially injected with anti-mPECAM1, perfused with NHS (left column) or HI-NHS (right column), and stained for human MAC deposition in the liver. Data show MAC deposition along the inner surface of sinusoid canals (arrowhead) and larger blood vessels (arrow). Animals intra-cardially injected with anti-PECAM1 and perfused with HI-NHS exhibited limited MAC deposition. The photomicrographs show MAC deposition on cells (length bar: 25 μm).

FIG. 29 panel B is a bar graph showing average overall intensity (RT; ordinate) of MAC staining in mice intra-cardially injected with anti-mPECAM1 and then perfused with either NHS (left bar) or HI-NHS (right bar). The average overall MAC staining intensity of liver in mice perfused with anti-mPECAM1 and NHS was significantly increased ($1.81 \times 10^7$ IU; p<0.01) compared that of mice intra-cardially injected with anti-mPECAM1 and perfused with HI-NHS ($0.48 \times 10^7$ IU; n=3).

Figure 30:
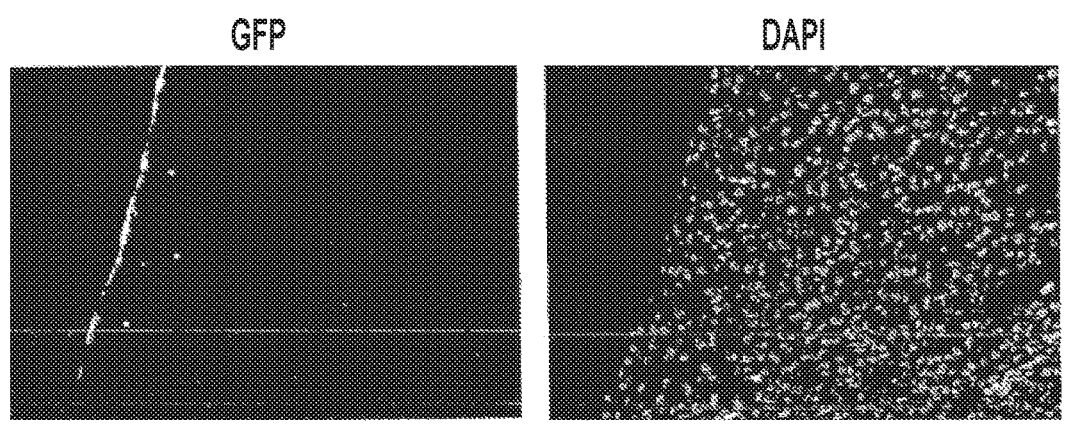

FIG. 30 is a set of photomicrographs showing that intra-peritoneal injection of AdCAGGFP resulted in significant protein expression in mouse liver. Representative images show GFP fluorescence (left photomicrograph) and DAPI stain (right photomicrograph) on liver sections seven days after intraperitoneal injection. It was observed that GFP expression occurred generally along the peritoneal membrane at the periphery of the liver. A small number of cells within the liver also showed GFP expression.

Figure 31A:
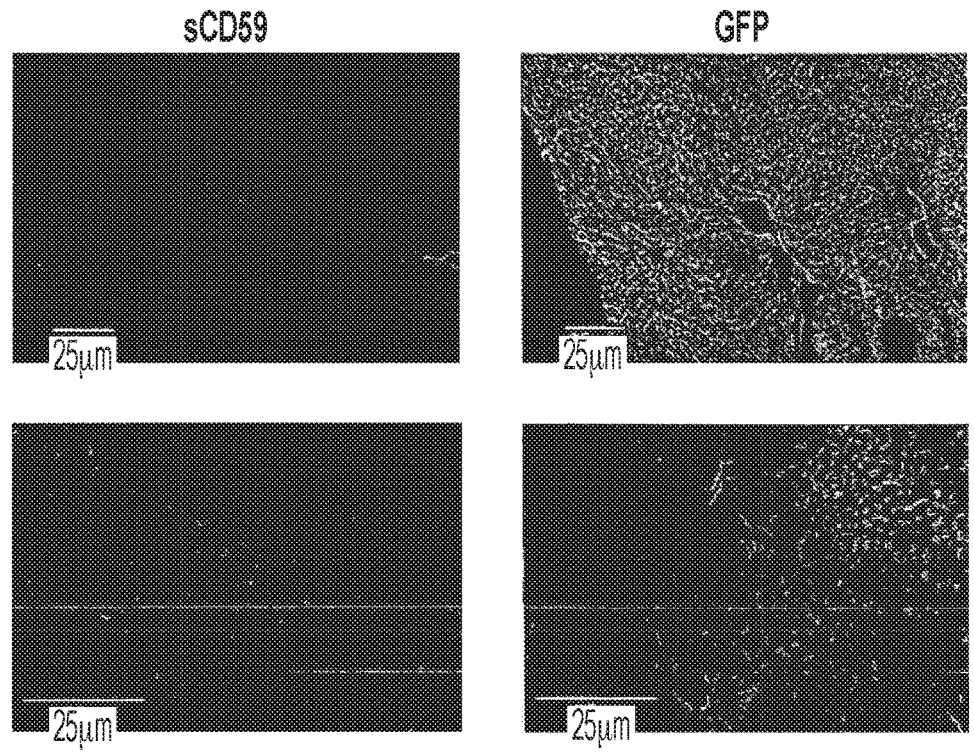
Figure 31B:
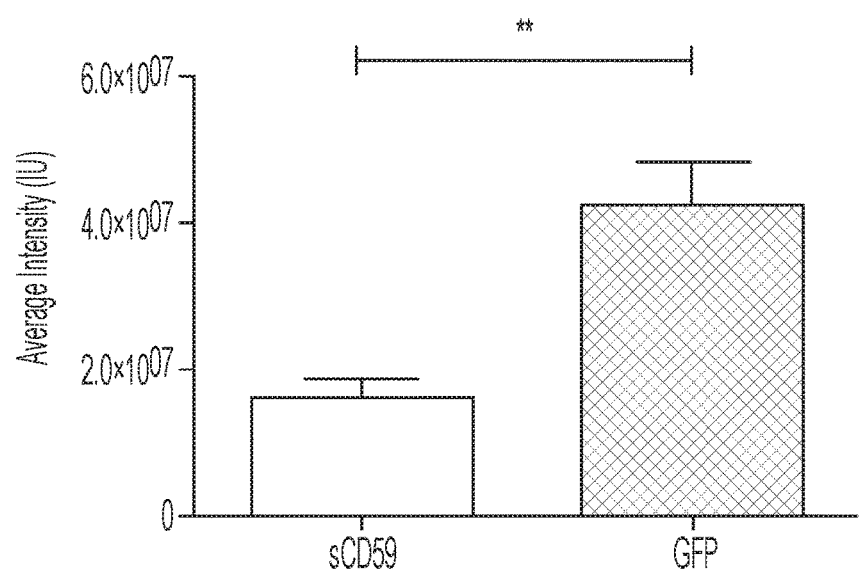

FIG. 31 is a set of photomicrographs and a graph showing that endothelial cells of liver vasculature of mice pre-injected with AdCAGsCD59 (sCD59), a human sCD59-expressing adenovirus, deposited significantly reduced C5b-9 (MAC) after intracardial perfusion of anti-mPECAM1/NHS compared to liver vasculature from mice pre-injected with AdCAGGFP and intracardial perfusion of anti-mPECAM1/NHS.

FIG. 31 panel A is a set of representative photomicrographs showing MAC deposition on sinusoidal endothelial cells, as well as the endothelial cells of blood vessels in mice injected with either AdCAGsCD59 (left photomicrographs) or AdCAGGFP (right photomicrographs) prior to intracardial injection with anti-mPECAM1 antibody and perfusion with NHS. At higher magnification (bottom row), the intensity and overall area of staining was greater in the GFP-treated group. The photomicrographs show MAC deposition on cells a magnification shown by 25 μm length bar.

FIG. 31 panel B is a bar graph showing average intensity (IU; ordinate) of MAC staining in mice pre-injected with either AdCAGsCD59 (sCD59; left bar) or AdCAGGFP (GFP; right bar) and then intra-cardially injected with anti-mPECAM1 and then perfused with NHS. The average overall MAC staining intensity of liver vasculature in mice injected with AdCAGsCD59 was significantly reduced ($1.60 \times 10^7$ IU; p<0.01) compared to that of AdCAGGFP-injected mice ($4.23 \times 10^7$ IU; n=8).

Figure 32A:
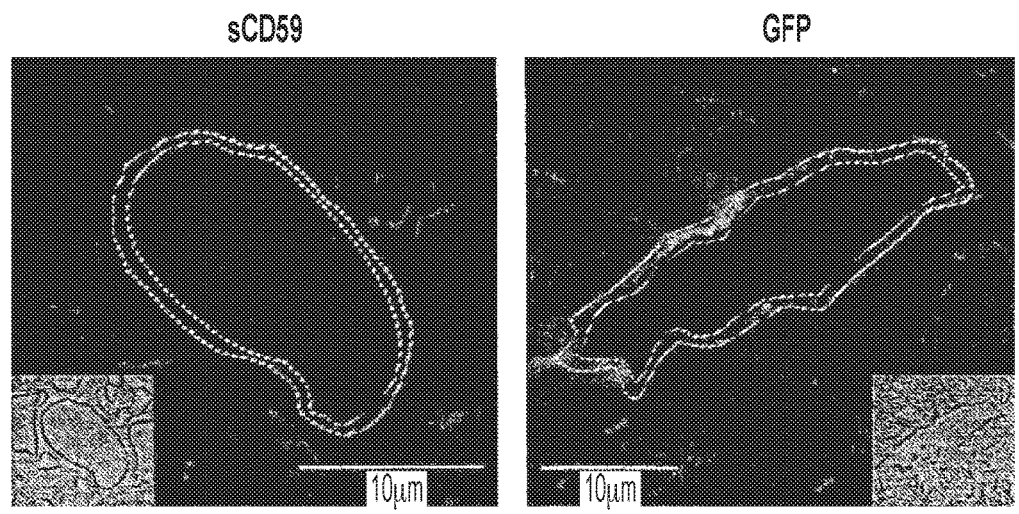
Figure 32B:
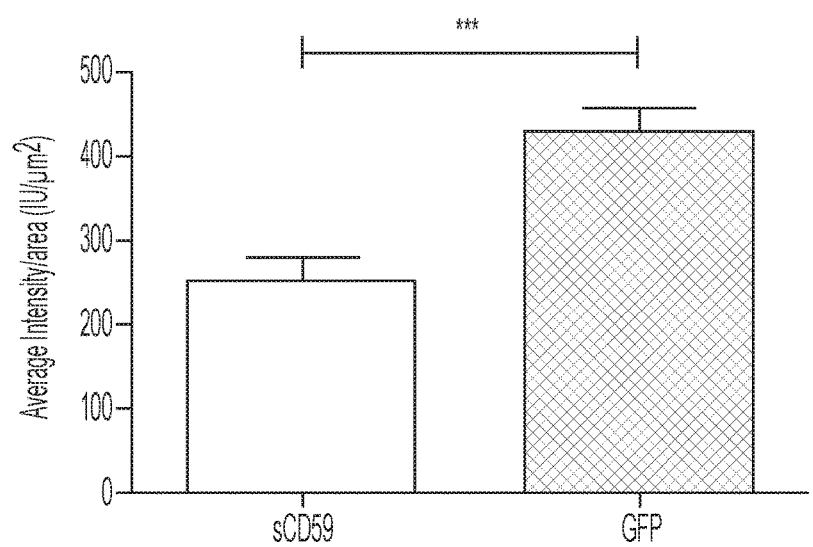

FIG. 32 is a set of photomicrographs and a graph showing that intraperitoneal injection of AdCAGsCD59 (sCD59) reduced C5b-9 (MAC) deposition in endothelial cells of the large (non-capillary) blood vessels of livers in mice relative to mice injected with AdCAGGFP (GFP).

FIG. 32 panel A shows a set of representative images showing MAC staining within the demarcated endothelial cell layer of a large blood vessel of the livers of mice injected with AdCAGsCD59 (left column) and mice injected with AdCAGGFP (right column), with corresponding brightfield images. The photomicrographs show MAC deposition on cells at a magnification shown by the 25 μm length bar.

FIG. 32 panel B is a bar graph showing average intensity/area (IU/$\mu m^2$; ordinate) of MAC staining in mice pre-injected with either AdCAGsCD59 (sCD59; left bar) or AdCAGGFP (GFP; right bar). The average MAC staining intensity per endothelium area of large liver vessels of AdCAGsCD59-injected mice was significantly reduced (251.27 IU/μm$^2$; p<0.001) relative to that of AdCAGGFP-injected mice (428.95 IU/μm$^2$; n=8).

DETAILED DESCRIPTION

Analysis of polymorphisms in several complement regulatory proteins including Factor H have implicated overactive complement in the pathogenesis of AMD (Hageman et al. 2005 Proc Natl Acad Sci USA 102: 7227-7232; Klein et al. 2005 Science 308: 385-389; and Haines et al. 2005 Science 308: 419-421; Edwards et al. 2005 Science 308: 421-424).

Immunohistochemical analysis of drusen, which are yellow deposits under the retina, and retinal pigment epithelium (RPE) from AMD patients indicated the presence of a variety of complement proteins including the membrane attack complex (MAC). However, cross-species differences between human and non-human complement systems have limited ability to test the efficacy of human complement regulatory proteins in non-human systems in vivo.

Provided herein is a humanized murine model for measuring human MAC deposition in vitro and in vivo. Examples herein use this model to measure protection by human CD59 of murine RPE, the pigmented cell layer just outside the neurosensory retina that nourishes retinal visual cells, from attack by human MAC. Using this model, local expression of exogenously delivered human complement regulatory protein CD59 was found to protect the RPE from human MAC deposition in vivo. Such protection of the RPE by CD59 indicates that this protection can prevent or treat AMD. The humanized model of MAC deposition on murine retina allows for safe and rapid testing of human complement proteins in vivo.

The complement system, a component of the overall immune system of an organism, is a biochemical cascade that assists clearing of pathogens within an organism. The complement system includes a number of small proteins found circulating in blood, usually as inactive zymogens. Stimulated by one of several triggers, proteases in the system cleave specific proteins to release cytokines and initiate an amplifying cascade of further cleavages. Activation of this biochemical cascade results in activation of MAC, a function for killing pathogens.

The complement system is classified into a set of differently activated pathways: the classical complement pathway, the alternative complement pathway, and the mannose-binding lectin pathway. These pathways generate variants of a protease, the C3-convertase. The classical complement pathway typically involves antibodies for activation (specific immune response), while the alternative and mannose-binding lectin pathways are activated by C3 hydrolysis or antigens without the presence of antibodies (non-specific immune response).

In these pathways, a C3-convertase cleaves and activates component C3, creating C3a and C3b and causing a cascade of further cleavage and activation events. One such activation event initiates component C5b. Activation of C5b initiates the membrane attack pathway, which results in formation of MAC, a cytolytic endproduct of the complement cascade that forms a transmembrane channel and causes osmotic lysis of target cells.

MAC is formed for example, on the surface of intruding pathogenic bacterial cells as a result of activation of the complement system. MAC is a complex of four complement system proteins (C5b, C6, C7, and C8) that bind to the outer surface of a plasma membrane of a target cell, and with a fifth protein (C9) that binds subsequently (Sims et al., U.S. Pat. No. 7,166,568 issued Jan. 23, 2007). The complement proteins bind together in such a confirmation that an external face of each protein is hydrophobic and associates with the lipid bilayer of the membrane of the target cell, while an internal face is hydrophilic, allowing passage of water through the cell. The proteins form a ring through the membrane of the cell and the ring structure acts as a tunnel through the membrane, allowing free diffusion of molecules through the cell which disrupts the internal environment of the cell killing it quickly.

Diseases associated with uncontrolled complement activity include: bacterial infection such as with *Haemophilus influenza, Streptococcus pnemoniae, Neisseria meningitidis;* angioedema; renal disease for example atypical haemolytic uremic syndrome; paroxysmal nocturnal hemoglobinuria; systemic lupus erythematosus; and central nervous system diseases including Alzheimer's disease and Huntington's disease.

An advantage of the methods, compositions and kits described herein is that a non-membrane binding sCD59 is effective in inhibiting MAC formation under the circumstances of delivery using a CD59-encoding nucleic acid. Examples herein show that membrane targeting of sCD59 is not required to inhibit MAC formation in vivo. Human sCD59 delivered by an approach using methods of gene therapy was observed herein to attenuate CNV in mice using either an adenovirus vector injected subretinally or an AAV vector injected intravitreally. The sCD59 delivered by a vector was observed to reduce the extent of MAC deposition on laser-induced CNV spots.

The eye provides an ideal environment for using sCD59. Examples herein show that sCD59 comprising no or a functionally ineffective membrane targeting moiety significantly attenuated MAC formation and reduced CNV in vivo. sCD59 delivered using vectors having a nucleotide sequence encoding the protein is therefore useful as a therapeutic for both the wet as well as dry forms of AMD.

Delivery of vectors carrying nucleotide sequences encoding soluble CD59 protein provides more effective expression than a GPI-anchored human CD59 expressed on murine RPE in vivo. GPI-anchored CD59 protected those cells from human complement mediated attack ex vivo, however data show that only those cells that synthesized and expressed the CD59 molecule on their surface were protected from complement-mediated damage. Methods using membrane-bound CD59 did not inhibit choroidal neovascularization, or even target of blood vessels, a tissue intimately implicated in wet AMD. Without being limited by any particular theory or mechanism of action, it is here envisioned that contacting cells with sCD59 produced a subset of cells that are 'factories' for local production and secretion of a soluble CD59, which protected a large number of adjacent ocular cells including the RPE and choroidal blood vessels.

Human sCD59 delivered for example using vectors and methods such as using an adenovirus vector injected subretinally or an AAV vector injected intravitreally attenuated CNV in murine subjects. Compositions, methods and kit described herein used sCD59 to reduce the extent of MAC deposition on laser-induced CNV spots. Examples herein show that sCD59 is useful for treating wet as well as dry forms of AMD and other ocular diseases associated with complement activity.

Compositions, methods and kits using nucleotide sequences encoding sCD59 offer additional advantages over protein-based delivery methods. Peptides and antibodies have limited half-lives in vivo and need to be re-administered on a regular basis. Current treatments for wet AMD patients include for example intraocular ranibizumab antibody injections every four to six weeks. This method of treatment exposes patients to complications associated pathologies such as endophthalmitis. The incidence of endophthalmitis is relatively low (0.16% per dose) in the presence of a robust immune system, however the rate increases substantially due to the cumulative effect of an attenuated complement system and serial injections over many years such as for treating chronic diseases such as AMD. Hence, frequent injection of complement inhibitors into AMD eyes is not desirable or effective. Compositions, methods and kits described herein using sCD59 limit the frequency of injection administration and therefore provide a more safe and effective treatment for subjects having complement disorders such as ocular pathologies.

Viral vectors such as adenovirus have been used to provide lifetime expression of transgenes in vivo in mice. AAV vectors for example have facilitated transgene expression in dogs for more than seven years. In humans, AAV has been found to have therapeutic transgene expression for over 3.7 years, the longest time periods studied. Adenovirus has been found to be an efficient vector for delivery of transgenes to ocular tissue and has been found to be safe in several ocular gene therapy trials. Adenovirus vectors engineered for long-term transgene expression and the technology for scaled production of such vectors are well known. AAV vectors have been shown to be safe for use in humans and are generally considered less immunogenic than adenovirus vectors. Examples herein show using AAV vectors to produce and deliver sCD59 in vivo. sCD59 delivered to AMD eyes using an AAV vector therefore is effective for long-term transgene expression. sCD59 is known to occur naturally endogenously in ocular tissues (at levels lower than that following recombinant transgene expression described herein). Therefore an immune response against sCD59 is not likely to be observed.

Examples herein show a pharmaceutical composition for treating macular degeneration including a vector carrying a nucleotide sequence encoding a recombinantly engineered human CD59 protein operably linked to a promoter sequence causing expression of the protein in a cell, such that the nucleotide sequence carries at least one mutation conferring loss of a glycosyl phosphatidyl inositol (GPI) anchoring function, such that the protein is expressed as a recombinant membrane-independent CD59 (rmiCD59) protein and is not membrane targeting, the composition further comprising a pharmaceutically acceptable buffer. In various embodiments, the macular degeneration is wet, or the macular degeneration is dry.

In a related embodiment, the pharmaceutical composition is formulated sterile for ocular delivery, in a dose effective to treat macular degeneration.

In related embodiments, the vector is at least one of: an engineered viral vector recombinantly linked to the nucleotide sequence encoding the rmiCD59 protein; and a synthetic gene delivery vector for delivery of the nucleotide sequence. For example, the viral vector is selected from: adenovirus, adeno-associated virus, a herpesvirus, a poxvirus, and a lentivirus; and the synthetic gene delivery vector is selected from a liposome, a lipid/polycation (LPD), a peptide, a nanoparticle, a gold particle, and a polymer.

In a related embodiment, the pharmaceutical composition further includes a peptide for overall delivery, POD, composition operably linked to the compound to obtain a conjugated compound, such that the POD includes a protein transduction domain (PTD). For example the POD composition is one shown in Kumar-Singh et al. PCT/US2008/010179 filed Aug. 28, 2008 or Kumar-Singh et al. U.S. publication 2010/0209447 published Aug. 19, 2010, each of which is incorporated herein by reference in its entirety.

In related embodiments, the composition formulated for ocular delivery further includes at least one of a pharmaceutically acceptable buffer, a pharmaceutically acceptable salt and a pharmaceutically acceptable emollient suitable for delivery by at least one route selected from: intra-ocular injection, subconjunctival injection, subtenon injection, eye drop, and ointment.

Related embodiments of the above pharmaceutical compositions include the dose of the viral vector particles administered to an affected eye selected from a range of about $10^7$ to about $10^9$; about $10^8$ to about $10^{10}$; about $10^9$ to about $10^{11}$; about $10^{11}$ to about $10^{12}$; and about $10^{11}$ to about $10^{13}$. In related embodiments, the pharmaceutical composition further includes at least one agent selected from the group consisting of: anti-tumor, antiviral, antibacterial, anti-mycobacterial, anti-fungal, anti-proliferative and anti-apoptotic.

In a related embodiment of the pharmaceutical composition, the promoter sequence is a ubiquitous promoter for general for expression in a mammalian cell for example a promoter from a gene encoding actin, polyhedron, and hydroxyl-methylglutaryl CoA reductase (HMGCR). For example, the promoter is a chicken beta-actin promoter or a human beta-actin promoter. Alternatively, the promoter sequence is a tissue specific promoter for expression in a specific cell-type for example rhodopsin promoter or tissue specific promoter for the eye or liver.

In a related embodiment, the nucleotide sequence encoding the uniCD59 includes a deletion of the GPI anchoring domain. In a related embodiment, the nucleotide sequence encoding the nniCD59 comprises at least one single amino acid alteration resulting in decrease or loss of function of the GPI anchoring domain. For example the CD59 is engineered to include a modified C-terminal GPI signal anchor sequence at an amino acid position affecting attachment of the GPI anchor, so that the mutation renders the anchor non-functional. For example the CD59 is engineered to delete the C-terminal GPI signal anchor sequence at an amino acid position affecting attachment of the GPI anchor, so that the mutation inhibits attachment of the anchor.

A method is also provided for formulating a composition for treating age-related macular degeneration (AMD) in a subject, including: engineering a vector to deliver and express a CD59 nucleotide sequence encoding an amino acid sequence corresponding to human CD59, such that the nucleotide sequence includes a mutation encoding for amino acids of a glycosyl phosphatidyl inositol (GPI) anchoring domain of the protein, such that the resulting vector encodes an engineered recombinant membrane-independent CD59 (rmiCD59) protein, and the vector is a viral vector or a synthetic gene delivery vector; and, contacting at least one ocular tissue of the subject with the composition, such that the cells of the tissue express and secrete the CD59 locally, thereby treating the subject for AMD.

In a related embodiment of the method, the viral vector is derived from a genetically engineered genome of at least one virus selected from: an adenovirus, an adeno-associated virus, a herpesvirus, and a lentivirus, and the synthetic gene delivery vector is selected from a liposome, a lipid/polycation (LPD), a peptide, a nanoparticle, a gold particle, and a polymer.

In a related embodiment, contacting further includes injecting by a route selected from subretinal; subconjunctival; subtenon; subcutaneous; intravenous; and intravitreal. In related embodiments of the method, the tissues contacted by the composition include at least one selected from: retinal pigment epithelium, retina, choroid, sclera, Bruch's membrane, and choroidal blood vessels.

Examples also provide a method of regulating complement activity or treating a complement activity disorder in a subject, the method including: contacting an affected tissue or organ of the subject at risk for or suffering from the complement activity disorder with a composition including a vector carrying a nucleotide sequence encoding a recombinantly engineered human CD59 protein operably linked to a promoter sequence causing expression of the protein in a cell, such that the protein includes at least one mutation resulting in loss of function of glycosyl phosphatidyl inositol (GPI) anchoring domain, such that the protein is recombinant membrane-independent CD59 (rmiCD59) and is not membrane targeting; and, observing a physiological indicium of the complement activity disorder after contacting, in comparison to an abnormal amount of the physiological indicium observed prior to contacting, such that a decrease after contacting compared to prior to contacting is a positive indication that the affected tissue or organ is treated.

In related embodiments of the method, the affected tissue is selected from epithelial tissue, endothelial tissue, and vascular tissue. In related embodiments, the affected organ is selected from eye, heart, kidney, lung, liver, pancreas, and vascular system. In related embodiments, the subject is a tissue or organ donor or recipient. For example, the subject is a immunocompromised patient that is an organ recipient.

In related embodiments of the method, the disorder is selected from: macular degeneration, bacterial infection, toxic shock syndrome (TSS), atypical hemolytic uremic syndrome, membranoproliferative glomerulonephritis, dense deposit disease, peroximal nocturnal hemoglobinurea, systemic lupus erythromatosis, and atherosclerosis and the like. For example, the disorder is macular degeneration, and observing further includes measuring the indication selected from: visual acuity; visual aberrations; and amount of MAC deposition. For example, the disorder is bacterial infection or TSS, and observing further includes measuring the indication selected from: bacterial titer in a tissue or bodily fluid, extent of fever, and extent of inflammation. For example, the disorder is membranoproliferative glomerulonephritis, and observing further includes measuring the indication selected from: serum complement; urine protein; urine nitrogen; urine creatinine; glomerular filtration rate; effective renal blood flow; filtration fraction; and glomerular sieving. For example, the disorder is atherosclerosis, and observing further includes measuring the indication selected from at least one of: serum low density cholesterol; serum total cholesterol; angioscopy; and quantitative colorimetric angioscopy.

In addition the examples include a method of assaying a serum complement component for prognosis or diagnosis of macular degeneration (MD), the method including: contacting a first sample of cells to a sample of the serum and measuring resulting lysis, and comparing extent of lysis to that in a second sample of control cells not so exposed to the serum and otherwise identical, such that the serum added to the first sample of cells is obtained from a patient in need of diagnosis for MD and an optional control serum is obtained from a normal subject and added to an optional third sample of cells, such that a greater extent of lysis in the first sample compared to that in the second sample and the optional third sample is an indication of prognosis or diagnosis of MD.

In a related embodiment, the method further includes contacting at least a fourth sample of cells to a candidate therapeutic composition and otherwise identically to the serum and measuring lysis, such that the extent of lysis of the third sample compared to that in the first sample and the second sample is a measure of protection by the candidate composition, thereby assaying for a potential therapeutic agent for efficacy in treatment of macular degeneration.

In a related embodiment, the method further includes prior to contacting with serum, contacting the cells with a recombinant vector encoding a gene capable of expressing a human recombinant membrane-independent CD59 (mriCD59) protein, such that the mriCD59 protein lacks a glycosyl phosphatidyl inositol anchoring domain, and such that a decrease in cell lysis in the presence of mriCD59 compared to absence of mriCD59 is an indicium of suitability of the patient for treatment of macular degeneration with mriCD59.

CD59 Protein

Data in Examples herein show that membrane-independent CD59 protein, for example soluble CD59 protein, inhibited MAC, preventing lysis of retina cells. CD59 is a membrane-bound glycoprotein found associated with membranes of cells including human erythrocytes, lymphocytes, and vascular endothelial cells. CD59 protein inhibits assembly of functional MACs and thus protects cells from complement-mediated activation and/or lysis.

Without being limited by any particular theory or mechanism of action, it is here envisioned that plasma membranes of cells are normally protected from the effects of complement by cell-surface proteins, e.g., CD59, that specifically inhibit activation of the C5b-9 pore upon C9 complement protein binding to membrane C5b-8 (Holguin et al. 1989 J. Clin. Invest. 84: 7-17; Sims et al. 1989 J. Biol. Chem. 264: 19228-19235; Davies et al. 1989 J. Exp. Med. 170: 637-654; Rollins et al. 1990 J. Immunol. 144: 3478-3483; and Hamilton et al. 1990 Blood 76: 2572-2577). CD59 competes with C9 complement protein for binding to C8 complement protein in the C5b-8 complex, thereby decreasing or preventing the formation of the C5b-9 membrane attack complex. CD59 thus acts to reduce both cell activation and cell lysis by terminal complement MACs.

Mature human CD59 protein is composed of 77 amino acids and has a molecular weight of 18-21 kD. Precursor human CD59 protein includes an amino-terminal signal peptide of 25 amino acids and a carboxyl-terminal peptide of 26 amino acids which results in attachment of a membrane anchor. Amino acid sequences of examples of precursor human CD59, a mature human CD59, and CD59 sequences of other mammals, e.g., baboon, African green monkey, owl monkey, marmoset, HVS-15, pig, rabbit, rat, and mouse, are shown in Sims et al. U.S. Pat. No. 7,166,568 issued Jan. 23, 2007.

Protein structure of CD59 includes a single cysteine-rich domain, a hydrophobic core with three loops and a small fourth helical loop (Yu et al. 1997 Journal of Experimental Medicine 185(4): 745-753).

The structure and sequence of the gene encoding CD59 has been characterized (Fodor et al. U.S. Pat. No. 5,624,837 issued Apr. 29, 1997). The gene is located on the short arm of chromosome 11 in humans, specifically chromosome 11p13 and 11p14 (Online Mendelian Inheritance in Man accession number and 107271), and consists of 4 exons spanning 20 kb (Petranka et al. 1992 Proc. Nat. Acad. Sci. 89: 7876-7879). An untranslated first exon is preceded by a G and C-rich promoter region that lacks a consensus TATA or CAAT motif. The second exon encodes the hydrophobic leader sequence of the protein, and the third exon encodes the N-terminal portion of the mature protein. The fourth exon encodes the remainder of the mature protein, including the hydrophobic sequence for glycophosphoinosital anchor attachment to a cell membrane.

CD59 is a glycosylphosphatidylinositol-anchored glycoprotein that is expressed on human peripheral blood leukocytes, erythrocytes, and many cell lines. The protein is expressed on both hematopoietic and non-hematopoietic non-hemopoietic cells, for example on endothelial cells, peripheral nerve fibers, neurons, microglia, oligodendrocytes, astrocytes, ependymal cells, epithelial cells, acinar cells of the salivary glands, bronchial epithelium, renal tubules and squamous epithelium. See Nose, M. et al. 1990 Immunology 70(2): 145-149; Vedeler, C. et al. 1994 Immunology 82(4): 542-547; and Hidestima, T. et al. 1990 Immunology 69(3): 396:401, each of which is incorporated herein by reference in its entirety. A cDNA encoding CD59 was reported by Sawada, R. et al. 1989 Nucleic Acids Res 17(16): 6728. CDNA encoding CD59 has also been cloned from human T-cell leukemia (YT) and human erythroleukemia (K562) cell lines, and CD59 has been transiently expressed in COS cells (Walsh, L. A. et al. 1990 Eur J. Immol 21(3): 847-850). Human CD59 includes 26 amino acids located at the C terminus, which specifies a signal sequence for attachment of a glycosyl phosphatidyl inositol anchor (GPI anchor) at amino acid asparagine at position 77. A cDNA sequence of CD59 is shown in Fodor et al., U.S. Pat. No. 5,624,837 issued Apr. 29, 1997, which is incorporated herein by reference in its entirety.

Analysis of the physical association of CD59 with components of MAC shows that separate binding sites for CD59 are contained within the α-chains of each of human C8 and human C9. The binding site for interactions of human CD59 with human C9 has been identified as amino acid residues 42 to 58 in the sequence of mature human CD59, that bind to the region of human C9 corresponding to human amino acid residues 334 to 418 of that protein, more particularly human C9 amino acid residues 359 to 384, immediately C-terminal to the predicted membrane-inserting domain of C9 (Sims et al. PCT/US96/17940 filed Nov. 8, 1996 which is incorporated herein by reference in its entirety).

The active surface exposed amino acid residue side chains that are available to bind C8/C9, identified from solution structure of mature human CD59 from published NMR data and the knowledge of the active portion of the CD59 molecule, are histidine at position 44, asparagine at position 48, aspartic acid at position 49, threonine at positions 51 and 52, arginine at position 55, and glutamic acid at position 58. NMR structures for CD59 are described in deposits by Kieffer et al., Human Complement Regulatory Protein CD59 (Extracellular Region, Residues 1 70; NMR, 10 Structures), MMDB Id: 891, PDB Id: 1ERH; Kieffer et al., Human Complement Regulatory Protein CD59 (Extracellular Region, Residues 1 70; NMR, Restrained), MMDB Id: 890, PDB Id: lERG; Fletcher et al., CD59 Complexed With Glcnac-Beta-1,4-(Fuc-Alpha-1,6)-Glcnac-Beta-1 (NMR, 10 Structures), MMDB Id: 498, PDB Id: 1CDS; Fletcher et al., CD59 Complexed With Glenac-Beta-1,4-Glenac-Beta-1 (NMR, 10 Structures), MMDB Id: 497, PDB Id: 1 CDR. The 1 CDS and 1 CDR deposits by Fletcher et al. Amino acid sequences of CD59 that present these side chains at the same relative positions function in a manner similar to human CD59 (Sims et al.), and such variants are within the scope of the methods, kits and pharmaceutical compositions herein.

The relationship between complement activation and abnormal levels of autoantibodies has been analyzed with respect to ocular diseases such as macular degeneration and other conditions. Hageman et al. U.S. patent application number 2005/0287601 published Dec. 29, 2005 proposes diagnosing macular degeneration by measuring presence of autoantibodies specific for a retinal protein (RPE and choroid proteins) in samples from AMD patients.

Theories have connected causation of Alzheimer's disease and age-related macular degeneration by complement, and prevention inhibiting activation of the complement system and formation of MAC. Dinu U.S. patent application number 2007/0196367 A1 published Aug. 23, 2007 proposes preventing debris formation by inhibiting complement as a therapeutic for Alzheimer's disease and AMD. Patil et al. U.S. patent application number 2007/0203190 A1 published Aug. 30, 2007 lists hydroxylamine compounds (e.g., TEMPOL-H, TEMPO-H, and OXANO-H) or ester derivatives as putative inhibitors of complement activation.

Tomlinson et al., U.S. patent application number 2005/0265995 published Dec. 1, 2005 inhibits complement-directed proteinuria in rats using an agent produced by linking each of complement inhibitors Crry and CD59 at the amino-terminus to single-chain antibody (scFv) that binds to rat glomerular epithelial cells and proximal tubular epithelial cells. Soluble CD59 is described in this reference as ineffective as an inhibitor. Bora et al. 2007 J. Immunol 178: 1783-1790 uses recombinant methods to produce a membrane targeting composition by fusing the binding arm, Fe, of an immunoglobulin G (IgG1) to CD59 protein (rsCD59a-Fc), and injects this fusion into mice by intravenous, intraocular (intravitreal) and intra-peritoneal routes. Numbers of CNV-positive spots were reduced in subjects treated with the fusion protein by the intraperitoneal route compared to intravitreal and intravenous routes. The Fc functionality may result in immediate binding upon contact of the fusion protein generally and non-specifically to cells following administration. Administering purified protein is further limited by metabolism and half-life due to presence of proteases and peptidases. Tomlinson et al. 2009 IOVS 50(7): 3056-3064 reduced the size of CNV spots in a mouse model by intravenously injecting the animals having CNV spots with a plasmid encoding a fusion protein complement inhibitor, produced by linking the N-terminus binding domain of factor H to a fragment of complement receptor 2 (CR2) that targets membrane molecules on cells.

A CD59 composition used herein lacks the primary amino acid sequence for a functional GPI anchor. A functional equivalent protein includes a modified GPI anchor domain amino acid sequence that is functionally defective and lacks the ability to target a membrane. A sCD59 is an example of a recombinant membrane-independent CD59 (rmiCD59). Additional methods of obtaining membrane-independent CD59 include non-recombinant methods such as providing an inhibitor of membrane association, for example, synthesizing CD59 in vivo or in vitro such that the GPI anchor is lacking. Methods of obtaining the membrane-independent CD59 are shown in examples herein. Additional recombinant techniques for altering the nucleic acid sequence and amino acid sequence of a molecule are well known in the art of genetics and molecular biology.

In various embodiments, the composition includes a CD59 protein that includes a full length nucleic acid of CD59 that was modified to remove the signal sequence for attachment of the GPI anchor at the nucleotides encoding amino acid asparagine at position 77. Alternatively the nucleic acid sequence of CD59 is modified by point mutations, substitutions or deletions to obtain a nucleic acid sequence that encodes an amino acid sequence that has a modified amino acid sequence at the GPI anchor location, such that the protein is unable to attach to a membrane of a cell.

The term "membrane independent" as used herein refers to a CD59 amino acid sequence that lacks a GPI anchor or has a modified GPI anchor that lacks function and ability to bind to a cell membrane or a cell-membrane-associated structure such as a membrane-bound protein.

GPI anchoring involves a multi-step pathway in the endoplasmic reticulum including the interaction of numerous gene products. Many proteins including CD59 require GPI to be expressed at the cell surface and to function effectively. The mechanism by which structure in a protein signal encodes for attachment of GPI anchors is reviewed by Orlean et al. 2007 JLR 48: 993-1011. GPI attachment generally involves an amino acid sequence that contains: a hydrophobic N-terminal secretion signal that targets the protein to the ER, and a C-terminal GPI signal anchor sequence. In addition to the native CD59 secretion signal which is located at the amino terminus of the protein and is cleaved in vivo, other secretion signals are suitable for CD59 protein and are within the scope of the methods herein. General eukaryotic secretion signals that are suitable for use in mammalian cells here are described for example in Ding et al. U.S. Pat. No. 6,733,997 B1 issued May 11, 2004; Tan et al. 2002 Protein Engineering 15(4): 337-345; and Tan et al. 1999 Biochim. Biophys. Acta 1452: 103-120, each of which is incorporated herein by reference in its entirety.

The amino acid to which the GPI becomes linked is referred to as the omega (ω) residue, with amino acids N-terminal to the omega residue referred to as omega-minus (ω−) and with amino acids C-terminal to the omega residue referred to as omega-plus (ω+). The GPI anchor sequence includes a stretch of about ten polar amino acids (i.e., ω−10 to ω−1), for example arginine, lysine, aspartate, glutamate, asparagine, or glutamate, that form a flexible linker region. The ω residue has been observed to be one of: glycine, alanine, serine, asparagine, aspartic acid, or cysteine. Mutation including substitution and deletion of nucleic acids encoding amino acids at omega positions are used to reduce or eliminate the attachment of the GPI anchor or reduce or eliminate the effective functionality of the GPI anchor. For example, such a variation includes substituting the nucleic acids encoding hydrophobic leucine (e.g., nucleic acids CTG) and alanine (e.g., nucleic acids GCA) with nucleic acids encoding glycine (e.g., nucleic acids CAG) and glutamate (e.g., nucleic acids GAA), which are less hydrophobic (i.e., more hydrophilic) amino acids. Alternatively, a variation includes substituting the ω residue with another amino acid, for example substituting a glycine for a tyrosine.

Other promoter sequences that regulate transcription of CD59 gene sequences are within the scope of expression of the vectors herein. These promoters are for example constitutive promoters, cell cycle-specific promoters, ubiquitous promoters, tissue-specific promoters, metabolically regulated promoters, inducible promoters, and promoters that are found in specific subjects including humans and animals. Examples of promoters and promoter systems are shown for example in Evans et al. U.S. Pat. No. 6,677,311 B1 issued Jan. 13, 2004; Clark et al. U.S. Pat. No. 7,109,029 B2 issued Sep. 19, 2006; and Hallenbeck et al. U.S. Pat. No. 5,998,205 issued Dec. 7, 1999, each of which is incorporated herein by reference in its entirety.

In the remainder of the protein not involved in GPI anchoring, the scope of the CD59 protein herein is envisioned to include conservative sequence modifications. As used herein, the term "conservative sequence modifications" refers to amino acid modifications that do not significantly affect or alter the characteristics of the CD59 protein or membrane-independent CD59 containing the amino acid sequence, i.e., amino acid sequences of CD59 that present these side chains at the same relative positions will function in a manner similar to human CD59. Such conservative modifications include amino acid substitutions, additions and deletions. Modification of the amino acid sequence of CD59 is achieved using any known technique in the art e.g., site-directed mutagenesis or PCR based mutagenesis. Such techniques are described in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the CD59 amino acid sequence is an amino acid sequence that is substantially identical to that of the wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 80%, 85%, 90%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., Nuc. Acids Research 22:4673, 1994, BL2SEQ by Tatusova and Madden, FEMS Microbiol. Lett. 174:247, 1999, SAGA by Notredame and Higgins, Nuc. Acids Research 24: 1515, 1996, and DIALIGN by Morgenstern et al., Bioinformatics 14: 290, 1998.

Vectors

In various embodiments of the invention herein, a method for treating a complement disorder (e.g., AMD) is provided, the method including contacting cells or tissue with a pharmaceutical composition including a source of membrane independent CD59 protein or as a source of CD59 expression in vivo. For example, the CD59 protein is administered as a recombinantly produced protein. The term "recombinant" refers to proteins produced by manipulation of genetically modified organisms, for example micro-organisms.

In accordance with the present invention a source of CD59 includes polynucleotide sequences that encode the CD59 protein, for example, engineered into recombinant DNA molecules to direct expression of the CD59 protein in appropriate host cells. To express a biologically active CD59 protein, a nucleotide sequence encoding the CD59 protein, or functional equivalent, is inserted into an appropriate expression vector, i.e., a vector that contains the necessary nucleic acid encoding elements that regulate transcription and translation of the inserted coding sequence, operably linked to the nucleotide sequence encoding the CD59 protein amino acid sequence.

Methods that are well known to those skilled in the art are used to construct expression vectors containing a sequence encoding the CD59 protein operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to contain and express a CD59 protein encoding sequence. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989.

Virus vectors include, but are not limited to, adenovirus vectors, lentivirus vectors, adeno-associated virus (AAV) vectors, and helper-dependent adenovirus vectors. Virus vectors deliver a nucleic acid sequence that encodes CD59 protein that as shown herein interferes with the deleterious action of the MAC in pathogenesis of AMD. Adenovirus packaging vectors are commercially available from American Type Tissue Culture Collection (Manassas, Va.). Methods of constructing adenovirus vectors and using adenovirus vectors are shown in Klein et al. 2007 Ophthalmology 114: 253-262, and van Lecuwen et al. 2003 Eur. J. Epidemiol. 18: 845-854.

Adenovirus vectors have been used in eukaryotic gene expression (Levrero et al. 1991 Gene, 101: 195-202) and vaccine development (Graham et al. 1991 Methods in Molecular Biology: Gene Transfer and Expression Protocols 7, (Murray, Ed.), Humana Press, Clifton, N.J., 109-128). Further, recombinant adenovirus vectors are used for gene therapy (Wu et al. U.S. Pat. No. 7,235,391 issued Jun. 26, 2007 which is incorporated herein by reference in its entirety).

Recombinant adenovirus vectors are generated, for example, from homologous recombination between a shuttle vector and a provirus vector (Wu et al., U.S. Pat. No. 7,235,391 issued Jun. 26, 2007). The adenovirus vectors herein are replication defective, for example, are conditionally defective, lacking adenovirus E1 region, and a polynucleotide encoding CD59 is introduced at the position from which the E1-coding sequences have been removed. The polynucleotide encoding the CD59 gene alternatively is inserted in the E3 region.

Helper cell lines may be derived from human cells such as, 293 human embryonic kidney cells, muscle cells, hematopoietic cells or other human embryonic mesenchymal or epithelial cells. Alternatively, the helper cells may be derived from the cells of other mammalian species that are permissive for human adenovirus, e.g., Vero cells or other monkey embryonic mesenchymal or epithelial cells. Generation and propagation of these replication defective adenovirus vectors using a helper cell line is described in Graham et al 1977 J. Gen. Virol. 36: 59-72.

Lentiviral vector packaging vectors are commercially available from Invitrogen Corporation (Carlsbad Calif.). An HIV-based packaging system for the production of lentiviral vectors is prepared using constructs in Naldini et al. 1996 Science 272: 263-267; Zufferey et al. 1997 Nature Biotechnol. 15: 871-875; and Dull et al. 1998 J. Virol. 72: 8463-8471.

A number of vector constructs are available to be packaged using a system, based on third-generation lentiviral SIN vector backbone (Dull et al. 1998 J. Virol. 72: 8463-8471). For example the vector construct pRRLsinCMVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the *Aequora* jellyfish green fluorescent protein (GFP) driven by the CMV promoter, and the woodchuck hepatitis virus PRE element, which appears to enhance nuclear export. The GFP marker gene allows quantitation of transfection or transduction efficiency by direct observation of UV fluorescence microscopy or flow cytometry (Kafri et al. 1997 Nature Genet. 17: 314-317; and Sakoda et al. 1999 J. Mol. Cell. Cardiol. 31: 2037-2047).

Manipulation of retroviral nucleic acids to construct a retroviral vector containing the gene that encodes for CD59 protein and packaging cells is accomplished using techniques known in the art. See Ausubel, et al., 1992, Volume 1, Section III (units 9.10.1-9.14.3); Sambrook, et al., 1989. Molecular Cloning: A Laboratory Manual. Second Edition. Cold Spring Harbor Laboratory Press, Cold Spring Harbor, N.Y.; Miller, et al., Biotechniques. 7:981-990, 1989; Eglitis, et al., Biotechniques. 6:608-614, 1988; U.S. Pat. Nos. 4,650, 764, 4,861,719, 4,980,289, 5,122,767, and 5,124,263; and PCT patent publications numbers WO 85/05629, WO 89/07150, WO 90/02797, WO 90/02806, WO 90/13641, WO 92/05266, WO 92/07943, WO 92/14829, and WO 93/14188, each of which is incorporated by reference in its entirety.

A retroviral vector is constructed and packaged into non-infectious transducing viral particles (virions) using an amphotropic packaging system. Examples of such packaging systems are found in, for example, Miller et al. 1986 Mol. Cell Biol. 6 :2895-2902; Markowitz et al. 1988 J. Virol. 62:1120-1124; Cosset et al. 1990 J. Virol. 64: 1070-1078; U.S. Pat. Nos. 4,650,764, 4,861,719, 4,980,289, 5,122,767, and 5,124,263, and PCT patent publications numbers WO 85/05629, WO 89/07150, WO 90/02797, WO 90/02806, WO 90/13641, WO 92/05266, WO 92/07943, WO 92/14829, and WO 93/14188, each of which is incorporated by reference in its entirety.

Generation of "producer cells" is accomplished by introducing retroviral vectors into the packaging cells. Examples of such retroviral vectors are found in, for example, Korman et al. 1987 Proc. Natl. Acad. Sci. USA. 84: 2150-2154; Morgenstern et al. 1990 Nucleic Acids Res. 18: 3587-3596; U.S. Pat. Nos. 4,405,712, 4,980,289, and 5,112,767; and PCT patent publications numbers WO 85/05629, WO 90/02797, and WO 92/07943.

Herpesvirus packaging vectors are commercially available from Invitrogen Corporation, (Carlsbad, Calif.). Exemplary herpesviruses are an a-herpesvirus, such as *Varicella-Zoster* virus or pseudorabies virus; a herpes simplex virus such as HSV-1 or HSV-2; or a herpesvirus such as Epstein-Barr virus. A method for preparing empty herpesvirus particles that can be packaged with a desired nucleotide segment, for example a CD59 nucleotide or polynucleotide sequence, in the absence of a helper virus that is capable to most herpesviruses is shown in Fraefel et al. (U.S. Pat. No. 5,998,208, issued Dec. 7, 1999 which is incorporated by reference in its entirety).

The herpesvirus DNA vector can be constructed using techniques familiar to the skilled artisan. For example, DNA segments encoding the entire genome of a herpesvirus is divided among a number of vectors capable of carrying large DNA segments, e.g., cosmids (Evans, et al., Gene 79, 9-20, 1989), yeast artificial chromosomes (YACS) (Sambrook, J. et al., MOLECULAR CLONING: A LABORATORY MANUAL, 2nd Edition, Cold Spring Harbor Press, Cold Spring Harbor, N.Y., 1989) or *E. coli* F element plasmids (O'Conner et al. 1989 Science 244:1307-1313).

For example, sets of cosmids have been isolated which contain overlapping clones that represent the entire genomes of a variety of herpesviruses including Epstein-Barr virus, *Varicella-Zoster* virus, pseudorabies virus and HSV-1. See M. van Ziji et al. 1988 J. Virol. 62: 2191; Cohen et al. 1993 Proc. Nat'l Acad. Sci. U.S.A. 90: 7376; Tomkinson et al. 1993 J. Virol. 67: 7298; and Cunningham et al. 1993 Virology 197: 116.

AAV is a dependent parvovirus in that it depends on co-infection with another virus (either adenovirus or a member of the herpes virus family) to undergo a productive infection in cultured cells (Muzyczka 1992 Curr Top Microbiol Immunol, 158: 97 129). For example, recombinant AAV (rAAV) virus is made by co-transfecting a plasmid containing the gene of interest, for example, the CD59 gene, flanked by the two AAV terminal repeats (McLaughlin et al. 1988 J. Virol., 62(6): 1963-1973; Samulski et al. 1989 J. Virol, 63: 3822-3828) and an expression plasmid containing the wild-type AAV coding sequences without the terminal repeats. Cells are also contacted or transfected with adenovirus or plasmids carrying the adenovirus genes required for AAV helper function. Recombinant AAV virus stocks made in such fashion include with adenovirus which must be physically separated from the recombinant AAV particles (for example, by cesium chloride density centrifugation).

Adeno-associated virus (AAV) packaging vectors are commercially available from GeneDetect (Auckland, New Zealand). AAV has been shown to have a high frequency of integration and infects nondividing cells, thus making it useful for delivery of genes into mammalian cells in tissue culture (Muzyczka 1992 Curr Top Microbiol Immunol 158: 97-129). AAV has a broad host range for infectivity (Tratschin et al. 1984 Mol. Cell. Biol. 4: 2072-2081; Laughlin et al. 1986 J. Virol., 60(2): 515-524; Lebkowski et al. 1988 Mol. Cell. Biol. 8(10): 3988-3996; McLaughlin et al. 1988 J. Virol. 62(6):1963-1973).

Methods of constructing AAV vectors and using AAV vectors are described, for example in U.S. Pat. No. 5,139,941 (Wu et al.) issued Jun. 26, 2007 and U.S. Pat. No. 4,797,368 (Carter et al.) issued Jan. 10, 1989. Use of AAV in gene delivery is further described in LaFace et al. 1988 Virology 162(2): 483 486; Zhou et al. 1993 Exp. Hematol, 21: 928-933; Flotte et al. 1992 Am. J. Respir. Cell Mol. Biol. 7(3): 349-356; and Walsh et al. 1994 J. Clin. Invest 94: 1440-1448.

Recombinant AAV vectors have been used successfully for in vitro and in vivo transduction of marker genes (Kaplitt et al. 1994 Nat Genet., 8(2):148-154; Lebkowski et al. 1988 Mol. Cell. Biol. 8(10): 3988-3996; Samulski et al. 1991 EMBO J. 10: 3941-3950; Shelling and Smith 1994 Gene Therapy, 1: 165-169; Yoder et al. 1994 Blood, 82 (Supp.): 1: 347A; Zhou et al. 1993 Exp. Hematol 21: 928-933; Tratschin et al. 1985 Mol. Cell. Biol. 5: 3258-3260; McLaughlin et al. 1988 J. Virol. 62(6): 1963-1973) and transduction of genes involved in human diseases (Flotte et al. 1992 Am. J. Respir. Cell Mol. Biol. 7(3): 349-356; Ohi et al. 1990 Gene, 89(2): 279-282; Walsh et al. 1994 J. Clin. Invest. 94: 1440-1448; and Wei et al. 1994 Gene Therapy, 1: 261 268).

In certain embodiments, the vectors herein are non-viral vectors for example synthetic gene delivery vehicles or vectors that are not related to a virus particle and that specifically deliver the gene material to the target cells or tissue. Examples of non-viral vectors include liposomes, peptides, nanoparticles, emulsions, or encapsulated two or more phase systems or other suitable preparation. Thus, in certain embodiments a method, kit, or composition involves a non-viral vector with nucleic acid that is loaded and contacted to a tissue or cell. For example a liposome containing naked DNA encoding a membrane-independent CD59 protein having a modified GPI anchor that does not target a membrane, or a gene encoding a membrane-independent CD59 protein having no GPI anchor, is encapsulated in the liposome and the liposome is contacted to the tissue or cell such that the nucleic acid is effectively delivered to the tissue or cell for treatment of a complement-related disease.

Antibodies

The present invention relates also to diagnosing or prognosing presence or progression of macular degeneration and other complement disorders by determining extent of MAC deposition on a retina by immunohistochemistry, using antibodies that are specific for human MAC. The term "antibody" as referred to herein includes whole antibodies and any antigen binding fragment (i.e., "antigen-binding portion") or single chains of these. A naturally occurring "antibody" is a glycoprotein including at least two heavy (H) chains and two light (L) chains inter-connected by disulfide bonds.

As used herein, an antibody that "specifically binds to human MAC" is intended to refer to an antibody that binds to human MAC with a $K_D$ of $5 \times 10^{-9}$ M or less, $2 \times 10^{-9}$ M or less, or $1 \times 10^{-10}$ M or less. For example, the antibody is monoclonal or polyclonal. The terms "monoclonal antibody" or "monoclonal antibody composition" as used herein refer to a preparation of antibody molecules of single molecular composition. A monoclonal antibody composition displays a single binding specificity and affinity for MAC or for a particular epitope of MAC. The antibody is an IgM, IgE, IgG such as IgG1 or IgG4.

Also useful for MAC assay is an antibody that is a recombinant antibody. The term "recombinant human antibody", as used herein, includes all antibodies that are prepared, expressed, created or isolated by recombinant means, such as antibodies isolated from an animal (e.g., a mouse). Mammalian host cells for expressing the recombinant antibodies used in the methods herein include Chinese Hamster Ovary (CHO cells) including dhfr-CHO cells, described in Urlaub and Chasin 1980 Proc. Natl. Acad. Sci. USA 77: 4216-4220, and used with a DH FR selectable marker, e.g., as described in R. J. Kaufman and P. A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. To produce antibodies, expression vectors encoding intact or a portion of the protein of interest are introduced into mammalian host cells, and the host cells are cultured for a period of time sufficient to allow for expression of the antibody in the host cells or secretion of the antibody into the culture medium in which the host cells are grown. Antibodies can be recovered from the culture medium using standard protein purification methods.

Standard assays to evaluate the binding ability of the antibodies toward the target of various species are known in the art, including for example, ELISAs, western blots and RIAs. The binding kinetics (e.g., binding affinity) of the antibodies also can be assessed by standard assays known in the art, such as by Biacore analysis.

General methodologies for antibody production, including criteria to be considered when choosing an animal for the production of antisera, are described in Harlow et al. (1988 Antibodies, Cold Spring Harbor Laboratory, pp. 93-117). For example, an animal of suitable size such as goats, dogs, sheep, mice, or camels are immunized by administration of an amount of immunogen, such as the intact protein or a portion thereof containing an epitope from human MAC, effective to produce an immune response. An exemplary protocol is as follows. The animal is subcutaneously injected in the back with 100 micrograms to 100 milligrams of antigen, dependent on the size of the animal, followed three weeks later with an intraperitoneal injection of 100 micrograms to 100 milligrams of immunogen with adjuvant dependent on the size of the animal, for example Freund's complete adjuvant. Additional intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing human MAC.

The technique of in vitro immunization of human lymphocytes is used to generate monoclonal antibodies. Techniques for in vitro immunization of human lymphocytes are well known to those skilled in the art. See, e.g., Inai et al. May 1993 Histochemistry, 99(5): 335-362; Mulder et al. 1993 Hum. Immunol. 36(3): 186-192; Harada, et al. 1993 J. Oral Pathol. Med., 22(4): 145-152; Stauber, et al. 1993 J. Immunol. Methods 161(2): 157-168; and Venkateswaran, et al. 1992 Hybridoma, 11(6): 729-739. These techniques can be used to produce antigen-reactive monoclonal antibodies, including antigen-specific IgG, and IgM monoclonal antibodies. Any antibody or fragment thereof having affinity and specific for human MAC is within the scope of the assay for MAC deposition provided herein.

The invention herein provides in one embodiment a method of assaying extent of macular degeneration (MD) arising from a complement component in a serum in a model cell system, the method including: exposing a first sample of cells to a sample of the serum and measuring resulting lysis, and comparing extent of lysis to that in a second sample of control cells not so exposed to the serum and otherwise identical, such that the extent of lysis in the first sample compared to that in the second sample is a measure of complement-induced MD.

In other embodiments, the invention provides methods of assaying a potential therapeutic agent for efficacy in treatment of human macular degeneration (MD) in a model cell system, the method including: contacting a first sample of cells to serum and measuring resulting lysis, and contacting a second sample of otherwise identical control cells with serum and a source of human CD59 protein and measuring resulting lysis; and contacting at least a third sample of cells to a candidate therapeutic composition and otherwise identically to serum and measuring lysis, such that the extent of lysis of the third sample compared to that in the first sample and the second sample is a measure of protection by the candidate composition, thereby assaying for a potential therapeutic agent for efficacy in treatment of human MD. The source of CD59 includes pure isolated CD59 without limitation, such as purified from a natural source or made recombinantly and purified, or delivered by a vector such as a viral vector or a nucleic acid vector, the vector encoding the CD59 and capable of expressing CD59 in vivo. In examples herein, contacting with CD59 is achieved by injecting cells or tissues with a vector encoding the CD59 gene.

In an embodiment of these methods, cell lysis is measured by propidium iodide (PI) uptake. PI is commercially available from, for example, Fluka BioChemica (Buchs, Switzerland). PI is an intercalating agent that fluoresces when bound to DNA. PI is membrane impermeant and generally excluded from viable cells, thus PI is commonly used to identify and/or determine the amount of non-living cells in a mixed population.

In other embodiments, the invention provides methods in a model cell system of assaying a serum complement component for prognosis or diagnosis of macular degeneration (MD), the method including: contacting detectably labeled cells with serum from a subject and measuring amount of extracellular and/or intracellular detectable agent for contacted cells; and comparing extracellular and/or intracellular agent in the cells to that in detectably labeled control cells not exposed to the serum and otherwise identical, such that amount of extracellular and/or intracellular agent in the contacted cells is compared to that in the control cells, such that a greater amount of extracellular detectably labeled agent in cells contacted with serum is an indication of prognosis or diagnosis of MD.

In other embodiments, the invention provides methods of assaying a potential therapeutic agent for efficacy in treatment of human macular degeneration (MD) in a model cell system, the method including: contacting a first sample of detectably labeled cells with serum from a subject and measuring amount of extracellular and/or intracellular detectable agent, and contacting a second sample of otherwise identical detectably labeled control cells with serum and a source of human CD59 protein and measuring amount of extracellular and/or intracellular detectable agent; and contacting at least a third sample of detectably labeled cells to at least one candidate therapeutic composition and otherwise identically to serum and measuring amount of extracellular and/or intracellular detectable agent, such that the amount of extracellular and/or intracellular detectable agent of the third sample compared to that in the first sample and the second sample is a measure of protection by the candidate composition, such that a greater amount of extracellular detectably labeled agent is an indication of MD, thereby assaying for a potential therapeutic agent for efficacy in treatment of human MD.

In embodiments of these methods, the detectable agent is, for example, a recombinant vector having a gene capable of expressing a detectable protein, a fluorescent agent, a colorimetric agent, an enzymatic agent, and a radioactive agent.

In certain embodiments, the detectable protein is a fluorescent protein, for example, green fluorescent protein, aequorin, cyan fluorescent protein, DsRed fluorescent protein, enhanced green fluorescent protein, and yellow fluorescent protein. Green fluorescent protein (GFP) and aequorin are bioluminescent compositions isolated from the jellyfish *Aequorea victoria*. When a calcium ion binds to aequorin, the complex breaks down into apoaequorin and a luminescent composition, which emits blue light. Synthetic aequorin is commercially available from Sealite, Sciences (Bogart, Ga.) as AQUALITE®. GFP emits light in the lower green portion of the visible spectrum, and synthetic GFP is commercially available from Clontech (Mountain View, Calif.).

Mutations to the amino acid sequence of GFP have been made to produce derivative amino acid sequences of GFP that fluoresce different colors, for example, cyan fluorescent protein, DsRed fluorescent protein, enhanced green fluorescent protein, and yellow fluorescent protein. Synthetic cyan fluorescent protein, synthetic DsRed fluorescent protein, synthetic enhanced green fluorescent protein, and synthetic yellow fluorescent protein are each commercially available from Clontech (Mountain View, Calif.).

In alternative embodiments, the detectable agent is a fluorescent agent that is not a fluorescent protein, for example, Indocyanine Green, Doxorubicin, Riboflavin, Chlorophyll, and Porphyrin.

Indocyanine Green (ICG) is a tricarbocyanine dye that upon excitation, emits lights at about 800 nm, about 820 nm, about 840 nm or at about 860 nm. ICG is commercially available from H.W.Sands Corp. (Jupiter, Fla.). Doxorubicin is fluorescent and emits light at wavelengths of, for example, about 550 nm, 600 nm, or 650 nm. Doxorubicin is commercially available from Sigma-Aldrich (St. Louis, Mo.). Riboflavin is commercially available from Sigma-Aldrich (St. Louis, Mo.) and is fluorescent, emitting light at a wavelength of, for example, about 450 nm, about 550 nm, about 650 nm, or about 750 nm. Chlorophyll A is a green photosynthetic pigment that emits light at a wavelength of, for example, about 600 nm, about 700 nm, or about 800 nm. Chlorophyll A is commercially available from suppliers such as Sigma Chemical (St. Louis, Mo.) and Turner Designs (Sunnyvale, Calif.). Porphyrin is a heterocyclic macrocycle made from 4 pyrrole subunits linked on opposite sides through 4 methine bridges (=CH—). The extensive conjugated structure of Porphyin makes the compound chromatic, i.e., fluorescent at a wavelength of, for example, about 600 nm, or about 650 nm, or about 700 nm. Porphyrin is commercially available from Sigma-Aldrich (St. Louis, Mo.).

In other alternative embodiments, the detectable agent is an enzymatic agent which is a protein, for example, β-galactosidase or alkaline phosphatase, that can be expressed on a nucleotide vector.

β-galactosidase is a hydrolase enzyme that catalyzes the hydrolysis of β-galactosides into monosaccharides. A luminescent β-galactosidase detection kit is commercially available from Clontech (Mountain View, Calif.). Alkaline phosphatase is a hydrolase enzyme responsible for removing phosphate groups from many types of molecules, including nucleotides, proteins, and alkaloids. A luminescent alkaline phosphatase detection kit is commercially available from Sigma Aldrich (St. Louis, Mo.).

Pharmaceutical Compositions

An aspect of the present invention provides pharmaceutical compositions that include a CD59-encoding nucleic acid or a source of CD59 protein expression. In various embodiments, the CD59 protein includes a membrane-independent CD59 protein. In certain embodiments, the pharmaceutical composition is compounded as an ophthalmologic formulation for administration to the eye and may be compounded to enhance delivery to the fundus, to provide sustained release locally at the retina or otherwise formulated to provide effective treatment of the vessels and/or tissue involved in ocular diseases including macular degeneration. In related embodiments, the pharmaceutical composition is formulated sufficiently pure for administration to a human subject, e.g., to the eye of a human subject. In certain embodiments, these compositions optionally further include one or more additional therapeutic agents. In certain embodiments, the additional therapeutic agent or agents are selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin H, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid.

In other embodiments, the additional agent is a compound, composition, biological or the like that potentiates, stabilizes or synergizes or even substitutes for the ability of CD59 protein to protect cells from MAC deposition. Also included are therapeutic agents that may beneficially or conveniently be provided at the same time as the CD59 protein, such as agents used to treat the same, a concurrent or a related symptom, condition or disease. In some embodiments, the drug may include without limitation anti-tumor, antiviral, antibacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996, the contents of which are herein incorporated by reference herein.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

Therapeutically Effective Dose

Treatment of a complement by methods provided herein involves contacting a tissue or cells with a pharmaceutical composition, for example, administering a therapeutically effective amount of a pharmaceutical composition having as an active agents a nucleic acid encoding a CD59 protein or a source of expression of a CD59 protein, to a subject in need thereof, in such amounts and for such time as is necessary to achieve the desired result. Methods for example include treating AMD by contacting an ocular tissue or cell with CD59 protein or a vector encoding the CD59 protein.

The compositions, according to the method of the present invention, may be administered using any amount and any route of administration effective for treating AMD or other complement-related diseases and conditions. Thus, the expression "amount effective for treating AMD", as used herein, refers to a sufficient amount of composition to beneficially prevent or ameliorate the symptoms of AMD.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., intermediate or advanced stage of AMD; age, weight and gender of the patient; diet, time and frequency of administration; route of administration; drug combinations; reaction sensitivities; and tolerance/response to therapy. Long acting pharmaceutical compositions might be administered hourly, twice hourly, every 3 to four hours, daily, twice daily, every 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model provided herein is also used to achieve a desirable concentration and total dosing range and route of administration. Such information can then be used to determine useful doses and routes for administration in humans.

A therapeutically effective dose refers to that amount of active agent that ameliorates the symptoms or condition or prevents progression of AMD. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50.

Pharmaceutical compositions which exhibit large therapeutic indices are preferred. The data obtained from cell culture assays and animal studies are used in formulating a range of dosage for human use.

The daily dosage of the products may be varied over a wide range, such as from 0.001 to 100 mg per adult human per day. For ocular administration, the compositions are preferably provided in the form of a solution containing 0.001, 0.01, 0.05, 0.1, 0.5, 1.0, 2.5, 5.0, 10.0, 15.0, 25.0, 50.0, 100.0, 250.0, or 500.0 micrograms of the active ingredient for the symptomatic adjustment of the dosage to the patient to be treated.

A unit dose typically contains from about 0.001 micrograms to about 500 micrograms of the active ingredient, preferably from about 0.1 micrograms to about 100 micrograms of active ingredient, more preferably from about 1.0 micrograms to about 10 micrograms of active ingredient. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day. The compositions may be administered on a regimen of for example, one to four or more times per day. A unit dose may be divided for example, administered in two or more divided doses.

Administration of a source of expression of a CD59 protein is administration of a dose of a viral vector or a nucleic acid vector, such that the dose contains at least about 50, 100, 500, 1000, or at least about 5000 particles per cell to be treated. Cell number can be calculated from retinal area in need of treatment by methods known to one of skill in the art of AMD.

Administration of Pharmaceutical Compositions

As formulated with an appropriate pharmaceutically acceptable carrier in a desired dosage, the pharmaceutical composition provided herein is administered to humans and other mammals topically such as ocularly (as by solutions, ointments, or drops), nasally, bucally, orally, rectally, parenterally, intracisternally, intravaginally, or intraperitoneally.

Ocular injections include intra-ocular injection into the aqueous or the vitreous humor, or injection into the external layers of the eye, such as via subconjunctival injection or subtenon injection.

Liquid dosage forms for ocular, oral, or other systemic administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

The invention having now been fully described, it is further illustrated by the following examples and claims, which are illustrative and are not meant to be further limiting.

A portion of this work was published in a paper entitled, "Soluble CD59 Expressed from an Adenovirus In Vivo is a Potent Inhibitor of Complement Deposition on Murine Liver Vascular Endothelium", co-authored by Jarel Gandhi, Siobhan M. Cashman, and Rajendra Kumar-Singh, (PLoS One. 2011; 6(6): e21621), which is hereby incorporated by reference herein in its entirety.

The invention now having been fully described, it is further exemplified by the following examples and claims. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference in their entirety.

EXAMPLES

Compositions that include a nucleic acid encoding a CD59 protein or a source of in vivo expression of CD59 protein are shown by the following Examples to be effective to treat AMD or other complement-related conditions. A humanized murine model of measuring human MAC deposition in vitro and in vivo is shown in the following Examples, and this model is used to measure protection of murine RPE from the deleterious deposition of human MAC by a vector that expresses human CD59 protein.

Example 1

Adenovirus Vector Constructs

Human CD59 cDNA was obtained from the American Type Tissue Culture Collection (ATCC, Manassas, Va.) and PCR amplified using a forward primer containing an XhoI site (underlined; 5'ccccctcgagtggacaateacaatggg3'; SEQ ID NO:1) and a reverse primer with an EcoRV site (underlined; 5'ccccctcgagtcaacggggagtttgggagaag3'; SEQ ID NO:2).

The PCR product was gel purified and, after XhoI/EcoRV digestion, cloned into XhoI/EcoRV digested pShCAG (constructed by cloning a SalI/BamHI fragment of pCAGEN into XhoI/BglII digested pShuttle) generating pShCA-GCD59. Automated sequencing confirmed that the CD59 sequence had been introduced into the generated plasmid. This shuttle plasmid was then used to produce the adenovirus vector using protocols published in Klein et al. 2007 Ophthalmology 114: 253-262, and van Leeuwen et al. 2003 Eur. J. Epidemiol. 18: 845-854. pShCAGCD59 was linearized with PmeI, gel purified and recombined with pAdEasy-1 by co-transformation of *Escherichia coli* BJ5183 cells. The recombined plasmid was linearized with PacI, transfected into the human embryonic retinoblast (911) cell line and the resulting vector (AdCAGCD59) was purified using the adenovirus purification kit Adenopure (Puresyn, Inc., Malvern, Pa.).

Control vector AdEMPTY was generated similarly by recombining the PmeI linearized pSHCAG with pAdEasy-1. The AdCAGGFP control vector is described in Johnson et al. 2000 Exp. Eye Res. 70: 441-449.

Example 2

Contacting Cell Lines with Adenovirus Expressing CD59

Human embryonic retinoblast cell line 911 was maintained in Dulbecco's Modified Eagle's Medium (DMEM) supplemented with 10% fetal bovine serum (FBS) and mouse hepatoma cell line hepa-1c1c7 (ATCC, Manassas, Va.) in α-MEM supplemented with 10% FBS. Cells were cultured in a humidified incubator at 37° C. under 5% $CO_2$: 95% air atmosphere.

For Western blot analysis or the human serum cell lysis assay hepa-1c1c7 ($1.2 \times 10^6$) cells were contacted and for CD59 immunocytochemistry or the human serum MAC deposition assay $2.5 \times 10^4$ hepa-1c1c7 cells were contacted with either AdCAGGFP or AdCAGCD59 vectors at multiplicities of infection of the virus particles per cell as indicated, or control cells were not so contacted. Adenovirus vector contacting to cells was performed in media with 2% FBS. Three days after contacting, cells were further treated as described in Examples herein. While specific conditions are described herein, equivalent conditions of media, temperature, etc., to achieve effective treatment of cells or tissues with CD59 are within the scope of the methods herein.

Primary Mouse RPE cells were harvested from eyes of sacrificed six to ten week old C57B1/6J mice. After removing each of the anterior chamber, lens and retina as described below, eyecup tissues were incubated in 200 μl 0.25% trypsin-EDTA in 1.5 ml eppendorf tubes for 40 to 50 minutes at 37° C. Eyecup tissues were subsequently transferred to a 60 mm cell culture plate containing α-MEM supplemented with 10% FBS. The RPE cells were gently scraped with a pipet tip, and the RPE sheets were aspirated using a 200 μl pipet and transferred to an eppendorf tube. After dispersing the RPE sheets by pipeting the media several times, cells were counted and about $3 \times 10^4$ cells (generally the yield obtained from one eye) were seeded in one chamber of a poly-D-lysine-coated chamberslide (Becton Dickinson, Franklin Lakes, N.J.). After one week in culture, cells were used as described in Examples herein. Contacting cells with adenovirus vector was performed in media with 2% FBS.

Example 3

Western Blot Analysis

Cells were lysed in 50 mM Tris-HCl, pH 8.0/150 mM NaCl/0.1% sodium dodecyl sulfate/1% Triton X-100 containing 2% (v:v) protease inhibitor cocktail (Sigma-Aldrich, St. Louis, Mo.). Media from cells were collected, centrifuged, and passed through a 0.22 μm filter or other filter as indicated in the figures, to remove remaining cell debris and media were concentrated 10× using a Biomax centrifugal filter with a 10,000 Dalton pore size (Millipore Corporation, Billerica, Mass.). Lysates were analyzed by gel electrophoresis under non-reducing conditions on a 15% Tris-glycine SDS-PAGE gel (Bio-Rad Laboratories, Hercules, Calif.) and proteins were transferred to a polyvinylidene fluoride (PVDF) membrane (Millipore, Billerica, Mass.). Following blocking in 5% (w:v) skim milk (Becton Dickinson, Sparks, Md.), the membrane was probed for human CD59 using a mouse anti-human CD59 monoclonal antibody (1:1000 dilution; Clone Mem-43; Abeam, Cambridge, Mass.), followed by a secondary antibody horseradish peroxidase-conjugated goat anti-mouse antibody (1:10,000 dilution; Jackson Immunoresearch, West Grove, Pa.). Following stripping and blocking as described above, the same membrane was probed for β-Actin with a mouse anti-β-actin monoclonal antibody (1:5,000 dilution; Clone AC-15; Sigma-Aldrich, St. Louis, Mo.). Secondary detection was performed as described above.

Example 4

Human Scrum Cell Lysis Assay

Normal human serum (NHS) was purchased in lyophilized form from Sigma (St. Louis, Mo.) and reconstituted (per manufacturer instructions) with one milliliter (ml) of cold sterile deionized water to obtain a volume of serum equal to that of the human plasma from which the powder was obtained. The resulting human serum lots having a hemolytic titer of 43 $CH_{50}$ units/ml or 74 $CH_{50}$ units/ml respectively (determined by the manufacturer using the method of Kabat and Mayer) were aliquoted and stored at −80° C. The first lot with a hemolytic titer of 43 $CH_{50}$ units/ml was used in experiments with hepa-1c1c7 cells. The second lot, with a hemolytic titer of 74 $CH_{50}$ units/ml, was used in the other experiments.

For the human serum cell lysis assay, single cell suspensions of contacted cells, i.e., including control cells not contacted with vector, or adenovirus contacted hepa-1c1c7 cells in a total volume of 500 μl were used. Following removal of media, cells were washed twice with 1× phosphate buffered saline (PBS) and after brief trypsinization (0.25% trypsin-EDTA, 4-6 mins), harvested with 1×PBS containing 0.5% FBS. Cells were collected by centrifugation at 4° C. and re-suspended in ice-cold gelatin veronal buffer with $Ca^{2+}$ and $Mg^{2+}$ ($GVB^{++}$, Complement Technology, Tyler, Tex.). Cells were counted on a hemacytometer and $5\times10^5$ cells were aliquoted into eppendorf tubes. Normal human serum (NHS) or heat inactivated (56° C. for one hour) normal human serum (HI-NHS) was added to cells, and the cell suspensions were incubated at 37° C. for one hour with gentle rotatory shaking. Cell lysis was determined by the propidium iodide (PI) exclusion method followed by FACS analysis.

Shortly prior to FACS, one microliter of PI (1 mg/ml; Fluka BioChemica, Buchs, Switzerland) was added to a cell suspension and 25,000 events per sample were counted on a FACSCalibur (Becton Dickinson, Franklin Lakes, N.J.). Results were analyzed using the CellQuest Pro software (Becton Dickinson, Franklin Lakes, N.J.) and percent cell lysis was calculated using the formula shown below.

% Cell Lysis=[1-(% live cells in HI-NHS/% live cells in NHS)]×100

Example 5

MAC Deposition Assay in Cell Culture

Mouse hepa-1c1c7 cells were cultured for three days, and were contacted with AdCAGGFP (negative control), or AdCAGCD59, in poly-D-lysine-coated chamberslides (Becton Dickinson, Franklin Lakes, N.J.) and were washed twice with 1×PBS. Cells were then incubated with 10% (v:v) NHS or HI-NHS in $GVB^{++}$ (Complement Technology, Tyler, Tex.) at 37° C. for one, three, five, seven or ten minutes.

Primary mouse RPE cells were incubated with or without 25 µg/ml goat anti-mouse emmprin antibody (R&D Systems, Minneapolis, Minn.) in $GVB^{++}$ (Complement Technology, Tyler, Tex.) for one hour and either washed and fixed (for emmprin immunocytochemistry) or were treated for the MAC deposition assay followed by addition of NHS or HI-NHS (final concentration 50%) for four or seven minutes. Thereafter cells were washed three times with ice cold 1×PBS and fixed with 3.7% formaldehyde (MP Biomedicals, Solon, Ohio) in 1×PBS for 15 minutes. Cells were washed another three times with 1×PBS to remove remaining fixative and stored in 1×PBS at 4° C. until immunocytochemical analysis, as described in Examples herein.

Example 6

Immunocytochemistry/Immunohistochemistry

Fixed cells or tissues described above were incubated with primary mouse monoclonal antibodies specific to human CD59 (clone M-43) or human C5b-9 (clone aE11) (each at 1:50 dilution, Abcam, Cambridge, Mass.) in 1×PBS containing 6% (w:v) normal goat serum (Jackson Immunoresearch, West Grove, Pa.) for 2.5 hours with gentle rotatory shaking. Secondary detection was performed using a Cy3 conjugated goat anti-mouse antibody (1:400 dilution; Jackson Immunoresearch, West Grove, Pa.) for 1.5 hours in a dark chamber.

For RPE65 immunostaining, primary RPE cells were pre-blocked and permeabilized in 1×PBS containing 6% (w:v) normal goat serum (Jackson Immunoresearch, West Grove, Pa.) and 0.25% (v:v) Triton X-100 (Fisher Bio-reagents, Fair Lawn, N.J.) for one hour. A mouse anti-RPE65 antibody was then applied and primary and secondary detection were performed as above except that the antibody and washing solutions contained 0.25% (v:v) Triton X-100 (Fisher Bio-reagents, Fair Lawn, N.J.).

For mouse emmprin staining, goat anti-mouse emmprin antibody treated and fixed cells and tissues were blocked in 1×PBS containing 6% (w:v) normal donkey serum (Jackson Immunoresearch, West Grove, Pa.) for one hour and secondary detection was performed using a Cy3-conjugated donkey anti-goat antibody (1:400 dilution; Jackson Immunoresearch, West Grove, Pa.) in 1×PBS containing 6% (w:v) normal donkey serum for 1.5 hours.

Example 7

Trypan Blue Exclusion Assay

Cells were treated as for the MAC deposition assay in cell culture as described in Examples above, except that after washing to remove the serum, cells were incubated in 0.1% trypan blue solution for five minutes. Cells were subsequently washed twice with 1×PBS and fixed as described in Examples above.

Example 8

Subretinal Injections

Mice (C57B1/6J) were purchased from Jackson Laboratories (Bar Harbor, Me.), bred and maintained in a twelve-hour light-dark cycle. Mice were anesthetized by intraperitoneal injection of xylazine (10 mg/ml)/ketamine (1 mg/ml). Subretinal injections were performed as described in Anderson 2002 Am J Ophthalmol. 134: 411-431, using the transcleral-transchoroidal approach with a 32-gauge needle attached to a five microliter (µl) glass syringe (Hamilton, Reno, Nev.). One microliter of a control mixture of nine parts AdEMPTY and one part AdCAGGFP (total of $3\times10^8$ vector particles; control) or of a mixture of nine parts AdCAGCD59 and one part AdCAGGFP (total of $3\times10^8$ vector particles) was injected into each subject mouse.

Example 9

MAC Deposition on RPE and Cornea

Six days after administering injection, mice were sacrificed by carbon dioxide inhalation and eyes were harvested and placed in 1×PBS containing penicillin (100 U/ml) and streptomycin (100 U/ml). A circular incision was made 1-2 mm posterior to the ora serata and the entire anterior chamber including the lens was carefully removed. After making a small incision at the base of the optic nerve to cut the ganglionic axons, the retina was removed and the eyecup tissue was either fixed immediately in 4% paraformaldehyde in phosphate buffer (pH 7.4) overnight (for CD59 immunohistochemistry) or incubated with 25 µg/ml goat anti-mouse emmprin antibody (R&D Systems, Minneapolis, Minn.) in cold $GVB^{++}$ (Complement Technology, Tyler, Tex.) at 4° C. for one hour.

Eyecup tissues were then either washed three times with cold PBS and were fixed for emmprin immunohistochemistry. For MAC deposition assay, an equal volume of NHS or HI-NHS (final concentration 50%) was added to the eyecup tissues which were then incubated at 37° C. for 15 minutes, were washed three times with cold PBS and were fixed.

Cornea tissues were harvested from uninjected mice, the iris was removed and the corneas cultured in 300 μl of DMEM with 2% FBS. Corneas were contacted with $1.5 \times 10^9$ vector particles of AdCAGGFP (negative control) or the AdCAGCD59 vector. Three days following harvesting/contacting, each of untreated corneas (negative control), AdCAGGFP contacted corneas (negative control) and AdCAGCD59 contacted corneas was mixed with anti-mouse emmprin antibody as with eyecup tissues, and each was either washed and fixed (for emmprin immunohistochemistry), or was contacted with 50% NHS or HI-NHS for 20 minutes and then washed and fixed (for the MAC deposition assay). Prior to immunohistochemistry, tissues were washed three times for ten minutes each with 1×PBS to remove remaining fixative.

Example 10

Figure 1A:
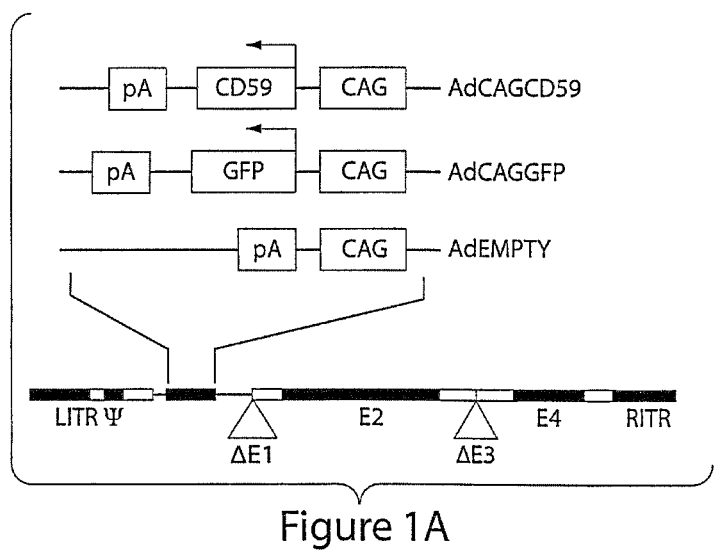
FIG. 1 panel A is a drawing showing constructs AdCAGCD59 serotype 5 adenovirus vector containing a gene encoding human CD59 under control of the chicken beta actin (CAG) promoter, and of two control adenovirus vectors, AdCAGGFP expressing GFP also regulated by the CAG promoter, and negative control vector AdEMPTY. Symbols used: pA, polyadenylation signal; CAG, cytomegalovirus chicken β-actin β-globin promoter; Ψ, Ad packaging signal; ITR, adenovirus inverted terminal repeat; Δ, deleted; E, early region labels.
Figure 1B:
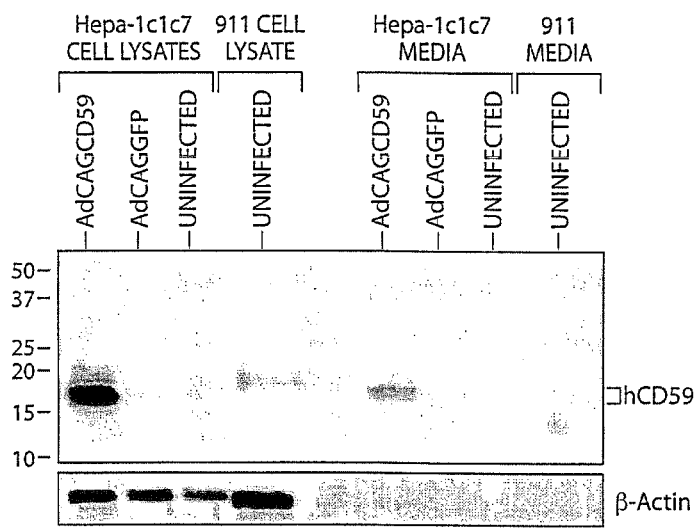
Figure 1C:
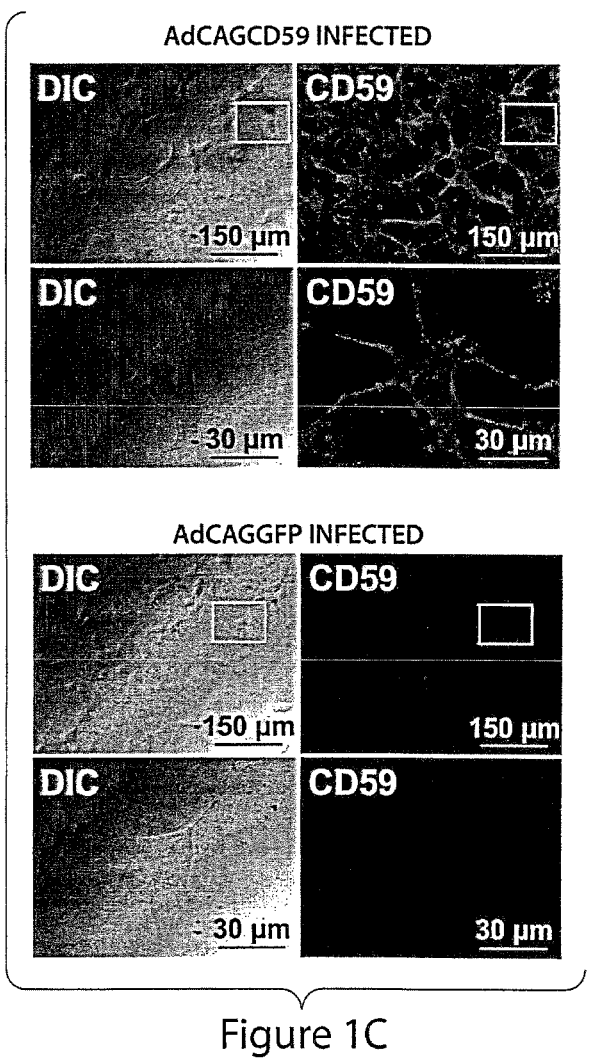
Figure 2A:
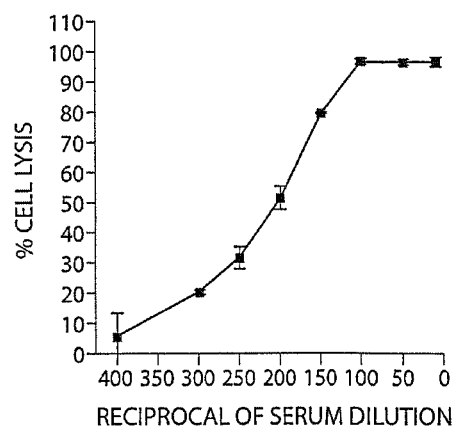
FIG. 2 is a set of graphs showing functional activity of human CD59 expressed in cells contacted with AdCAGCD59 vector.
Figure 2B:
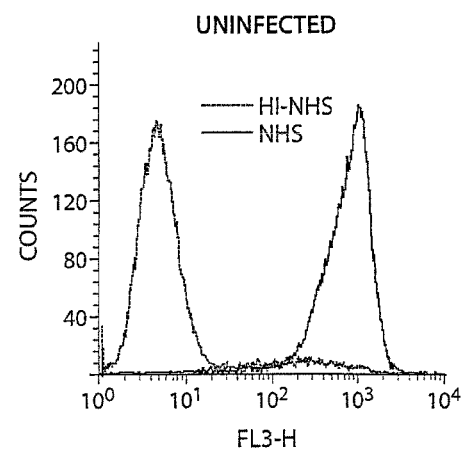
Figure 2C:
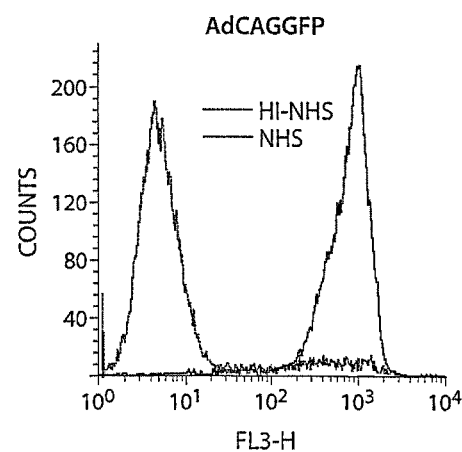
Figure 2D:
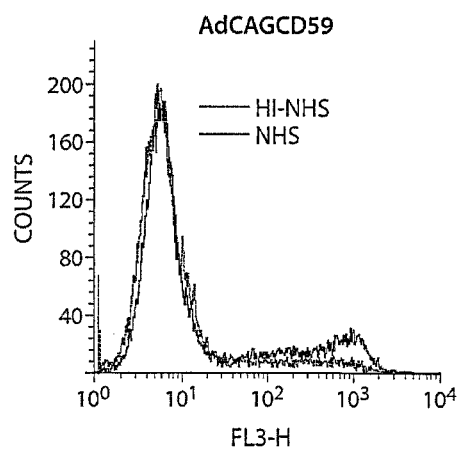
Figure 2E:
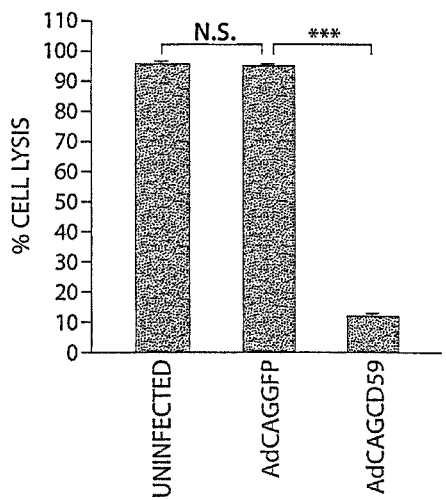
Figure 2F:
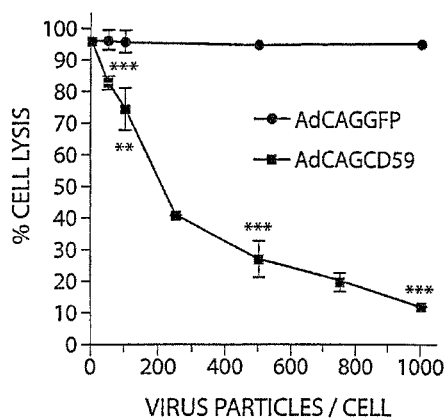

Vector Constructs and Human CD59 Expression in Vector Contacted Hepa-1c1c7 Cells To deliver human CD59 (hCD59) to murine RPE and retina in vivo, a first generation serotype 5 adenovirus containing hCD59 cDNA under control of chicken beta actin (CAG) promoter (AdCAGCD59 vector; FIG. 1 panel A) was produced. Two negative adenovirus control vectors were also constructed, AdCAGGFP expressing GFP under control of the CAG promoter, and AdEMPTY (FIG. 1 panel A). These vectors were constructed to have a deletion in region E1 of adenovirus, and are therefore replication deficient outside of the packaging cells.

Human CD59 is an 18-21 kDa glycosylphosphatidylinositol (GPI)-anchored membrane protein. To analyze expression of the protein, mouse hepa-1c1c7 cells were contacted with a multiplicity of 1000 vector particles (vp/cell) of the purified AdCAGCD59 or control vector. Cell lysates were analyzed by Western blotting using a monoclonal antibody to hCD59, and the presence of hCD59 was observed in cell lysates of AdCAGCD59 contacted cells (FIG. 1 panel B). No CD59 protein was detected in lysates of cells contacted with the control vector (AdCAGGFP, negative control) or control cells not contacted with vector (negative control; FIG. 1 panel B).

Endogenous hCD59 was detected in human embryonic retinoblast (911) cell lysates (FIG. 1 panel B), however this signal was much weaker compared to the signal from the AdCAGCD59 contacted mouse cells. The slight shift in electrophoretic mobility between the endogenous hCD59 detected in 911 cell lysates and the recombinant hCD59 detected in AdCAGCD59 contacted mouse cell lysates may be due to differences in protein modification; for example, variation in protein glycosylation pattern in the two cell lines.

Immunostaining of non-permeabilized AdCAGCD59 contacted mouse hepa-1c1c7 cells using the anti-hCD59 antibody showed expression and localization of hCD59 on the cell membrane (FIG. 1 panel C) and revealed that essentially 100% of cells were expressing the protein. Stain was not observed on cells contacted with the negative control vector. Additional controls included immunocytochemistry of untreated cells and omission of the primary antibody during immunocytochemistry of AdCAGCD59 contacted cells, and results obtained using these controls were negative.

Example 11

Adenovirus Treatment with hCD59 by Vector Contact Protects Mouse Cells from Human Complement Mediated Cell Lysis To test the functional activity of hCD59 expressed from the AdCAGCD59 vector, human serum cell lysis assays were performed on mouse hepa-1c1c7 cells. Cell suspensions were incubated with NHS or HI-NHS (as a control for non-complement specific lysis) to expose the cells to complement, and percent cell lysis was determined by uptake of PI as detected and quantified by FACS analysis.

Effect of concentration of serum on the extent of lysis of control untreated cells was initially investigated (FIG. 2 panel A). Mouse hepa-1c1c7 cells effectively activated human complement, and a serum concentration as low as 0.5% (1/200 dilution) was observed to lyse greater than 50% of cells. It was observed that lysis of cells was serum concentration dependent and the function appeared to be sigmoidal (FIG. 2 panel A). The lowest serum concentration tested that resulted in maximal cell lysis was 1% (1/100 dilution; cell lysis was 96.06%±0.87%). This serum concentration was used in subsequent cell lysis Examples with cells contacted with adenovirus vector.

Cells were contacted with 1000 vp/cell of the AdCAGCD59 or the negative control AdCAGGFP vector and 65 hours after contacting, the cells were harvested and used in human serum cell lysis experiments. Adenovirus amounts used herein did not result in cell toxicity as observed by microscopy or as detected by PI uptake followed by FACS, and by comparison with data obtained from cells contacted with the two vectors and from control untreated cells as shown herein. It was observed that cell lysis of contacted cells incubated in HI-NHS was minimal and was similar to that of cells not contacted with a vector (control) incubated with HI-NHS (FIG. 2 panels B, C and D). Cells transfected with the AdCAGCD59 vector were significantly protected, as complement mediated cell lysis was reduced (about eight-fold) to 12.29%±0.18% (cell lysis is an indication of cell killing and an inverse measure of cell survival; FIG. 2 panels B, D and E).

In contrast, mouse cells contacted with the negative control AdCAGGFP vector were not protected, i.e., remained susceptible to human complement, with extent of complement mediated cell lysis observed at 95.27%±0.01% of cells (FIG. 2 panels C and E). Similarly, it was observed that untreated mouse cells were susceptible to human complement and cell lysis (FIG. 2 panels A, B and E). Transfection with control vector AdCAGGFP, by contrast, did not protect cells, as the extent of lysis observed was 95.27%±0.01% (FIG. 2 panels C and E), similar to that observed for control cells (FIG. 2 panels B and E). These data show that protection was due to expression of hCD59 rather than adenovirus contact per se.

Protection of cells from lysis was obtained herein by expression of human CD59 in cells contacted with AdCAGCD59 vector. It was further observed that protection was dependent on the multiplicity of AdCAGCD59 vector administered. Administering 250 vp/cell and 500 vp/cell of AdCAGCD59, respectively, inhibited cell lysis by over 50% and 70%, respectively (FIG. 2 panel F). In contrast, AdCAGGFP contacted cells were susceptible to lysis regardless of multiplicity of vector administered. Thus, expression of recombinant hCD59 from the AdCAGCD59 vector significantly protected the mouse cells from human complement mediated cell lysis.

Example 12 hCD59 Protein Protects Mouse Cells from Human MAC Deposition

Data in Examples above show that incubation of mouse hepa-1c1c7 cells with normal human serum led to complement activation and extensive cell lysis, and that this lysis was efficiently inhibited when recombinant human CD59 was expressed in these cells.

Examples were performed to determine whether recombinant human CD59 expressed by adenovirus contacted mouse cells would prevent formation of the C5b-9 complex in an in vitro MAC deposition assay developed for this purpose.

Figure 3A:
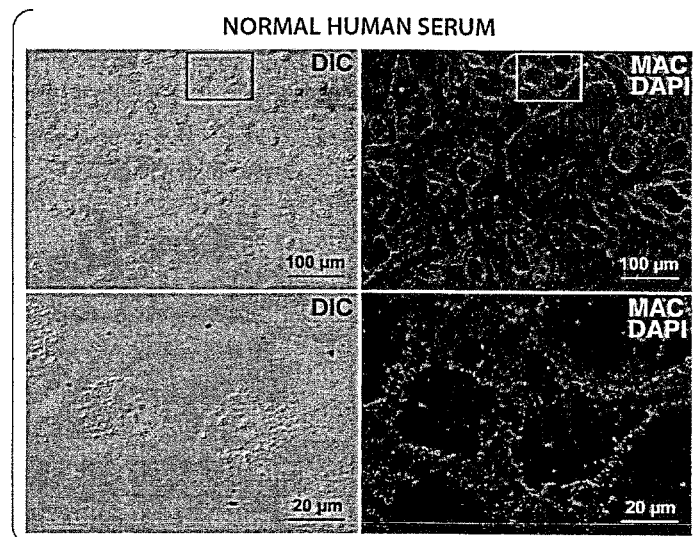
FIG. 3 panels A and B are each a set of four photomicrographs showing that mouse cells are susceptible to C5b-9 deposition when exposed to NHS.
Figure 3B:
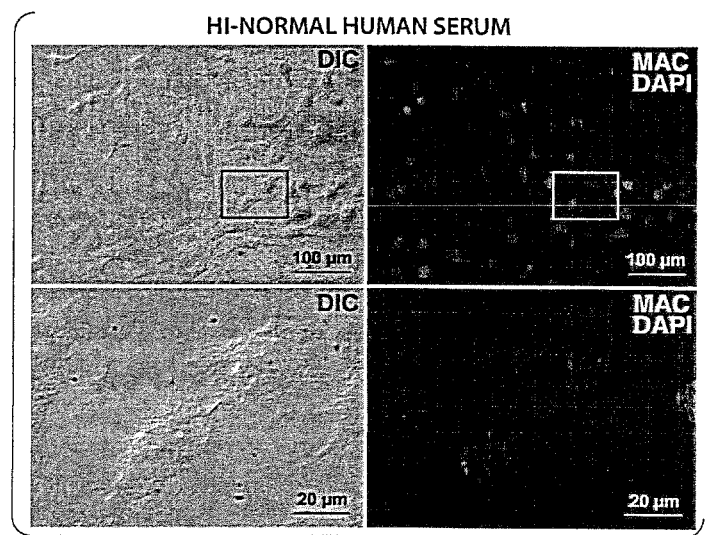
Figure 3C:
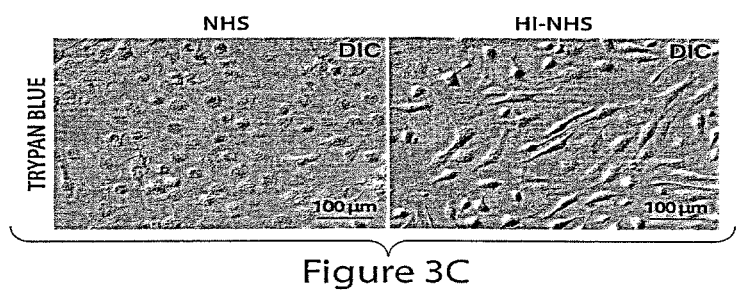

Mouse cells in poly-D-lysine coated chamberslides were incubated with 10% NHS or HI-NHS in GVB$^{++}$ at 37° C. for one to ten minutes and subsequently washed and fixed. Incubation of these cells with NHS for five minutes caused significant changes in cell morphology (FIG. 3 panel A, DIC visualization of cells). Cells showed deleterious effects as cells lost their extensive cytoplasmic processes and became round and granular. In contrast, these effects were not observed with cells incubated with HI-NHS (FIG. 3 panel B, DIC visualization of cells) in which complement is inactivated.

Immunocytochemical analysis using a monoclonal antibody directed to a neo-epitope on the C5b-9 complex revealed extensive membrane staining at the borders of cells exposed to NHS confirming deposition of the MAC on these cells (FIG. 3 panel A). Almost no MAC staining was not observed on cells exposed to HI-NHS (FIG. 3 panel B). Control samples included immunocytochemistry of untreated cells (not incubated with human serum) as well as omission of the primary antibody during immunocytochemistry of NHS contacted cells, both of which controls yielded negative data. Under conditions of exposure to the complement in human serum, lysis of a substantial amount of the NHS exposed cells was shown also by trypan blue staining (FIG. 3 panel C). No lysis was observed on HI-NHS exposed cells as indicated by the absence of trypan blue uptake by these cells (FIG. 3 panel C).

Figure 4A:
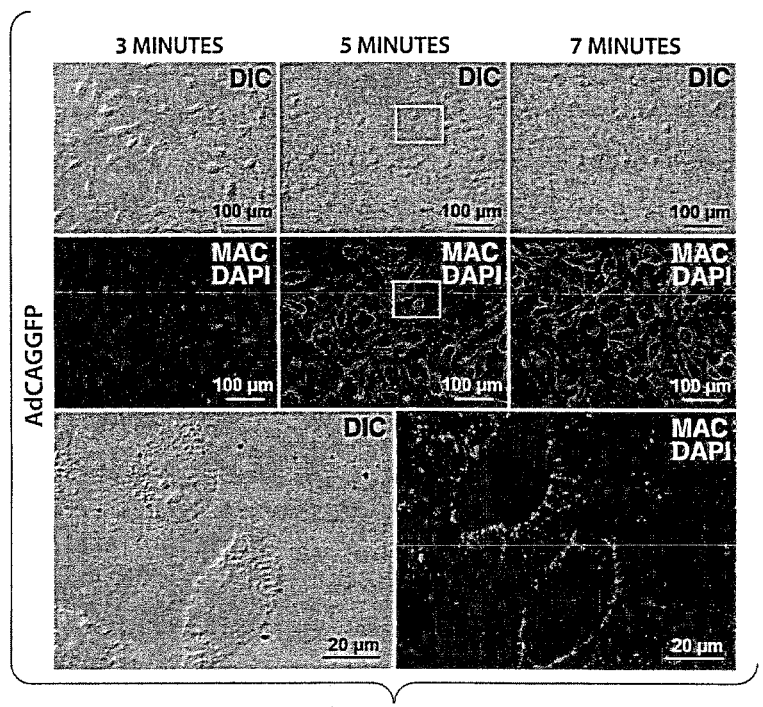
FIG. 4 panel A is a set of photomicrographs of mouse hepa-1c1c7 cells contacted with the control vector AdCAG-GFP and then incubated with NHS for three, five, and seven minutes, and visualized by several methods. The top row shows cells visualized by DIC; the middle row shows the same cells visualized by MAC/DAPI; and the lower row show increased magnification of the highlighted portions of the photomicrographs at five minutes. The cells showed increasing lysis and loss of normal morphology during the time course NHS incubation, after five minutes and seven minutes. Images are representative of three independent experiments for each type of serum tested.
Figure 4B:
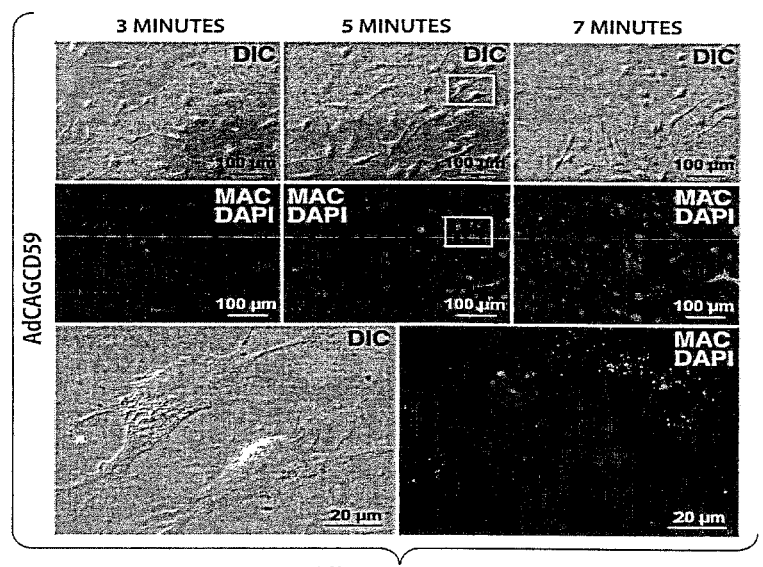
Figure 4C:
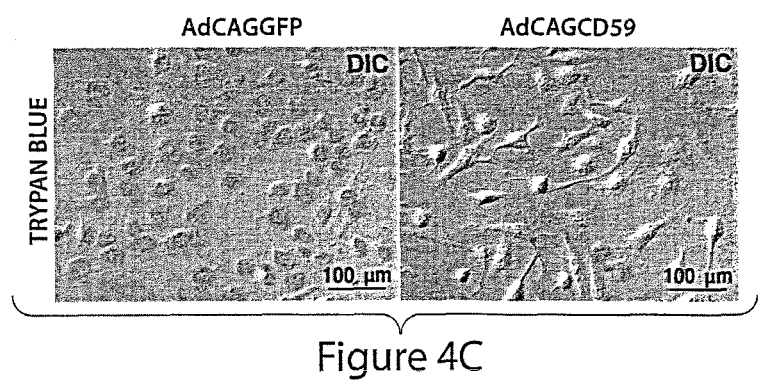

Transfecting the mouse hepa-1c1c7 cells with 1000 vp/cell of the AdCAGCD59 vector was found to significantly protect these cells from human MAC deposition and eventual lysis (FIG. 4 panels B and C). Following exposure to NHS for five minutes, these contacted cells maintained their normal morphological characteristics (FIG. 4 panel B, DIC). Immunocytochemistry using anti-MAC antibody showed almost complete absence of MAC staining (FIG. 4 panel B), and cell lysis was efficiently inhibited as indicated by the absence of trypan blue staining (FIG. 4 panel C). In contrast, cells transfected with the negative control vector expressing GFP were not protected from MAC deposition following five minutes of NHS exposure. Morphological changes (FIG. 4 panel A, DIC), MAC immunostaining (FIG. 4 panel A) and cell lysis (FIG. 4 panel C) of these cells were similar to that observed for untreated control cells (control; FIG. 3 panels A and C), i.e., characteristic of MAC deposition and cell lysis.

Figure 5:
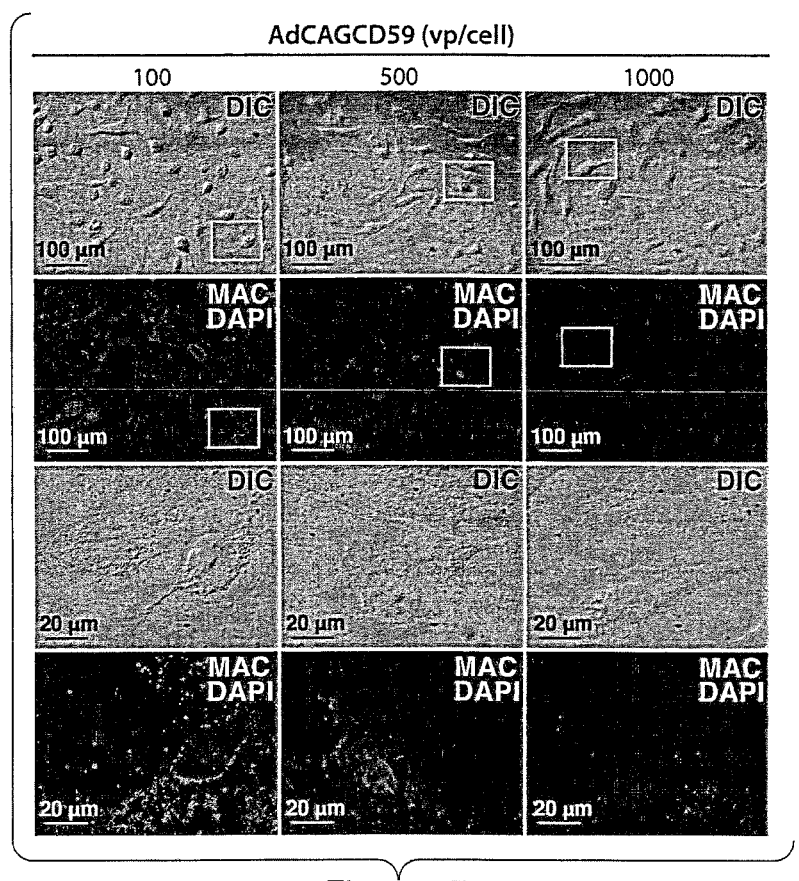
FIG. 5 is a set of photographs showing the effect on cells of pretreatment at different multiplicities of vector particles per cell (vp/cell) of vector AdCAGCD59 particles per cell, at two magnifications (see distance bars), on survival with NHS for five minutes. Left column: cells treated with 100 vp/cell and five minutes of NHS treatment, visualized under four conditions. Middle column: cells treated with 500 vp/cell and five minutes of NHS treatment. Right column: 1000 vp/cell and five minutes of NHS treatment. These photomicrographs show that MAC immunostaining was reduced in cells contacted at higher multiplicities with AdCAGCD59 vector. Cells contacted at higher vector multiplicities further show a greater percent of normal morphologies.
Figure 6A:
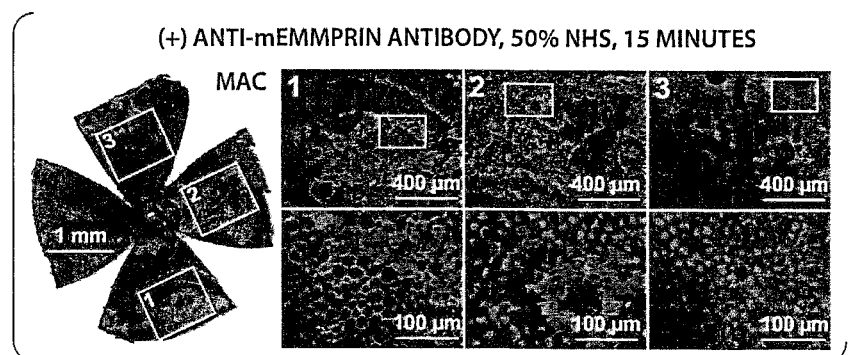
FIG. 6 is a set of photomicrographs of murine eyecups (panels A, B, and C) and primary murine RPE cells (panels D and E) incubated with (+) or without (−) a complement activating anti-mouse emmprin antibody (indicated anti-mEmmprin antibody in the figures), followed by treatment as indicated with NHS or control HI-NHS for time periods shown in the figure. Eyecups and RPE cells were tested for human MAC deposition. Primary RPE cells were labeled with DAPI. Images are representative of at least three independent experiments each for set of eyecups (n=4 eyecups for each condition) and each set of primary RPE cells.
Figure 6B:
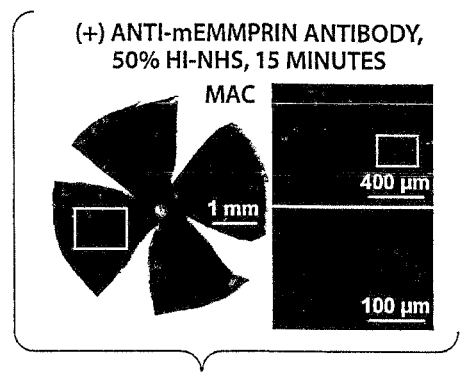
Figure 6C:
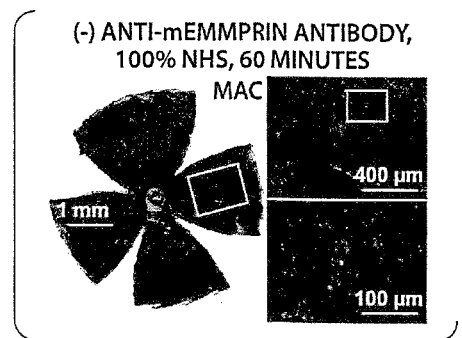
Figure 6D:
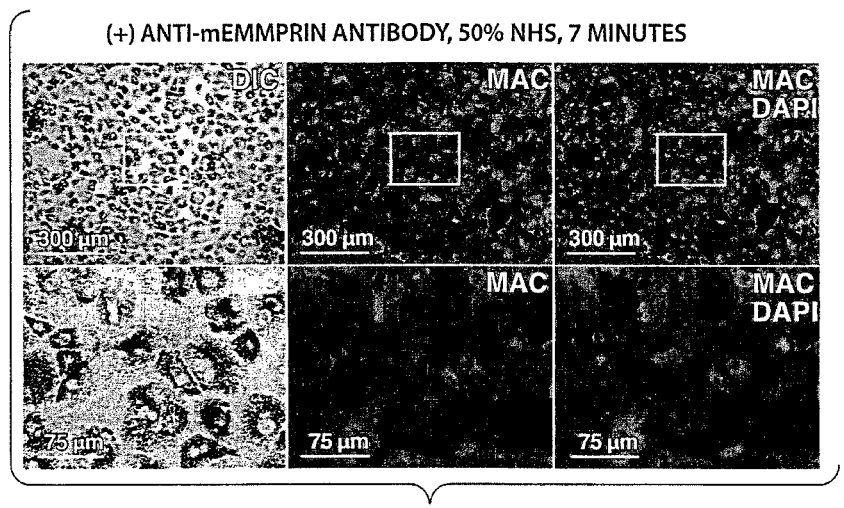
Figure 6E:
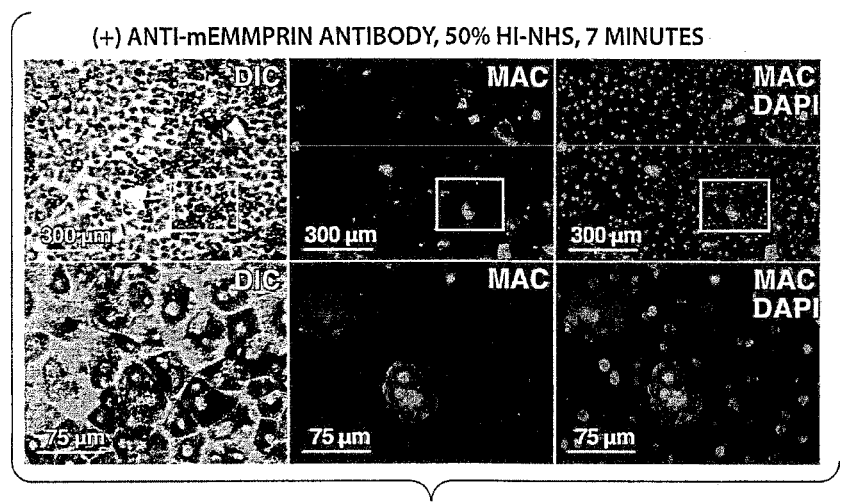

It was observed that MAC staining was present on even a few of the AdCAGCD59 contacted cells following seven minutes of NHS treatment (FIG. 4 panel B) and this number increased after ten minutes of serum treatment. Following seven minutes of NHS treatment, MAC staining of AdCAG-GFP contacted cells (FIG. 4 panel A) was significantly stronger than of AdCAGCD59 pre-contacted cells (FIG. 4 panel B). Following ten minutes of serum treatment almost all AdCAGGFP contacted cells were detached from the cell culture slide due to complete lysis, while only a few cells contacted with AdCAGCD59 vector showed any changes or MAC deposition. Furthermore, the pattern of MAC immunofluorescence indicated the extent of cell membrane damage, with strong punctate staining delineating cell borders correlating with greater damage to cells (FIG. 3 panel A, FIG. 4 panel A and FIG. 5), and more diffuse staining extending throughout the cell membrane correlating with cells that appeared to be intact (FIG. 4 panel B and FIG. 5). MAC deposition on untreated control cells and on AdCAG-GFP contacted cells was rapid and punctate. Diffuse staining, indicating lower less damaging levels of MAC deposition, was seen primarily on AdCAGCD59 transfected cells (FIG. 4 panel B and FIG. 5).

The different patterns of MAC immunostaining was more readily observed when cells were pre-contacted at lower multiplicities of the AdCAGCD59 vector. Following five minutes of NETS exposure, cells contacted with 100 or 500 vp/cell showed more MAC immunostaining compared to cells contacted with 1000 vp/cell (FIG. 5, especially greater magnification in the lower left photomicrograph). Contacting cells with even these lower multiplicities of the hCD59 expressing adenovirus yielded significant protection of the cells from MAC deposition (see FIG. 4 panel A for comparison).

Example 13

Model of Human MAC Deposition on Murine RPE, Primary RPE Cells and Corneal Endothelium A MAC deposition assay was developed in order to use murine ocular tissues to assay extent of AMD damage or potential for AMD, and to use to screen agents to treat or prevent AMD.

Eyecup tissues were harvested from C57B1/6J mice and exposed to various concentrations of NHS or HI-NHS. Immunohistochemical analysis with the anti-human C5b-9 antibody was followed by an appropriate Cy3 conjugated secondary antibody. The data showed no fluorescent signal on the RPE, even when eyecup tissues were contacted with a concentration of NHS as high as 50%. Contacting with 100% NHS resulted in occasional scattered weak staining (FIG. 6 panel C). The inconsistent weak signal obtained was not useful for purposes of any development. Further, attempts to use the cornea to test the potential of adenovirus delivered hCD59 to protect murine ocular tissues from human MAC deposition also were not successful. No MAC deposition, at any NHS concentration used, was detected on the corneal endothelium, which is known to be efficiently transduced by adenoviruses. Strong MAC immunostaining was always detected on the corneal epithelium.

The MAC deposition assay was preformed on primary mouse RPE cells in order to further explore the absence of MAC deposition on murine RPE cells following exposure to human serum, and to determine whether the extracellular matrix on the ocular tissues was interfering with accessibility of complement proteins to the RPE or endothelial cell surface. RPE cells were identified by presence of typical pigmentation, characteristic morphology and routine immunostaining for the RPE cell marker, RPE65 (FIG. 7; top row shows bright field illuminated cells, third row shows staining with anti-RPE65). As with tissues, weak and inconsistent MAC immunostaining was observed on passage 0 mouse RPE cells upon exposure to 50% NHS (FIG. 8 panel C).

The absence of extensive MAC deposition on the RPE and corneal endothelium upon exposure to NHS could be due to inefficient complement activation and/or enhanced protection by murine complement regulatory proteins expressed on the surface of these cells. To determine if complement activation on murine RPE could be enhanced, an antibody against the extracellular domain of mouse emmprin, which is an abundantly expressed membrane protein on RPE as well as corneal endothelium was next used. An anti-mouse emmprin antibody produced in goat was selected to avoid potential cross-reactivity with the secondary antibody (Cy3-conjugated goat anti-mouse IgG and IgM) used for MAC immunostaining.

Incubation of mouse eyecup tissues or cornea tissues with the anti-mouse emmprin antibody followed by exposure to NHS (final concentration 50% for 15 minutes eyecup tissues, or 20 minutes cornea tissues at 37° C.) yielded extensive, bright MAC immunostaining of the RPE dissected tissue (FIG. 9 panel A) and corneal endothelium (FIG. 9 panel C). This immunostaining was a result of complement-activated MAC deposition, as addition of control HI-NHS rather than NHS, eliminated the staining; MAC immunostaining was not observed with use of HI-NHS (FIG. 9 panels B and D). The RPE monolayer contacted with NHS often appeared convoluted and various patterns of staining were observed due to different amounts of MAC deposition and various amounts of cell damage. Additional negative controls included MAC immunostaining of eyecup tissues and cornea tissues contacted with the anti-mouse emmprin antibody, but not with human serum as well as omission of the primary antibody during immunohistochemistry of eyecup tissues and cornea tissues contacted with both the anti-mouse emmprin antibody and NHS, and no staining was observed with these controls.

Similar results were also obtained with primary passage 0 mouse RPE cells (FIG. 8 panels A and B). Upon incubation with the anti-emmprin antibody and exposure to 50% NHS for four minutes, cell destruction was observed on the RPE cells (FIG. 8 panel A). By seven minutes of NHS exposure, almost all cells had detached from the slide. Occasionally only cell aggregates of high confluence areas remained (FIG. 8 panel A). Only minimal staining was observed of the control HI-NHS exposed cells (FIG. 8 panel B).

Example 14

Complement-Mediated Vesiculation of RPE Cell Membranes

To further investigate the effects of MAC deposition and protection, primary (passage 0) mouse RPE cells were contacted with either a mixture of AdCAGCD59+AdCAG-GFP (800+200 vp/cell respectively) or with a control mixture of AdEMPTY+AdCAGGFP (800+200 vp/cell respectively). After seven minutes of NHS treatment, washing and fixation, cells were examined. Three days post-treatment, these cells were analyzed by the MAC deposition assay.

Presence of numerous GFP-positive vesicles associated with cells was observed (FIG. 10 panels A and B, arrows). Examination of the cells revealed the presence of numerous GFP-positive vesicles (FIG. 10 panels A and B, arrows). The number and size of these vesicles was substantially greater for cells contacted with the mixture of AdEMPTY+AdCAG-GFP (FIG. 10 panel A) compared to cells contacted with the mixture of AdCAGCD59+AdCAGGFP (FIG. 10 panel B). This observation indicates that the vesiculation observed herein was a result of MAC deposition. Furthermore, after contacting with NHS, cells contacted with the mixture of AdEMPTY+AdCAGGFP showed a reduction in GFP fluorescence compared to fluorescence of cells contacted with the mixture of AdCAGCD59+AdCAGGFP (FIG. 10 panel A compared to panel B). The reduced GFP fluorescence in cells contacted with the mixture of AdEMPTY+AdCAG-GFP was associated with a concomitant increase in diffuse green fluorescence observed outside of these cells, indicating that GFP had leaked from the cells or had diffused across the plasma membrane in these control cells.

Example 15

Protection of Ocular Tissues and Primary RPE Cells from MAC Deposition by Adenovirus Delivered hCD59

Efficacy of hCD59 to protect murine RPE from human MAC deposition was assessed. Mice were administered in vivo subretinal injections of each adenovirus vector. Six days after injection, expression of hCD59 on murine RPE following subretinal injection of the AdCAGCD59 vector was observed by immunohistochemistry with anti-hCD59 antibody (FIG. 11 panel A). Staining for hCD59 was not observed in eyecup tissues that had been injected with the negative control AdCAGGFP (FIG. 11 panel B; top row). Rather, GFP fluorescence was visible at the site of injection (FIG. 11 panel B; bottom row).

For the MAC deposition assay, subretinal injections were performed in two groups of mice. Mice in one group were injected with a mixture of AdCAGCD59 and AdCAGGFP vectors in a 9:1 ratio (AdCAGGFP was co-injected to allow easy identification of the injection site and area of transgene expression by spontaneous fluorescence). Mice from the second group were injected with a control mixture of AdEMPTY and AdCAGGFP (negative controls) also in a 9:1 ratio. Six days after injection, eyes were harvested and eyecup tissues were exposed to anti-mouse emmprin and NHS, along with eyecup tissues from uninjected control mice.

Immunohistochemistry for human MAC of eyecup tissues injected with the mixture of AdCAGCD59 and AdCAGGFP (n=10) showed significantly reduced staining on the RPE at the area of GFP expression (which was used to identify and was found to correlate with hCD59 expression) compared to the uncontacted remaining area of eyecup tissue (FIG. 12 panel B, compare dissected tissues on top row). The RPE cells at this area appeared undamaged with defined cell boundaries and normal hexagonal morphology (FIG. 12 panel B, compare photomicrograph of cells with those in FIG. 12 panel A). In contrast, MAC immunostaining at the GFP expressing area of tissues injected with negative control vectors (mixture of AdEMPTY and AdCAGGFP vectors) of the injected eyecup tissues (n=10) was similar to the uncontacted remaining area of the eyecup tissue (FIG. 12 panel A), and, MAC immunostaining was significantly more extensive and stronger than the MAC immunostaining observed at the area of GFP expression of eyecup tissues injected with the mixture of AdCAGCD59 and AdCAGGFP. Further, the RPE cells at the GFP expressing area of negative control injected eyecup tissues appeared extensively damaged as indicated by their rounded shape, loss of normal hexagonal morphology and loss of defined cell boundaries (FIG. 12 panel A, photomicrographs compared to those in FIG. 12 panel B).

Quantification of the MAC immunofluorescence at the area of GFP expression revealed an overall reduction of ~55% in mean MAC immunofluorescence intensity on the eyecup tissues injected with the mixture of AdCAGCD59 and AdCAGGFP (n=10) compared to eyecup tissues injected with the mixture of the negative control (n=10), a difference which was statistically significant (p=0.0014, FIG. 13 panel A). These calculations showed that mean MAC fluorescence intensity on the eyecup tissues injected with the mixture of AdCAGCD59 and AdCAGGFP was increased by the lack of significant protection from MAC deposition for only a few eyecup tissues with poor hCD59 expression as indicated by GFP expression, and the figure of 55% was affected by inclusion of these samples. It was observed that there was an inverse relationship between the GFP and MAC fluorescence intensities (FIG. 13 panel B) on the eyecup tissues that had been contacted with the mixture of AdCAGCD59 and AdCAGGFP. This inverse relationship indicates that a potential therapeutic method involving expression of CD59 can protect tissues from MAC deposition.

Eyecups were then contacted with mixtures of AdEMPTY and AdCAGGFP, or AdCAGCD59 and AdCAGGFP to analyze the possibility that reduced MAC was a function of transduction of the vector. No significant difference was observed in results between the two groups (n=10 per group) in GFP levels (FIG. 13 panel B). The RPE cell morphology in the AdEMPTY and AdCAGGFP-contacted eyecups and the AdCAGCD59 and AdCAGGFP-contacted eyecups were similar (FIG. 12 panels D and E). Further, MAC staining of the AdEMPTY and AdCAGGFP-contacted eyecups was significantly greater than that of the AdCAGCD59 and AdCAGGFP-contacted eyecups (FIG. 12 panels D and E).

Quantification of reduction in MAC immunofluorescence at the area of GFP expression revealed an average of about 68% (p=0.0018) at 7.5 minutes NHS treatment and 56% (p=0.0007) at 15 minutes NHS treatment on the AdCAGCD59+AdCAGGFP-contacted eyecups compared to AdEMPTY+AdCAGGFP -contacted eyecups (FIG. 12 panel C). Moreover, an inverse relationship between the GFP and MAC fluorescence intensities on the AdCAGCD59+AdCAGGFP-contacted eyecups compared to AdEMPTY+AdCAGGFP-contacted eyecups (FIG. 13 panel B). This further indicates that protection from MAC deposition is a function of the level of hCD59 expression.

It is possible that the difference in MAC deposition between AdCAGCD59 and negative control contacted eyecup tissues was due to a difference in mouse emmprin expression and/or to a difference in anti-emmprin antibody binding. To evaluate this possibility, immunohistochemistry for mouse emmprin on eyecup tissues contacted by pretreatment with the mixture of AdCAGCD59 and AdCAGGFP or eyecup tissues contacted with the negative control (mixture of AdEMPTY+AdCAGGFP) was performed. Anti-mouse emmprin antibody analysis was performed using the same procedure as for the MAC deposition assay, and eyecup tissues were washed, fixed and incubated with an appropriate Cy3-conjugated antibody. No differences in emmprin immunofluorescence on the RPE were observed between the area of transgene expression and the rest of the eyecup tissue (FIG. 14 panels A and B) or uninjected control eyecup tissues (control). Further, no differences in emmprin immunofluorescence were observed between the areas of transgene expression of eyecup tissues injected with the mixture of AdCAGCD59 and AdCAGGFP compared to negative control injected eyecup tissues (FIG. 14 panels A and B). These data clearly show that protection of murine RPE from human MAC deposition was due to the in vivo expression of adenovirus delivered hCD59.

No differences in emmprin immunofluorescence were observed between the areas of transgene expression of the mixture of AdCAGCD59+AdCAGGFP, and in control injected eyecups (FIG. 14 panels A and B and FIG. 15) observed at two magnifications. Similar results were obtained with primary mouse RPE cells (FIG. 16). Passage 0 RPE cells were contacted with about 500 vp/cell of AdCAGCD59 vector or AdCAGGFP vector, and three days after contacting, cells were contacted with the anti-mouse emmprin antibody followed by exposure to 50% NHS for four minutes. Immunohistochemistry showed a significant reduction in MAC immunostaining of cells contacted with AdCAGCD59 vector compared to cells contacted with AdCAGGFP vector (FIG. 16), data for the latter of which MAC immunofluorescence were similar to that for primary mouse RPE cells not contacted with any vector (control).

Primary murine RPE cells contacted with AdCAGGFP (FIG. 14 panel C) or AdCAGCD59 (FIG. 14 panel D) assayed by immunohistochemistry methods showed that expression of hDC59 resulted in no changes in emmprin expression levels in primary mouse RPE cells.

Protection from MAC deposition was not due to differences in emmprin expression and/or anti-emmprin antibody binding as immunocytochemistry for mouse emmprin revealed no differences between control and. AdCAGCD59 contacted cells. The data described demonstrate the destructive effects of human MAC deposition on the RPE and on primary RPE cells and significant protection of these cells by expression of hCD59.

Example 16

Protection of Corneal Endothelium from MAC Deposition by Vector-Mediated Delivery of hCD59

MAC deposition and protection by adenovirus-delivered hCD59 was further assayed using murine corneal epithelium. Corneal epithelium is easily accessible tissue and cultured, and was contacted with adenovirus and other vectors in vivo and ex vivo. In addition, assays herein using corneal endothelium were shown to be efficient for homogenous transduction of the endothelial cells and efficient measurement of other factors such as agents that affect complement regulators. Investigation of MAC deposition on corneal endothelium is further useful for screening inhibitors of MAC deposition and complements testing in RPE in vitro and in vivo.

Delivery ex vivo of hCD59 to the corneal endothelium was observed herein to significantly protect those cells from human MAC deposition upon further mixing with the anti-mouse emmprin antibody and 50% NHS for 20 minutes (FIG. 17 panel B; see also FIG. 11 panel C). In contrast, delivery of control marker protein GFP failed to protect the corneal endothelium from human MAC deposition (FIG. 17 panel A), which was observed to be similar in extent to MAC deposition on the corneal endothelium of corneas that had not been treated (control; FIG. 9 panel C). GFP expression on the conical endothelium of NHS contacted corneas appeared fragmented (FIG. 17 panel A), for example due to loss of endothelial cells following damage by deposition of the MAC. This fragmentation was not observed with control corneas not exposed to NHS (FIGS. 11 panel D and FIG. 17 panel C). Data showed that protection of corneal endothelium from MAC by AdCAGCD59 was not due to a difference in emmprin expression and/or anti-emmprin antibody binding as immunohistochemistry revealed no differences in emmprin immunostaining on the corneal endothelium contacted with each of AdCAGCD59 and control AdCAGGFP (FIG. 17 panels C and D).

Contacting corneas with the anti-mouse emmprin antibody followed by addition of 50% NHS for 20 minutes at 37° C. resulted in extensive, bright MAC immunostaining on the corneal endothelium (FIG. 18 panel A). Minimal staining was observed on the endothelium of 50% HI-NHS treated corneas (for 20 minutes at 37° C.). To assess efficacy of hCD59 to protect the corneal endothelium from human MAC deposition, corneas were contacted ex vivo with the AdCAGCD59 or the control AdCAGGFP vectors.

Expression of hCD59 on the corneal endothelium following ex vivo infection with the AdCAGCD59 was observed by immunohistochemistry using the anti-hCD59 antibody, and no staining for hCD59 was observed on control (AdCAGGFP)-contacted corneas (FIG. 18 panel B). Pretreatment of conical endothelium with hCD59 significantly protected those cells from human MAC deposition, as data showed a reduction in MAC immunofluorescence intensity of 86% ($p<0.0001$, FIG. 18 panel C) compared to pretreatment with GFP, which failed to protect the corneal endothelium as MAC deposition levels were similar to those on the corneal endothelium of control corneas not contacted. Moreover, the GFP expression on the corneal endothelium of NHS treated corneas appeared fragmented indicating loss of endothelial cells due to damage by deposition of the MAC. This fragmentation was not observed on AdCAGGFP-contacted corneas not exposed to NHS (FIG. 18 panels B and D).

The protection from MAC deposition on the conical endothelium of AdCAGCD59-contacted corneas was shown not to be due to a difference in emmprin expression and/ or anti-emmprin antibody binding, as immunohistochemistry data showed no differences in emmprin immunostaining on the corneal endothelium of each of AdCAGCD59 and AdCAGGFP-contacted, and control (not contacted) corneas (FIG. 18 panel D).

These data further show that hCD59 pretreatment protects ocular tissues from MAC deposition. Protection on the conical endothelium was observed to be higher than that of the RPE. Additional factors might affect this protection, such as higher and more homogenous transduction of endothelium of ex vivo contacted corneas and efficiency of modulators and regulators of serum components, and of other possible agents that affect macular degeneration.

Example 17

Soluble Secreted hCD59 Construct and Human CD59 Expression in Vector-Contacted Cells The CD59 constructs used in examples above were constructed to express a membrane associated protein through a GPI linker. Human CD59 lacking the sequence coding for the C terminal 26 amino acids, which includes a signal sequence for attachment of the GPI anchor was PCR amplified using a forward primer containing an XhoI site (underlined) (5'ccccctcgagtggacaatcacaatggg3'; SEQ ID NO: 1) and a reverse primer with an EcoRV site (underlined) (5'taaggagatatcttaattttcaagctgttcgtta3'; SEQ ID NO: 3). The reverse primer introduced a stop codon following Asparagine 77 resulting in a sequence that encodes a soluble form of human CD59. The XhoI/EcoRV digested PCR product was cloned into XhoI/EcoRV digested pShCAG and the resulting plasmid pShCAGsCD59 was used to produce the adenovirus AdCAGsCD59 as described herein. Thus, the GPI signal was removed by recombinant methods to obtain a construct that expresses a soluble, secreted version, and analyses were performed to test whether the secreted version might be useful as a therapeutic agent, as it would more readily spread through the retina and confer protection from MAC deposition for cells that were not directly contacted and transduced with a gene transfer vector.

To evaluate this construct, cells were prepared that carry the soluble CD59 construct, either expressed on a plasmid or on an adenovirus, and were grown and expression in medium was determined. FIG. 19 is a photograph of a Western blot. The second channel from the right was the soluble secreted version (with the GPI linker removed) and was labeled AdCAG$_s$CD59/Unfiltered Media on the photograph. The lane shows secretion of a large amount of protein of about 16 KDa. The channel two over to the right of AdCAG$_s$CD59/Unfiltered. Media (i.e., AdCAGCD59, first channel on the right) is the non-soluble form of CD59 from an adenovirus. The signal for the membrane bound version was much weaker because the antibody used on this blot detected the soluble form much better than the membrane bound form. Signal strength was only compared between the same peptide forms.

To determine the effect of expression CD59 having no GPI signal, engineered so that soluble secreted CD59 protein spreads extracellularly and confers protection against MAC deposition on cells that were not directly transduced with a gene transfer vector, the soluble CD59 protein was expressed in cultured RPE cells and conditioned media from those RPE cells used to confer protection against MAC deposition on hepatocytes. Thus these cells and tissues were prepared for in vivo testing of the soluble secreted CD59 construct as a potential improved therapeutic agent, to determine whether this construct is even more efficient in remediation of MAC deposition than the membrane-bound form.

Examples determined the extent that the soluble secreted CD59 expressing vector protected tissues and cells from cell morphology changes and cell lysis associated with MAC deposition. The ability of secreted CD59 to spread extracellularly through the retina and liver from cells infected with an expressing vector, to prevent MAC deposition on a number of cell types including endothelial cells was tested in a model of wet AMD and a humanized in vivo model of dry AMD respectively.

Results from examples herein indicated potential advantages of the soluble form of CD59 as a therapeutic agent for macular degeneration compared to the membrane-bound form. Additional possibilities include use of both the membrane-bound form and the soluble forms under different conditions, or in combination.

Example 18

Soluble Human CD59 was Processed and Secreted In Vitro

An adenovirus containing an expression cassette for membrane-independent humanCD59 was constructed. The amino acid sequence for the membrane-independent CD59 protein is shown below using one letter amino acid symbols:

MGIQGGSVLFGLLLVLAVFCHSGHSLQCYNCP-NPTADCKTAVNCSSDFDACLITKAGLQVYNKCWK-FEHCNFNDVTTRLRENELTYYCCKKDLCNF-NEQLEN (CD59; SEQ ID NO: 4). The corresponding nucleotide sequence for the membrane-independent CD59 protein is shown in SEQ ID NO:5. The membrane-independent human CD59 encoded by the vector lacks the C-terminal 26 amino acids encoding the signal sequence for attachment of the GPI anchor. The human CD59 nucleic acid sequence lacking the nucleotides encoding the C-terminal 26 amino acids was amplified by PCR using SEQ ID NO: 1 and SEQ ID NO: 3 as described in Examples herein. Control viruses AdCAGGFP and AdCAGpA were also constructed. FIG. 20 panel A. The CD59 human protein includes a number of N-glycosylated forms that are approximately 14-18 kDa in molecular weight. The construct was investigated to determine whether expression and secretion of sCD59 was efficient. ARPE-19 cells were injected with either AdCAGsCD59 or a control virus AdCAGGFP at a multiplicity of infection (M.O.I) of 1000. Cell lysate and media were harvested after infection and analyzed by Western blot.

Expression and secretion of sCD59 was observed in media from cells transfected with AdCAGsCD59 (FIG. 20 panel B). The lysate of the cells contacted with AdCAGsCD59 exhibited a discrete band at approximately 15 kDa. Data show no detectable amounts of sCD59 in the media and lysate of the cells contacted with AdCAGGFP (FIG. 20 panel B).

Example 19 sCD59 Conferred Protection Against Human Serum-Mediated Cell Lysis

Media obtained from human ARPE-19 cells transfected with either AdCAGsCD59 or AdCAGGFP were mixed with normal human serum (NHS) to a final serum concentration of 1% (v/v). The media/NHS was then added to mouse Hepa-1c1c7 cells ($4.8 \times 10^5$ cells/ml) and incubated at 37° C. with gentle rotary motion. As a control, cells were also contacted with 1% heat-inactivated normal human serum (HI-NHS) in either AdCAGsCD59- or AdCAGGFP-conditioned media. Hepa-1c1c7 cells were analyzed one hour after incubation for cell lysis by flow cytometry measurement of propidium iodide uptake. FIG. 21 panel A shows a representative histogram of Hepa-1c1c7 cells treated with either HI-NHS or NHS in media conditioned with AdCAG-GFP and AdCAGsCD59, respectively (FIG. 21 panel A). A small amount of cell lysis was observed in Hepa-1c1c7 cells treated with HI-NHS and either the AdCAGGFP-conditioned media (10.68±1.27%) or the AdCAGsCD59-conditioned media (11.03±1.92%), respectively. The small amount of cell lysis observed may have resulted from manipulation of the cells (FIG. 21 panel B).

Greater cell lysis was observed in Hepa-1c1c7 cells treated with NHS and AdCAGGFP-conditioned media (79.87±2.54%) compared to cell lysis in cells treated with NHS and AdCAGsCD59-conditioned media (52.66±4.43%; FIG. 21 panel B). Hepa-1c1c7 cells contacted with AdCAGsCD59-conditioned media and NHS were protected to a significant extent (34.08±6.40%, $p<0.01$) against cell lysis compared to results obtained from Hepa-1c1c7 cells contacted with AdCAGGFP-conditioned media and NHS.

Example 20

Injection of Adenovirus into the Subretinal Space did not Affect Laser-Induced CNV Size To determine whether ocular delivery of an adenovirus into an eye of a mouse would affect the amount of choroidal neovascularization (CNV) induced by laser burn, vectors were designed to test whether the presence of the vector altered the CNV model system. Vector AdCAGpA was mixed in a 1:10 ratio with vector AdCAGGFP to localize the injection site, and was injected into the subretinal space of six week-old C57B16/J mice. After 72 hours from injection with the vector mixture AdCAGpA/ADCAGGFP, mice were subjected to laser burn treatment. Laser burn treatment involved dilating each pupil with a drop of each of 2.5% phenylephrine hydrochloride and 1% Tropicamide (Bausch and Lomb; Madison, N.J.). A drop of 2.5% Hypromellose/Gonak (Akorn Inc.; Somerset, N.J.) was then applied to the cornea and the back of the eye, which was viewed with a microscope and a coverslip held on the cornea. Three laser spots (75 μm) were made on each eye using an argon laser (532 nm; 100 milliseconds; 150 mW). Control animals not injected were also subject to laser burn treatment. The subjects were then kept for an additional seven days to allow CNV to develop in the eyes. Eyes were harvested, cornea, lens, and retina removed, and RPE/choroid flatmounts were incubated for 30 minutes in 2.5 mg/ml BSA in PBS and then were stained for one hour at 37° C. with a FITC-conjugated GSL I, isolectin B4, a lectin specific for endothelial cells (Vector Labs; Burlingame, Calif.).

A representative micrograph of a CNV spot for eyes injected with AdCAGpA/AdCAGGFP and eyes from mice that were not injected, respectively are shown in FIG. 22 panel A. The average size of a laser CNV spot in eyecups injected with AdCAGpA/AdCAGGFP was 0.31±0.03mm², and the average spot size in the eyecups from mice that were not injected was 0.27±0.06mm² No significant difference in CNV spot size was observed in eyes from mice injected with AdCAGpA/AdCAGGFP and eyes from mice that were not injected ($p>0.5$; FIG. 22 panel B). These data show that adenovirus vector delivery into the murine subretinal space did not significantly affect CNV induced by laser burn treatment.

Example 21

Delivery of AdCAGsCD59 to Murine RPE Reduced Laser-Induced CNV

Each vector AdCAGpA and AdCAGsCD59 was mixed in a 1:10 ratio with vector AdCAGGFP, and the resulting mixtures were injected ($2.4 \times 10^7$ total particles of adenovirus) into murine subretinal space. Eyes were treated with laser to induce burns as described herein. Seven days after laser treatment, RPE/choroid flatmounts were stained with FITC-conjugated GSL I, isolectin B4. Representative micrographs of the region of adenovirus transduction relative to the sites of laser burn for each of the eyes injected with AdCAGpA and AdCAGsCD59 respectively are shown in FIG. 23 panel A. No significant difference in area of transduction ($p>0.05$) was observed between eyecups from mice injected with AdCAGpA (0.69±0.09mm²) compared to eyecups in mice injected with AdCAGsCD59 (0.62±0.87mm²; FIG. 23 panel B).

CNV spots from both groups of mice were imaged by confocal microscopy and the size of each CNV spot measured. Representative micrographs of a CNV spot from an eyecup injected with AdCAGpA and a CNV spot from an eyecup injected with AdCAGsCD59 respectively are shown in FIG. 24 panel A. The average size of the CNV spot in eyecups from mice injected with AdCAGpA was 0.31±0.03mm$^2$, the average spot size in eyecups from mice injected with AdCAGsCD59-injected was 0.12±0.02mm$^2$ (FIG. 24 panel B).

A significant (61.0±11.6%, $p<0.0001$) reduction in size of the CNV spot was observed for eyecups in mice injected with AdCAGsCD59 compared to eyecups in mice injected with AdCAGpA. These data show that delivery of AdCAGsCD59 to murine RPE conferred significant protection against laser-induced CNV.

Example 22

AdCAGsCD59 Transduction of Murine RPE Reduced MAC Deposition at the Site of CNV

RPE/choroid flatmounts were injected with either AdCAGpA or AdCAGsCD59 and subjected to laser burn as described herein. The injected eyecups were then stained with a 1:200 dilution of anti-mouse C9 antibody for 2.5 hours at room temperature and then 1:400 dilution of CY3-conjugated goat anti-rabbit antibody at room temperature for one hour.

MAC staining in the RPE/choroid flatmounts injected with AdCAGpA was observed to extend beyond the region of GSL I staining (FIG. 25 panel A). The RPE/choroid flatmounts injected with AdCAGsCD59 resulted in MAC deposition that was confined to the region of GSL I staining. These data show that cells adjacent to the CNV spot in the RPE/choroid flatmounts injected with AdCAGsCD59 were protected from MAC deposition. Quantification of MAC staining showed a significant 40.9±13.3% reduction in MAC deposition in eyecups injected with AdCAGsCD59 (FIG. 25 panel B, $p<0.01$) compared to the eyecups injected with AdCAGpA.

Example 23

Preparation of Adenovirus-Associated Virus Expressing sCD59 and Protection in the Animal Model Laser-Induced CNV Adenovirus-associated virus (AAV) serotype 2, which efficiently infects retinal ganglion cells after intravitreal delivery to mouse eye, was used to prepare a vector for delivery of sCD59. See FIG. 26 panel A. The nucleotide sequence encoding amino acid sequence for the sCD59 protein and the amino acid sequence for the sCD59 protein was SEQ ID NO: 5 and SEQ ID NO: 4 respectively. Intravitreal injection is a more widely used approach for ocular drug delivery than subretinal injection, and is used routinely for administration of anti-VEGF treatments for "wet" AMD.

The AAV vector construct expressing membrane-independent human CD59 was injected ($8\times10^9$ genome copies) into the vitreous of the eyes of six to eight week old mice. Control mice were injected with an AAV-2 vector containing a GFP transgene. The RPE of injected animals were subjected to laser burn treatment between 12 and 19 days post-injection. Eyes were harvested seven days after laser burn treatment.

A significant reduction in CNV size was observed in eyecups in mice intravitreally injected with AAVCAG-sCD59 (56.0±18.1%; $p<0.01$) compared to the eyecups in mice intravitreally injected with AAVCAGGFP. FIG. 26 panel B. The average size of the CNV spot in eyes injected with AAVCAGsCD59 was 0.16±0.03mm$^2$ compared to control AAVCAGGFP which was 0.36±0.06mm$^2$ (FIG. 26 panel C).

Example 24

MAC Deposition onto Endothelial Cells Required a Cell-Specific Antibody

To test whether human complement would be activated by murine endothelial cells, methods herein were used to develop an ex-vivo human MAC (hMAC) deposition. Explants of murine aortas were incubated with either NHS alone or with NHS and generic anti-mouse (GAM) antibody. Each aorta was stained with an antibody specific for human MAC (hMAC) to detect MAC complex deposition on the tissues (FIG. 27).

Low levels of MAC staining were observed along the luminal surface of aortas incubated with either NHS alone or with NHS in combination with GAM. Membrane staining was observed on individual cells (FIG. 27), however the staining was patchy and non-uniform across the surfaces of the aortas. Additional aortas were incubated with an anti-murine PECAM1 (mPECAM) antibody prior to incubation with NHS. PECAM is an endothelial cell surface marker.

The aortas incubated with anti-mPECAM antibody prior to incubation with NHS showed more robust and homogeneous MAC staining compared to aortas incubated with GAM antibody and NHS (compare FIG. 27 panels A and B). MAC deposition of the aortas incubated with anti-PECAM antibody was observed to be uniform across the luminal surface, and these aortas resulted in cell-boundary staining of individual cells (FIG. 27 panel B). Incubation of aortas with anti-mPECAM1 in the presence of HI-NHS did not result in MAC staining along the aortal luminal surface (FIG. 27 panel C).

Example 25

Intra-Cardial Delivery of Anti-mPECAM-1 Resulted in Antibody Binding to Endothelial Cells in Various Tissues Anti-mPECAM1 antibody, an endothelial cell-specific antibody, is used in methods described herein for activating human complement on mouse endothelial cells. Anti-mPECAM1 was delivered in vivo to C57B16/J mice using intra-cardial injection. Four hours after the animals were injected intra-cardially, tissues were stained with a CY3-conjugated goat anti-hamster antibody.

Anti-mPECAM1 antibody was detected on endothelial cells in the following tissues: the liver, the retina, the choroid, and the aorta (FIG. 28 left column). Anti-mPECAM antibody was observed bound to endothelial cells of both the sinusoids (sECs) and larger blood vessels (i.e., arteries and veins) in the liver (FIG. 28 panel A left column). The observed staining was most prominent on the sECs, however staining was observed also on the lumen of larger blood vessels. The anti-mPECAM antibody was also detectable on endothelial cells of the retinal vasculature, as well as on those of the choriocapillaris of the choroid (FIG. 28 panels C and D left column).

Detection of the anti-mPECAM1 antibody on the endothelial cells of the choriocapillaris, capillaries forming the inner vascular layer of the choroid of the eye, may be blocked by the presence of choroidal pigments in these tissues. To investigate detection of antibody binding to endothelial cells of the choriocapillaris, anti-mPECAM1 antibody and GAM antibody were each intra-cardially injected into BALB/C mice. Animals were sacrificed and choroidal/RPE flatmounts were removed and stained with CY3-conjugated goat anti-hamster antibody (FIG. 28 right column).

Data show extensive binding of anti-mPECAM1 antibody along the choriocapillaris. Intra-cardial injection of GAM resulted in high levels of non-specific binding to the endothelium in the liver, retina, and choroid (FIG. 28 right column). Higher magnification of the stained tissues shows significant staining of the luminal surface of tissues injected with anti-mPECAM1 antibody compared to the staining of luminal surface of tissues injected with GAM antibody (FIG. 28 compare left column and right column).

Example 26

Intra-Cardial Delivery of mPECAM1 Antibody and Perfusion with NHS Resulted in hMAC Deposition on Endothelial Cells of the Liver Intra-cardial injection of anti-mPECAM1 antibody was observed herein to be detectable in tissues of animals. Mice were injected intra-cardially with anti-mPECAM antibody and were then perfused either with NES or with HI-NHS. Animals were sacrificed and tissues including the liver, choroid, and retina were stained for hMAC deposition fifteen minutes after the serum infusion.

The MAC staining images of animal liver sections infused with anti-mPECAM1 and NHS were observed to be similar to the images of animal liver sections incubated with mPECAM1 and stained with CY3-conjugated goat anti-hamster antibody. (Compare FIG. 28 panel A left column and FIG. 29 panel A left column). MAC staining was most prominent on endothelial cells of the sinusoids and larger blood vessels (FIG. 29 panel A). Further, MAC deposition was observed in liver sections of mice intra-cardially injected with anti-mPECAM antibody and perfused with NHS was significantly higher than MAC deposition for mice injected with anti-mPECAM antibody and perfused with heat-inactivated NHS (HI-NHS; FIG. 29 panel B). The average overall intensity of representative regions of the mice perfused with NHS was $1.81 \times 10^7$ IU, and the average overall intensity of mice perfused with HI-NHS was $0.48 \times 10^7$ ($p<0.01$; FIG. 29 panel B).

These data show a 3.77-fold increase in MAC deposition in mice intra-cardially injected with anti-mPECAM antibody and perfused with NHS compared to mice perfused with HI-NHS. No MAC deposition was detected in other tissues of mice perfused either with NHS or with control HI-NHS.

Example 27

Intraperitoneal Injection of an Adenovirus Expressing Membrane-Independent Human CD59 Reduced MAC Deposition on Liver Endothelial Cells Alternative routes of administering the viral constructs expressing human membrane-independent CD59 and controls were investigated. Intraperitoneal injection of an adenovirus expressing GFP (AdCAGGFP) resulted in GFP expression mainly along the peritoneal membrane of the liver and also expression of GFP by cells within the liver (FIG. 30).

The adenovirus expressing membrane-independent human CD59 (AdCAGsCD59) was administered to mice, as was control AdCAGGFP, by intraperitoneal injection. Animals were injected seven days later with anti-mPECAM1 antibody and were perfused with NHS. Animals were sacrificed and tissue samples were removed and stained for human MAC deposition.

MAC staining was observed in the liver sections from mice injected with AdCAGGFP (FIG. 31 panel A right column). The staining in these liver sections was similar to the staining patterns previously observed for liver sections from mice without adenovirus infection (Compare FIG. 28 panel A to FIG. 31 panel A). Liver sections of animals injected with AdCAGsCD59 showed little or no MAC staining (FIG. 31 panel A). The average overall MAC staining intensity of the liver sections of the mice injected with AdCAGsCD59 was $1.60 \times 10^7$ IU. Intensity of MAC staining in animals injected with AdCAGGFP was $4.23 \times 10^7$ IU (FIG. 31 panel B). Data show that MAC staining was significantly reduced (62.1% reduction; $p<0.01$) in mice injected with AdCAGsCD59 compared to mice injected with AdCAGGFP.

Administration of adenovirus alone has been shown to activate complement in animals (Appledore, D. M. et al. 2008 Gene Ther. 15(24): 1606-1617). The anti-MAC antibody used in examples detected both mouse and human MAC. Whether MAC deposition observed resulted from human complement activation between serum and non-self tissues, or mouse complement activation due to the administration of an adenovirus, was therefore determined.

Mice were injected intraperitoneally with AdCAGGFP and were intra-cardially injected after seven days with anti-mPECAM1. Animals were then perfused with PBS$^{++}$ (0.15 mM NaCl, 0.9 mM CaCl$_2$, 0.5 mM MgCl$_2$). Liver sections of the mice perfused with PBS$^{++}$ were observed to not stain positively for MAC.

Thus, the MAC deposition detected in mice injected with adenovirus and perfused with NHS was observed to be a result of human complement activation and not activation of mouse complement by the injection of adenovirus.

Example 28

Delivery of AdCAGsCD59 Protected Endothelial Cells of Blood Vessels in the Liver from MAC Deposition Protection by sCD59 was investigated in endothelial cells of the blood vessels for MAC deposition that was observed on endothelial cells of both the sinusoids and blood vessels. Staining along larger vessel luminal surface in the sCD59 group was observed to be discontinuous and less intense, compared to the staining observed for vessel luminal surface for mice injected with adenovirus expressing GFP (FIG. 32 panel A).

The vessels of livers of mice injected with AdCAGsCD59 were observed to have reduced average MAC staining compared to the livers of mice injected with AdCAGGFP. The average intensity per endothelial cell area in the livers of mice injected with AdCAGsCD59 was 251.27 IU/$\mu m^2$, and for livers of mice injected with AdCAGGFP was 428.95 IU/$\mu m^2$. MAC staining in the vascular endothelial cells of the liver was significantly reduced (41.4%; $p<0.001$) by injected mice with AdCAGsCD59 compared to mice injected with AdGAGGFP (FIG. 32 panel B). These data show that sCD59 significantly protected tissues and cells of subjects against the deleterious effects of complement activation.

What is claimed is:

1. A pharmaceutical composition for treatment of a macular degeneration, the composition comprising an engineered nucleotide sequence encoding a membrane-independent recombinant human CD59 protein, wherein the engineered nucleotide sequence encodes a polypeptide comprising a CD59 fragment consisting of the amino acid sequence set forth in SEQ ID NO: 4, and wherein the engineered nucleotide sequence is recombinantly operably linked to a promoter sequence that initiates expression of the membrane-independent recombinant CD59 protein in cells of a subject, and a pharmaceutically acceptable buffer, and the composition is formulated for ocular deliver and sufficiently pure for administration to the subject in a dose effective to treat the macular degeneration.

2. The pharmaceutical composition according to claim 1, wherein the engineered nucleotide sequence comprises the nucleotide sequence as set forth in SEQ ID NO: 5.

3. The pharmaceutical composition according to claim 1, wherein the engineered nucleotide sequence encoding the membrane-independent CD59 protein does not further encode a fusion to a peptide or protein domain that binds to a cell membrane or membrane associated entity.

4. The pharmaceutical composition according to claim 1, formulated for a route of injection delivery that is at least one selected from the group of intra-ocular, subconjunctival, and subtenon.

5. The pharmaceutical composition according to claim 1, formulated wherein the engineered nucleotide sequence is provided in a vector.

6. The pharmaceutical composition according to claim 5, wherein the vector is an engineered viral vector comprising the nucleotide sequence encoding the membrane-independent CD59 protein.

7. The pharmaceutical composition according to claim 5, wherein the vector is a synthetic gene delivery vector for delivery of the engineered nucleotide sequence.

8. The pharmaceutical composition according to claim 1, provided as an eye drop or an ointment.

9. The pharmaceutical composition according to claim 1, further comprising at least one agent selected from the group consisting of: an anti-tumor, an antiviral, an antibacterial, an anti-mycobacterial, an anti-fungal, an anti-proliferative, and an anti-apoptotic.

10. A kit for treating a macular degeneration in a subject, the kit comprising:
a pharmaceutical composition comprising an engineered nucleotide sequence encoding a membrane-independent recombinant human CD59 protein, wherein the engineered nucleotide sequence encodes a polypeptide comprising a CD59 fragment consisting of the amino acid sequence set forth in SEQ ID NO: 4, and wherein the sequence is operably linked to a promoter sequence which is engineered for expression in vivo in cells of the subject; the composition is formulated for ocular delivery and being sufficiently pure for administration to the subject in a dose effective to treat the macular degeneration,
instructions for use; and
a container.

11. The kit according to claim 10, wherein the nucleotide sequence comprises SEQ ID NO: 5.

* * * * *

SEQUENCE LISTING

```
<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: The sequence has been designed and synthesized

<400> SEQUENCE: 1 cccccctcgag tggacaatca caatggg                                              27

<210> SEQ ID NO 2
<211> LENGTH: 31
<212> TYPE: DNA
<213> ORGANISM: Artificial Sequence
<220> FEATURE:
<223> OTHER INFORMATION: The sequence has been designed and synthesized

<400> SEQUENCE: 2
cccccgatat caacggggag tttgggagaa g                                          31

<210> SEQ ID NO 3
<211> LENGTH: 34
<212> TYPE: DNA
<213> ORGANISM: Artificial Sequence
<220> FEATURE:
<223> OTHER INFORMATION: The sequence has been designed and synthesized

<400> SEQUENCE: 3
taaggagata tcttaattt caagctgttc gtta                                        34

<210> SEQ ID NO 4
<211> LENGTH: 102
<212> TYPE: PRT
<213> ORGANISM: Artificial Sequence
<220> FEATURE:
<223> OTHER INFORMATION: The sequence has been designed and synthesized

<400> SEQUENCE: 4

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
    50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn
            100

<210> SEQ ID NO 5
<211> LENGTH: 309
<212> TYPE: DNA
<213> ORGANISM: Artificial Sequence
<220> FEATURE:
<223> OTHER INFORMATION: The sequence has been designed and synthesized

<400> SEQUENCE: 5
```

```
atgggaatcc aaggagggtc tgtcctgttc gggctgctgc tcgtcctggc tgtcttctgc    60
cattcaggtc atagcctgca gtgctacaac tgtcctaacc caactgctga ctgcaaaaca   120
gccgtcaatt gttcatctga ttttgatgcg tgtctcatta ccaaagctgg gttacaagtg   180
tataacaagt gttggaagtt tgagcattgc aatttcaacg acgtcacaac ccgcttgagg   240
gaaaatgagc taacgtacta ctgctgcaag aaggacctgt gtaactttaa cgaacagctt   300
gaaaattaa                                                           309
```